US006300110B1

(12) United States Patent
Villeponteau et al.

(10) Patent No.: US 6,300,110 B1
(45) Date of Patent: Oct. 9, 2001

(54) PEPTIDES RELATED TO TPC2 AND TPC3, TWO PROTEINS THAT ARE COEXPRESSED WITH TELOMERASE ACTIVITY

(75) Inventors: Bryant Villeponteau; Junli Feng, both of San Carlos; William H. Andrews, Richmond; Robert R. Adams, Redwood City, all of CA (US)

(73) Assignee: Geron Corporation, Menlo Park, CA (US)

( * ) Notice: Subject to any disclaimer, the term of this patent is extended or adjusted under 35 U.S.C. 154(b) by 0 days.

(21) Appl. No.: 09/220,157

(22) Filed: Dec. 23, 1998

Related U.S. Application Data

(63) Continuation of application No. 08/710,249, filed on Sep. 13, 1996, now Pat. No. 5,858,777, which is a continuation-in-part of application No. 08/583,808, filed on Jan. 5, 1996, now abandoned.
(60) Provisional application No. 60/003,492, filed on Sep. 9, 1995.

(51) Int. Cl.[7] ............................. C12N 9/12; C12N 1/20; C12N 15/00; C12P 21/06; C07H 21/04
(52) U.S. Cl. ................. 435/194; 435/252.3; 435/320.1; 435/69.1; 435/254.11; 530/300; 530/350; 536/23.2
(58) Field of Search .............................. 435/194, 252.3, 435/320.1, 69.1, 254.11; 530/350, 300; 536/23.2

(56) References Cited

U.S. PATENT DOCUMENTS

| 5,489,508 | 2/1996 | West et al. ............................... 435/6 |
| 5,580,726 | 12/1996 | Villeponteau et al. .................. 435/6 |
| 5,583,016 | 12/1996 | Villenponteau et al. ............ 435/91.3 |

FOREIGN PATENT DOCUMENTS

| WO 93/23572 | 11/1993 | (WO) . |
| WO 94/11531 | 5/1994 | (WO) . |
| WO 96/01835 | 1/1996 | (WO) . |

OTHER PUBLICATIONS

GenBank Accession No. AC004601. Human 11p14.3 PAC clone pDJ939m16, complete sequence.
Adams et al; "Initial assessment of human gene diversity and expression patterns based upon 52 million basepairs of cDNA sequence"; sequence of ET81752 Homo sapiens cDNA 3' end similar to U1 small nuclear ribonucleoprotein, 70 kDA, Sep. 6, 1995; Database EST–STS and EST–STS–Two on MP–Search Accession No. T29492.
Collin, "Structure and function of telomerase"; Curr. Opin. Cell. Bio.; 1996; vol. 8, No. 3; pp. 374–380.
De Lange, T.; "In search of vertebrate telomeric protein", Cell & Development Biology, 1996; vol. 7; pp. 23–29.
Feng et al.; (1995); "The RNA Component of Human Telomerase"; *Science* 269:1236–1241.
Hara et al.; "Structure and evolution of four POU domain genes expressed in mouse brain"; *Proc. Nat. Acad. Sci*, USA; Apr. 1992; vol. 89; pp. 3280–3284.
Hillier et al.; "The Walsh U–Merck EST project"; sequence yo33b06.rl Homo sapiens cDNA clone 179699, Sep. 18, 1995; Database EST/EST–TWO on MPSEARCH Accession No. H51230.
Linskens et al. (1995); "Cataloging altered gene expressing in young and senescent cells using enhanced differential display" *Nucl. Acids Res.* 24:3244–3251.
Suzuki et al. (1996), "Efficient isolation of differentially expressed genes by means of newly established method, 'ESD'," *Nucl. Acids Res.* 24:797–799.
Hillier et al.; Genebank, Accession No. R19233.
Counter et al.; PNAS 91:2900–2904 (1994).
Accession No.: X75014. See result 9 of the sequence search.
Accession No.: F13486. See result 5 of the sequence search.

*Primary Examiner*—Ponnathapu Achutamurthy
*Assistant Examiner*—Tekchand Saidha
(74) *Attorney, Agent, or Firm*—Geron Corporation; J. Michael Schiff; David J. Earp

(57) ABSTRACT

Purified and recombinant proteins TPC2 and TPC3 and recombinant or synthetic oligonucleotides corresponding to those proteins or fragments thereof can be used to detect regulators of telomere length and telomerase activity in mammalian cells and for a variety of related diagnostic and therapeutic purposes.

15 Claims, 22 Drawing Sheets

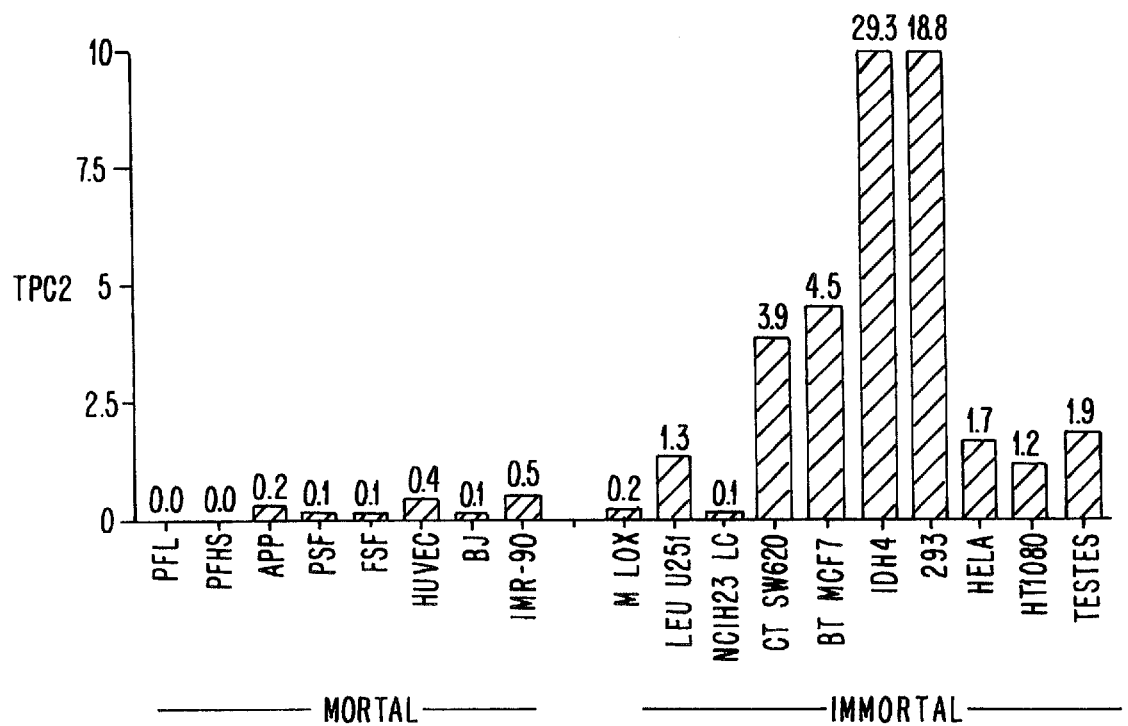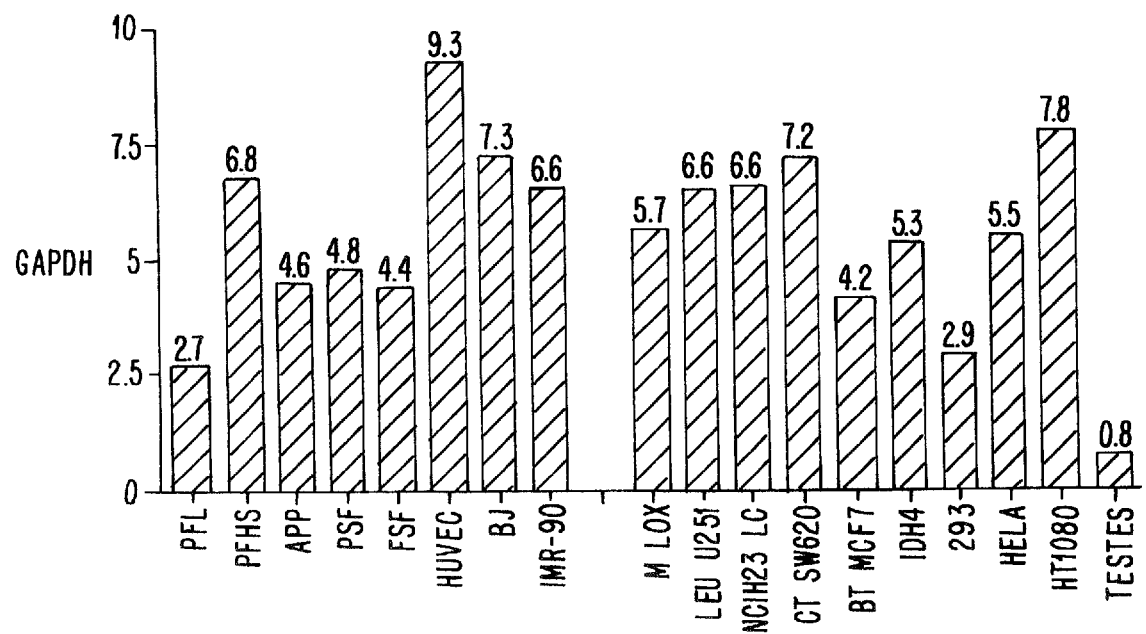
FIG. 1A.

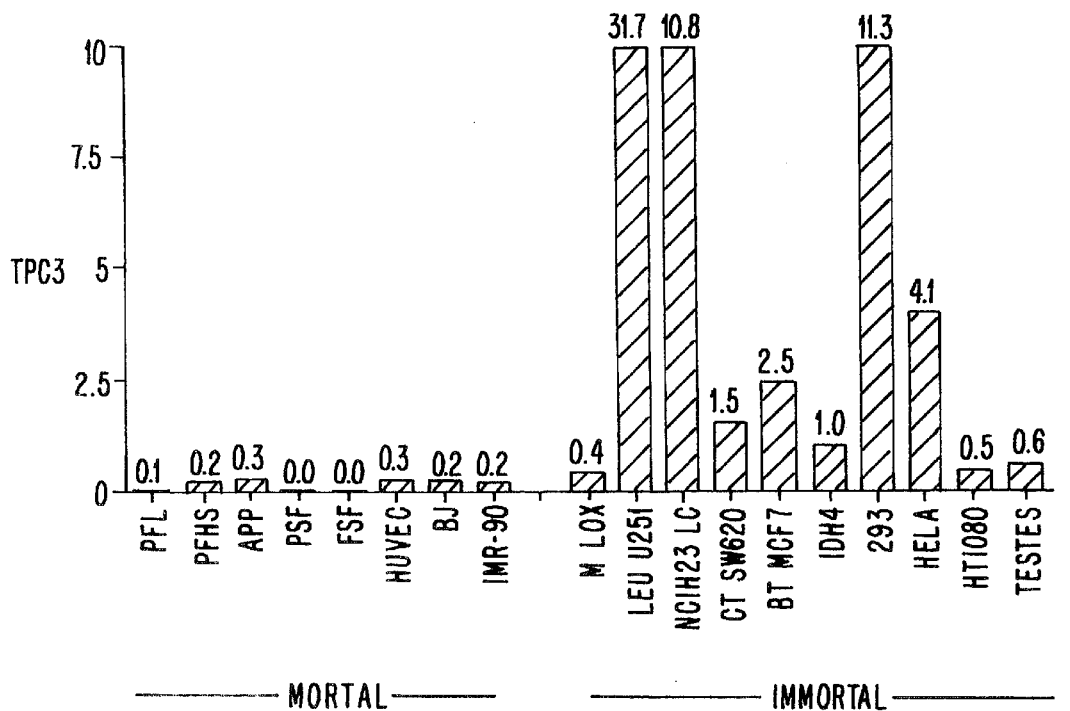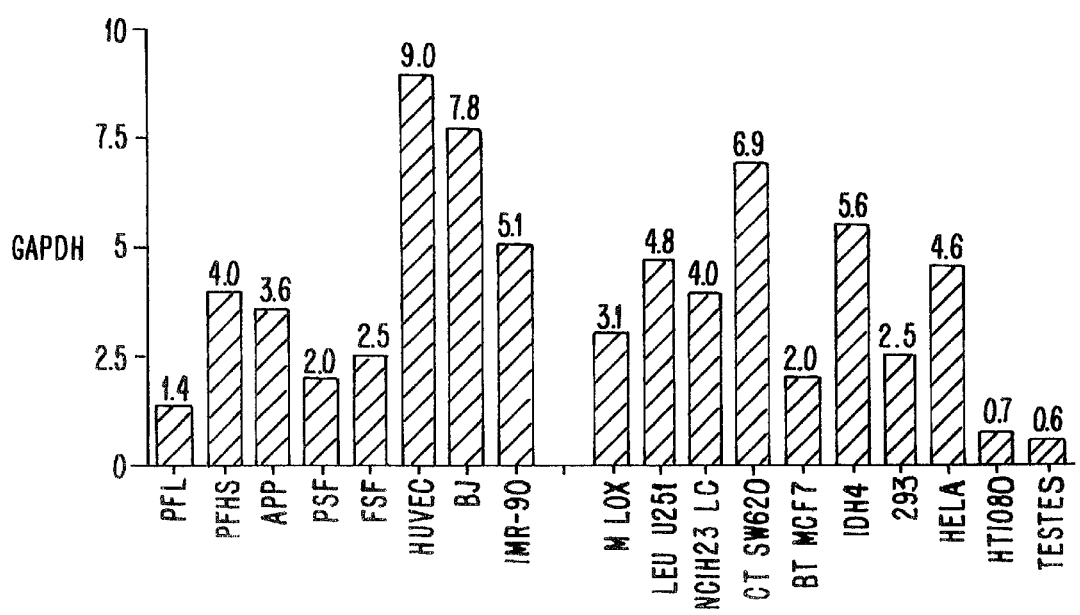
FIG. 1B.

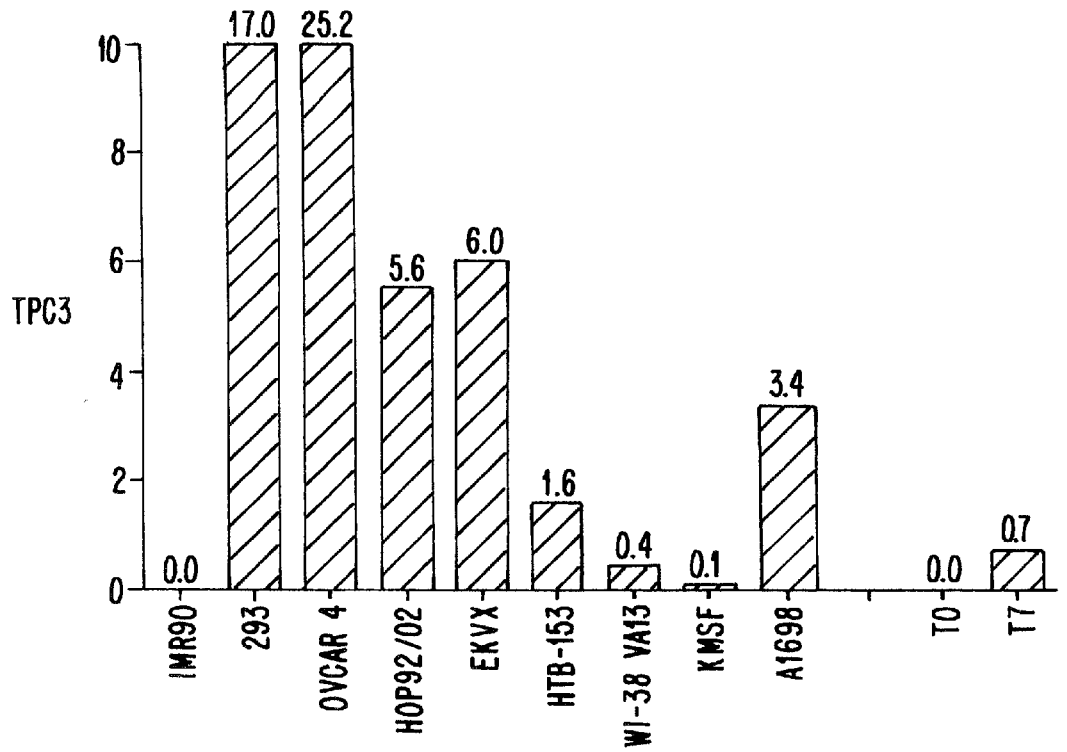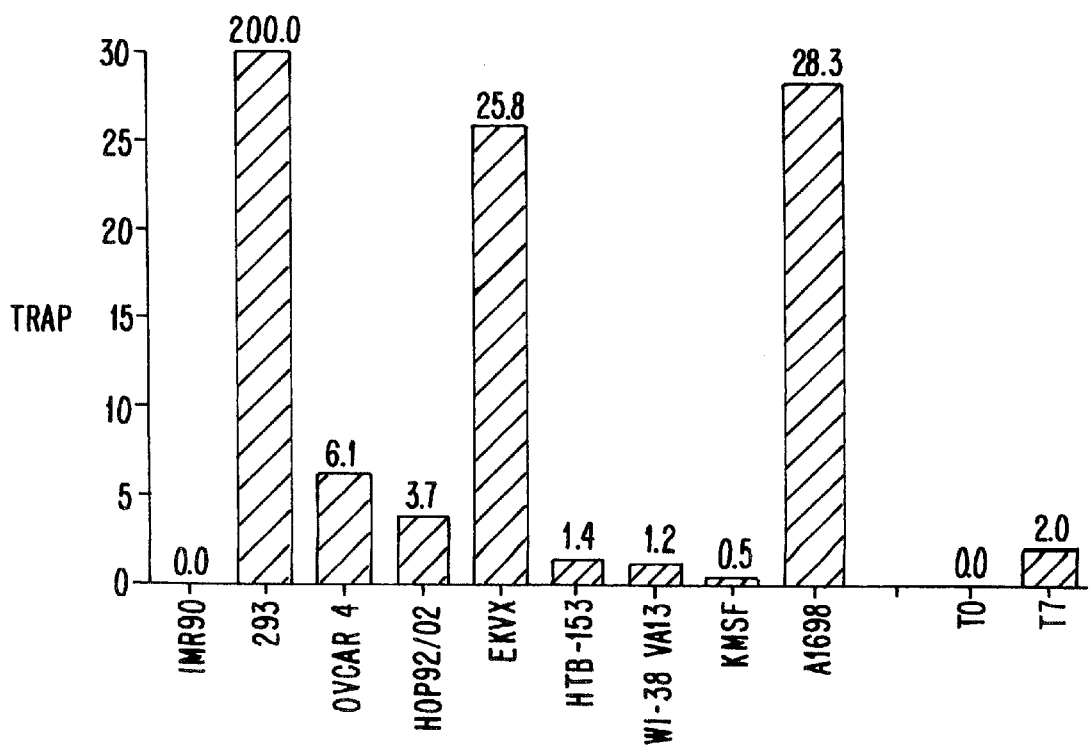
FIG. 2B.

```
     ProArgSerAlaAsnMetAlaAlaAlaThrValGlyArgAspThrLeuPro
  1  CCGCGCTCGGCGAACATGGCGGCGGCGACGGTCGGGCGGGACACTTTACCT

GluHisTrpSerTyrGlyValCysArgAspGlyArgValPhePheIleAsn
 52  GAGCATTGGTCCTACGGGGTGTGCCGGGATGGCCGCGTCTTCTTCATCAAT

AspGlnLeuArgCysThrThrTrpLeuHisProArgThrGlyGluProVal
103  GACCAGCTCCGCTGCACGACCTGGCTGCACCCGCGCACCGGGGAGCCCGTC

AsnSerGlyHisMetIleArgSerAspLeuProArgGlyTrpGluGluGly
154  AACTCGGGCCACATGATCCGCTCAGACCTGCCCCGCGGCTGGGAGGAGGGC

PheThrGluGluGlyAlaSerTyrPheIleAspHisAsnGlnGlnThrThr
205  TTCACGGAGGAGGGCGCCAGCTACTTCATCGACCATAACCAGCAGACCACA

AlaPheArgHisProValThrGlyGlnPheSerProGluAsnSerGluPhe
256  GCATTCAGGCATCCTGTGACGGGACAGTTTTCTCCAGAAAATAGTGAATTC

IleLeuGlnGluGluProAsnProHisMetSerLysGlnAspArgAsnGln
307  ATTCTTCAAGAAGAGCCGAATCCACATATGTCGAAGCAAGACAGAAACCAA

ArgProSerSerMetValSerGluThrSerThrAlaGlyThrAlaSerThr
358  AGACCGTCCAGCATGGTCAGTGAAACATCCACGGCTGGGACCGCCTCCACC

LeuGluAlaLysProGlyProLysIleIleLysSerSerSerLysValHis
409  CTGGAGGCCAAGCCTGGACCCAAGATCATAAAGTCCAGCAGTAAAGTCCAC

SerPheGlyLysArgAspGlnAlaIleArgArgAsnProAsnValProVal
460  AGCTTTGGGAAGAGAGACCAGGCCATTCGGAGGAACCCCAATGTTCCCGTG

ValValArgGlyTrpLeuHisLysGlnAspSer    GlyMetArgLeuTrp
511  GTGGTGAGGGGCTGGCTGCACAAGCAGGACAGTTYTGGGATGAGGCTGTGG

LysValArgTrpPheValLeuAlaAspTyrCysLeuPheTyrTyrLysAla
562  AAAAGGAGGTGGTTTGTGCTTGCTGATTACTGCTTATTTTACTATAAAGCC

GluLysLysArgSerSer    SerIleProLeuPro    TyrVal    Ser
613  GAGAAGAAGCGGTCCTCGXGGAGCATCCCCTTGCCCAG3TACGTGAT3TCT

ProValAlaProGluAspArgIleSerArgLysTyrSerPheLysAlaVal
664  CCTGTGGCCCCTGAGGATCGCATAAGCCGCAAATATTCCTTTAAGGCTGTG

HisThrGlyMetArgAlaLeuIleTyrAsnSerSerThrAlaGlySerGln
715  CACACGGGGATGCGAGCGCTCATCTATAACAGCTCCACAGCGGGCTCTCAG
```

FIG. 4. (Page 1 of 6)

```
         AlaGluGlnSerGlyMetArgThrTyrTyrPheSerAlaAspThrGlnGlu
 766 GCCGAGCAGTCAGGCATGAGGACCTACTACTTCAGTGCCGACACCCAGGAG

AspMetAsnAlaTrpValArgAlaMetAsnGlnAlaAlaGlnValLeuSer
 817 GACATGAACGCTTGGGTCAGGGCCATGAACCAGGCTGCACAGGTGCTGTCT

ArgSerSerLeuLysArgAspMetGluLysValGluArgGlnAlaValPro
 868 CGATCGTCACTGAAGAGGGATATGGAGAAGGTGGAGCGGCAGGCTGTCCCC

GlnAlaAsnHisThrGluSerCysHisGluCysGlyArgValGlyProGly
 919 CAGGCCAACCACACAGAGTCCTGTCACGAATGTGGCCGGGTGGGACCCGGA

HisThrArgAspCysProHisArgGlyHisAspAspIleValAsnPheGlu
 970 CATACGAGAGATTGTCCTCATCGTGGCCATGATGACATTGTCAACTTCGAG

ArgGlnGluGlnGluGlyGluGlnTyrArgSerGlnArgAspProLeuGlu
1021 AGGCAGGAGCAGGAGGGAGAGCAGTACCGTTCCCAGAGGGACCCACTGGAG

GlyLysArgAspArgSerLysAlaArgSerProTyrSerProAlaGluGlu
1072 GGCAAGCGGGACCGGAGCAAGGCCAGGTCTCCGTACTCGCCAGCCGAGGAG

AspAlaLeuPheMetAsp    Pro    GlyProArg    GlnGlnAlaGln
1123 GATGCCTTGTTTATGGATT4ACCCAYTGGCCCAAGAGOCCAGCAGGCACAC

ProGlnArgAla    LysAsnGlyMetLeuPro        TyrGlyProGly
1174 CCCCAACGGGCAGA6AARAATGGAATGCTGCCTGCYT3ATATGGCCCAGGA

AsnGly    GlyGly    GlnArg    Phe    ProArgThrAsn
1225 6AACA6AATGGGA3TGGTGGGT5CCAGCGGGCYTTTCYTCCCAGGACCAAC

GluLysHisSerGlnArgLys    AsnLeuAlaGlnValGluHisTrp
1276 CYTGAAAAACACAGCCAAAGGAAGA6CAATCTGGCCCAGGTGGAGCACTGG

AlaArgAlaGlnLysGlyAspSerArgSerLeuProLeuAspGlnThr
1327 GCAAGGGCCCAGAAAGGGGATAGCAGGAGTCTTCCCTTGGACCAGACG3TT

ArgGlnGly    GlyGlnSerLeu    PheProGluAsnTyrGln
1378 C3TCGCCAGGGTC3TGGCCAATCCCTGTC3TTCCCAGAAAACTACCAGAYT

ProLysSerThrArgHisProSerGly       SerPro      ProArg
1429 YTTCCCAAGAGCACCCGACACCCCTCGGGGGGYTCYTCGCCACYTCCCCGA

AsnLeuProSerAspTyrLysTyrAlaGlnAspArgAlaSerHisLeu
1480 AACCTGCCAAGTGACTACAAGTATGCGCAGGACCGAGCCAGCCACCTGAA6
```

FIG. 4.(Page 2 of 6)

```
     MetSerSerGlu   Arg   GlyAlaProGlyTrpHisArgValAla
1531 ATGTCGAGTGAA6A6CGCCGXGGCGCACCGGGATGGCACCGTGTGGCAGYT

Leu      AlaAlaAlaProAlaValProAlaArgGlnProHisSerAla
1582 CTAC6A6TGGCAGCAGCGCCAGCAGTTCCGGCACGGCAGCCCCACAGCGCC

HisLeuProTrpLeuPro    ValHisArgProGlyProGluGlnGluHis
1633 CATCTGCCTTGGCTCCCCA6AGTTCACCGACCAGGGCCGGAGCAGGAGCAT

GlyAlaProLeuHis   CysAlaSer   Ser   GlnHis
1684 G3TA6AGGTGCCCCGCTCCATYT3TGTGCCTCCAT3TCCYT3GGACATCC3

SerProArgThrProLysGly   ProThrProAlaAlaThrHisThrSer
1735 TCCCCCAGGACCCCCAAGGGTYTTCCCACCCCGGCGGCCACACACACCAGC

Arg   Ser   SerGluAlaThrGlyPro   Glu   CysGlyHisLeu
1786 AGA6CGAGTC5CAGTGAAGCCACCGGACCA6ARGARGA6TGTGGACATCTC

ProGlyGlyPheSerMetGlyTyrMet   HisThrValSerAlaProSer
1837 CCTGGGGGATTCTCCATGGGTTACATGAJCCACACCGTCAGCGCTCCCAGT

LeuHisGlyLysSerAlaAspAspThrTyrLeuGlnLeu   Lys   Leu
1888 TTACATGGAAAATCGGCTGATGATACCTACCTCCAGCTGAA6AAARA7CTG

TyrLeuAspLeuLysMetThrGlyArgAspLeuLeuLysAspArgSer
1939 GA6TACCTGGATCTAAAGATGACAGGCCGGGACCTTCTCAAGGATCGAAGT

LeuLysProValLysIleAlaGluSerAspThrAspValLysLeuSerIle
1990 CTGAAGCCTGTGAAGATCGCTGAGAGCGACACTGACGTCAAACTGAGCATC

PheCysGluGlnAspArgValLeuGlnAspLeuGluAspLysIleArgAla
2041 TTCTGTGAACAAGACAGGGTCCTCCAGGACTTGGAAGACAAGATACGAGCC

LeuLysGluAsnLysAspGlnLeuGluSerValLeuGluValLeuHisArg
2092 CTTAAAGAGAACAAAGACCAGCTAGAATCTGTGCTGGAGGTGTTGCACAGA

GlnMetGluGlnTyrArgAspGlnProGlnHisLeuGluLysIleAlaTyr
2143 CAGATGGAGCAGTACCGAGACCAGCCCCAGCACTTGGAGAAGATTGCCTAC

GlnGlnLysLeuLeuGlnGluAspLeuValHisIleArgAlaGluLeuSer
2194 CAGCAGAAGTTGCTGCAGGAGGACCTTGTCCATATCCGAGCTGAGCTCTCC

ArgGluSerThrGluMetGluAsnAlaTrpAsnGluTyrLeuLysLeuGlu
2245 AGAGAGTCCACTGAGATGGAAAATGCTTGGAACGAATACCTGAAGTTGGAG
```

FIG. 4. (Page 3 of 6)

```
     AsnAspValGluGlnLeuLysGlnThrLeuGlnGluGlnHisArgArgAla
2296 AATGATGTGGAACAGCTGAAGCAGACCCTGCAGGAGCAACACAGAAGAGCC

PhePhePheGlnGluLysSerGlnIleGlnLysAspLeuTrpArgIleGlu
2347 TTTTTTTTCCAGGAGAAATCGCAGATACAGAAAGATCTATGGAGAATTGAA

AspValThrAlaGlyLeuSerAlaAsnLysGluAsnPheArgIleLeuVal
2398 GATGTCACTGCAGGCCTGAGTGCAAATAAAGAGAACTTCAGAATTCTAGTG

GluSerValLysAsnProGluArgLysThrValProLeuPheProHisPro
2449 GAGTCAGTAAAAAATCCGGAGAGAAAAACGGTGCCTTTGTTTCCTCACCCG

ProValProSerLeuSerThrSerGluSerLysProProProGlnProSer
2500 CCTGTGCCTTCACTCTCAACTTCTGAGAGCAAGCCGCCCCCACAGCCCAGT

ProProThrSerProValArgThrProLeuGluValArgLeuPheProGln
2551 CCTCCCACCAGCCCTGTGCGGACCCCTCTGGAGGTTCGACTCTTCCCCCAG

LeuGlnThrTyrValProTyrArgProHisProProGlnLeuArgLysVal
2602 CTGCAAACCTACGTGCCGTACCGACCTCACCCACCCCAGCTGAGGAAAGTG

ThrSerProLeuGlnSerProThrLysAlaLysProLysValGlnGluAsp
2653 ACATCCCCCCTTCAGTCACCAACTAAGGCGAAGCCCAAAGTTCAGGAAGAT

GluAlaProProArgProProLeuProGluLeuTyrSerProGluAspGln
2704 GAAGCACCTCCCAGGCCCCCACTCCCCGAACTCTACAGCCCAGAGGACCAG

ProProAlaValProProLeuProArgGluAlaThrIleIleArgHisThr
2755 CCCCCGGCTGTGCCGCCTCTGCCAAGAGAGGCCACCATCATCCGGCACACA

SerValArgGlyLeuLysArgGlnSerAspGluArgLysArgAspArgGlu
2806 TCTGTGCGGGGCCTCAAGCGGCAGTCAGACGAGAGGAAGCGAGACCGGGAG

LeuGlyGlnCysValAsnGlyAspSerArgValGluLeuArgSerTyrVal
2857 CTGGGGCAGTGTGTGAATGGGGATTCCAGGGTGGAGCTGCGGTCGTATGTC

SerGluProGluLeuAlaThrLeuSerGlyAspMetAlaGlnProSerLeu
2908 AGTGAGCCTGAGCTGGCGACCCTCAGCGGGGACATGGCCCAGCCCTCCCTA

GlyLeuValGlyProGluSerArgTyrGlnThrLeuProGlyArgGlyLeu
2959 GGACTTGTGGGCCCTGAGAGCAGGTACCAGACGCTGCCAGGCAGAGGGCTC

SerGlySerThrSerArgLeuGlnGlnSerSerThrIleAlaProTyrVal
3010 TCAGGGTCCACGTCAAGGCTCCAGCAGTCGTCCACCATTGCTCCCTACGTC
```

FIG. 4. (Page 4 of 6)

```
         ThrLeuArgArgGlyLeuAsnAlaGluSerSerLysAlaThrPheProArg
    3061 ACACTCCGGAGGGGTCTCAATGCCGAAAGCAGCAAGGCGACCTTCCCTAGA

ProLysSerAlaLeuGluArgLeuTyrSerGlyAspHisGlnArgGlyLys
    3112 CCTAAGAGTGCCTTGGAGCGCCTGTACTCAGGGGATCACCAGCGAGGCAAG

MetSerAlaGluGluGlnLeuGluArgMetLysArgHisGlnLysAlaLeu
    3163 ATGAGTGCAGAGGAGCAGCTGGAGCGCATGAAGCGACACCAGAAGGCCCTG

ValArgGluArgLysArgThrLeuGlyGlnGlyGluArgThrGlyLeuPro
    3214 GTCCGAGAGCGCAAGAGGACACTGGGCCAAGGGGAGAGGACGGGCCTGCCC

SerSerArgTyrLeuSerArgProLeuProGlyAspLeuGlySerValCys
    3265 TCATCTCGCTACCTCAGCCGGCCGCTCCCTGGAGATCTTGGCTCAGTATGT

---
    3316 TAGGAGGGGCCAGGCAGCGGGGCAGGGACAGGGAGCCGAGTGCCCCTCAGA
    3367 GTCCCCCAAACACAAGCACATCACACCTCCCAGTGAGAGAGCTGTCCATTG
    3418 ACCTACATGGTTCAGAGAACACCCCACGGGGCTGTTTGTCCACGACCCAGG
    3469 CTGGACGAATGCCTGGTCAGAGGGTGACCTGAACCAGAGCTGGAGTGAGGA
    3520 TCAAACAGGCCCAGGAGCCTGAGGAAATACCCAGTCAGTCCTCCCAGCCGC
    3571 GATGGAGAGGGGCCTTTGCAGGCGTTCGGAATCTCGGCTGAATTCAGGACC
    3622 TGGGAATACAGGGTTCAGAGAGGAGAGGAGGAAGATGGTGACATGATTTGG
    3673 TTAGAAGCACAAGCAAACTGATCAGCCTCCCAGACCTGCCAGCAGATGCTG
    3724 TGTGAGGGTGATGGAGCACGGGGTCACACCCCTGCCCCAAGGGCCACTGGT
    3775 CTCCCTGGGCTTGCAGTGCAGAGGCCTCAGGGTGTCTGGGATTGCTGGGGA
    3826 GG9CTGTGCTGCCCCCTGGTGGCGCTTCCTGGCGCTGCGCCCTGTCCACAG
    3877 TCACCTTAGGACCCTTTGGAAACATTCCATTTGACTTTTCCTGTTGYTTG
    3928 AAATCCCATGTTTCCCTAAACCTCTAGCCTGATTGTTCTTTCCCTAATTCA
    3979 TTGCACAAGCTCCTTTGCTTTTAGTGTTACCGCTCATTGCCTCTCTAATCC
    4030 TGCCTGATTGTGTTTACAGAAGCTTCTGATTTGCATTGAACATGCTCTAAC
    4081 TGGCCTGTGCTACTTATTACCGGGCTTGTAATAGCGGTTCTTGTCTCCATA
    4132 GCCTGTTGAGTGTTCCCAGATGTGACTCACCTTTCTGCTGCCCTCTTCATG
    4183 CAGGCCTACTGACTCATAATTCACTTGTCCGTCGACGCGGCCGCGAATTC
```

CODE    MEANING
----    -------
ANY CODES NOT LISTED BELOW MATCHES A,C,G,OR T (ANY BASE)
1       A, C, G, OR T (ANY BASE)
2       A, C, G, OR T (ANY BASE)
3       PROBABLY CYTOSINE
4       PROBABLY THYMINE
5       PROBABLY ADENINE
6       PROBABLY GUANINE

FIG. 4. (Page 5 of 6)

```
7       MAYBE CYTOSINE
8       MAYBE THYMINE
9       MAYBE ADENINE
0       MAYBE GUANINE
A       ADENINE
B       C IF PRECEDED (5'-3') BY T; G IF PRECEDED BY A
C       CYTOSINE
D       C OR T IF FOLLOWED (5'-3') BY AA; ANY BASE IF
        FOLLOWED BY AG
E       C OR T IF FOLLOWED (5'-3') BY CT; ANY BASE IF
        FOLLOWED BY CG
F       A OR G IF FOLLOWED (5'-3') BY CT; ANY BASE IF
        FOLLOWED BY GA
G       GUANINE
H       A, C, OR G (NOT T)
I       A OR G IF PRECEDED (5'-3') BY TT; ANY BASE IF
        PRECEDED BY CT
J       A OR C
K       G OR T
L       A OR T
M       C OR G
N       A, C, G, OR T (ANY BASE)
O       A, C, G, OR T (ANY BASE)
P       A OR G IF PRECEDED (5'-3') BY AG; ANY BASE IF
        PRECEDED BY CG
Q       A, C, OR T (NOT G)
R       A OR G
S       C, G, OR T (NOT A)
T       THYMINE
U       A, C, G, OR T (ANY BASE)
V       C OR T IF PLRECEDED (5'-3') BY AG; ANY BASE IF
        PRECEDED BY TC
W       A, G, OR T (NOT C)
X       A NUCLEOTIDE THAT HAS BEEN ARBITRARILY ADDED TO JOIN
        READING FRAMES.
Y       C OR T
Z       C IF FOLLOWED (5'-3') BY T; G IF FOLLOWED BY A

COMPLEMENTARY CODES:
1234567890ABCDEFGHIJKLMNOPQRSTUVWXYZ
1265430987TZGIPVCSDKJLMNOEWYHAAFQXRB
```

FIG. 4. (Page 6 of 6)

```
  1 GGAAACGCAGTTTAAAACTCCAGCCCAGGCCCCGTCGCGCGTAGATGGCAG

ProAspProValGlnThrGlnLeu
 52 CGGAGGCGGCGGCGCGGGCCGGGGTGACCAGATCCCGTTCAAACTCAGCTG

ProProSerAlaProPheLeuSerGlyGeuArgPheCysThrAsnPhePro
103 CCACCAAGTGCGCCTTTTCTCTCTGGATTGCGATTCTGCACGAATTTTCCA

ValGluGlyGlySerAlaLeuSerGlnProLeuProSerLysThrArgPro
154 GTTGAGGGTGGTTCGGCGCTCAGCCAGCCTCTGCCCTCGAAGACGCGGCCT

***
    TrpSerArgAsnLeuGlnAlaAspAlaAlaMetGlnHisTyrGlyValAsn
205 TGGTCTAGGAACCTTCAGGCGGATGCCGCCATGCAGCACTACGGGGTGAAC

GlyTyrSerLeuHisAlaMetAsnSerLeuSerAlaMetTyrAsnLeuHis
256 GGCTACTCACTGCACGCCATGAACTCACTCAGCGCCATGTACAACCTGCAC

GlnGlnAlaAlaGlnGlnAlaGlnHisAlaProAspTyrArgProSerVal
307 CAGCAGGCAGCCCAGCAGGCCCAGCATGCCCCCGACTACCGGCCTTCAGTG

HisAlaLeuThrLeuAlaGluArgLeuAlaGlyCysThrPheGlnAspIle
358 CATGCGCTTACATTGGCTGAGCGCCTGGCTGGCTGTACATTTCAAGACATC

IleLeuGluAlaArgTyrGlySerGlnHisArgLysGlnArgArgSerArg
409 ATCTTGGAGGCCCGTTATGGTTCCCAGCACCGCAAACAACGTCGCAGCCGC

ThrAlaPheThrAlaGlnGlnLeuGluAlaLeuGluLysThrPheGlnLys
460 ACAGCGTTCACGGCTCAGCAGCTCGAGGCCCTGGAAAAGACCTTCCAGAAG

ThrHisTyrProAspValValMetArgGluArgLeuAlaMetCysThrAsn
511 ACTCACTACCCAGATGTGGTGATGCGTGAGAGGCTGGCCATGTGCACCAAC

LeuProGluAlaArgValGlnValTrpPheLysAsnArgArgAlaLysPhe
562 CTGCCTGAGGCCCGGGTGCAGGTGTGGTTCAAGAACCGCCGGGCCAAGTTC

ArgLysLysGlnArgSerLeuGlnLysGluGlnLeuGlnLysGlnLysGlu
613 CGGAAGAAGCAGCGTAGCCTGCAGAAGGAACAGCTCCAGAAGCAGAAGGAG

AlaGluGlySerHisGlyGluGlyLysAlaGluAlaProThrProAspThr
664 GCTGAGGGCTCCCATGGGGAAGGCAAGGCCGAGGCCCCCACTCCAGATACC

GlnLeuAspThrGluGlnProProArgLeuProGlySerAspProProAla
715 CAGCTGGACACTGAGCAGCCCCCACGTCTGCCTGGCAGCGACCCCCCTGCT
```

FIG. 6. (Page 1 of 4)

```
        GluLeuHisLeuSerLeuSerGluGlnSerAlaSerGluSerAlaProGlu
  766   GAGCTTCACCTGAGTCTGTCTGAGCAGTCAGCCAGTGAGTCAGCCCCTGAG

AspGlnProAspArgGluGluAspProArgAlaGlyAlaGluAspProLys
  817   GATCAGCCGGACCGTGAGGAGGACCCCAGGGCAGGGGCTGAGGACCCCAAA

AlaGluLysSerProGlyAlaAspSerLysGlyLeuGlyCysLysArgGly
  868   GCTGAGAAGAGCCCTGGGGCTGACAGCAAGGGGCTGGGCTGCAAGAGGGGC

SerProLysAlaAspSerProGlySerLeuThrIleThrProValAlaPro
  919   AGCCCCAAGGCAGATTCCCCAGGCAGCCTGACCATCACTCCTGTGGCCCCA

GlyGlyGlyLeuLeuGlyProSerHisSerTyrSerSerSerProLeuSer
  970   GGGGGTGGCCTCCTGGGCCCTCCCACTCCTATTCCTCGTCCCCGCTGAGC

LeuPheArgLeuGlnGluGlnPheArgGlnHisMetAlaAlaThrAsnAsn
 1021   CTCTTCCGTCTGCAGGAGCAATTCCGCCAGCATATGGCGGCCACCAACAAC

LeuValHisTyrSerSerPheGluValGlyGlyProAlaProAlaAlaAla
 1072   CTGGTGCACTACTCGTCCTTCGAAGTAGGGGGTCCGGCCCCTGCTGCTGCA

AlaAlaAlaAlaAlaValProTyrLeuGlyValAsnMetAlaProLeuGly
 1123   GCGGCGGCTGCTGCTGTGCCCTACCTGGGCGTCAACATGGCCCCGCTGGGC

SerLeuHisCysGlnSerTyrTyrGlnSerLeuSerAlaAlaAlaAlaAla
 1174   TCACTGCACTGCCAGTCCTACTACCAGTCCCTGTCAGCAGCCGCTGCTGCC

HisGlnGlyValTrpGlySerProLeuLeuProAlaProProAlaGlyLeu
 1225   CACCAGGGTGTGTGGGGGTCTCCTCTGCTGCCTGCACCCCCAGCAGGCCTG

AlaProAlaSerAlaThrLeuAsnSerLysThrThrSerIleGluAsnLeu
 1276   GCTCCTGCATCAGCTACCCTGAACAGTAAAACCACAAGCATCGAGAACCTG

ArgLeuArgAlaLysGlnHisAlaAlaSerLeuGlyLeuAspThrLeuPro
 1327   CGGCTCCGGGCCAAGCAGCACGCGGCCTCCCTGGGACTCGATACGCTGCCC

Asn---
 1378   AACTGACTGTCTGGCTTCCAACCCAGCCAGGGGTCTTAGGTGTCCCCTCCT
 1429   AGCCCTGTGGTTATCCCTAGGTGGCTCTCGAGGAGTTAACTCCATGAGCCC
 1480   AGGGATCCTAGGGCCTGGGGTCCTGTTCCCTGCTCCGCTTCCCCATACCCC
 1531   AGCCCGAGGTGAAGCCCACACCTACACACCCTCTGCATGGCCCTGCCTGGA
 1582   CCCCATGGAGGCCGAATAGGGAGGAGGTGAGAGGCTGGGGTGCCCCAAGCT
 1633   TCCCTCGGAGAAGTGAGAGGCTCTCCCTGGCTAGATCCTCATCTCAATAGC
```

FIG. 6. (Page 2 of 4)

```
1684 ACCTCCTCCCTTTTCTCCCTATCCTTCTGCCCCCTAGTAAGTCTACGTGTG
1735 GAATGTGAGATATAAATATAAATATATAAAGCTATATTTTCAGGCTCCTGC
1786 CTGCCCCAGGCCCCCTGCCCCACTCCATCTCTTCTTCCCTGCCACCCCTC
1837 CCTGCAGCCTCCGCGGCTCACTCCAGCCATCCCTTCTGTTTCTCCTTCTCT
1888 CTCCTTCCTTCTTCCCTTGATCTCCCTCTTCCTGTCTCTGTCCTGGTCCCT
1939 GCCCCGTCTCGGCCCAGCCTCTGTATTCTCCACCCTTGATCTTTCTCCTT
1990 GTCTCTCCCGCTGCCCCTGGTTTCTTCCTTTGGTGTTGGCTGTGTTGGTAT
2041 CATCAGTTCTTGAGCTATATTTTGTTTGGGGTTGTGGCTGGTTTTGGTTTT
2092 AGTAATTTTGCGACTTCCCGTTGCTCTCCTTCTATTCCCTTCCTTCTGCCC
2143 TGCCTGCCTCCCTGCACCTGCGGCCTCTCTAGGAAGCTGTTCCTTTCTATG
2194 CCCAATAGAAGCAACAAGGCCCTAGCTGGAGACTCTGGGGATCTGGAGCTG
2245 CAGGCAGGAGGTGGCACTGGCTCCCACTCCCACCCCTGCCCAGGCTGGCAT
2296 CTAGAAGGCGTCATGAATTACTTTCTCTTCTCTCTTCTCAATTTTGAGGTC
2347 CTCATTCCCAAGATTGAGGAGGCAGTAGTTAATCTGGGAAGGCAGTAGAAT
2398 GGCCAGCATTCCTGCCTGTAAGTCTTCCCAAGACAGAGGCCTGGTGACACA
2449 GTTCAGCCAGGACTGACCACAGGGCTCTAGAGCTCTCTTTGGTGAGACTTC
2500 CCTGGATGGAGAGCAGCAGCAGGGGAAGAGGTGCTCTCAGAGACAGCAGGG
2551 CTGGTGCTCTTCTCCCACAAGCTGAGCTCCACGTTCAGCAGATACTGTCCA
2602 AGGCAGGGGTACGGCTGACCAGGAATGAAGGTTGAACTCTGCTCCTGAGCA
2653 CGGTGCGTGCAAAGCATATAGCAGCACATAGGCTCAGGCTTCTGTAGGCTT
2704 CCTGTCCCAGAGCCAATTATGGAAGTAAGGGCTTCCCTCCAGCTAGTCACT
2755 GGAATGGAAAAGTGTGTGTCCTGTTCATAGCCAGGAAACCCAGCTCAGCAA
2806 ACTCCCTTTCAAAGCTGTGTGACCGGCTGGGCATGGTGGCTCACACCTGTA
2857 ATCCCAGCACTTTGGGAGGCCAAGGCAGGCAATCACCTGAGGTCAGGAGTT
2908 CAAGACCAGCCTGGCTAACATGTGAAACTAATAATAATACAAAAATTAGCT
2959 GGGCGTGGTGGCACATGCCTGTAATCCCAGCTACTTGGGAGGCTGAGTTGG
3010 GAGGATTGCTGCAATCTGGGAGGTGGAAGTTGCAGTGAGCCGAGATCATGA
3061 CACTGCACTCCAGCCTGGGCGACGGAGTGAGACTCCATCTCAAAAAAAAA
3112 AAAATAAAAATAAAAGCTGTGTGACCTTGGGCAASCCTGTAGCCTCTCTGG
3163 GTCTGTTTCCCTGTCTGGGTTAAATGGCCTGTAAGGTCCTAGCCAGCTCTA
3214 CATTCTGCATTTGCTCGCAACCTTGTAACACAGAAGTTTTTAGTTAAATTG
3265 ACAACAGAAGGTTCTCAAAAGCACAATATATGAAGTAGGAAATTACTATTG
3316 CCTTTCTGTGGAGCAAGGGGTGTTGTACACACAAGCCTCACTGTAGACACT
3367 GCCTCAGTTTCCCCATAGGCATAATGGGTCCCTTCTAGTTCAGGCAATCTG
3418 GATTTGATCTTGAGTTCCAGTGCCAGCCTCTGGAGTCACTCCATTTTCATA
3469 CCTTTTCATGATCTCAGGGGCTCTGGGCAGTGGGAGGTGATGGCTTGGACA
3520 GATTCTTGGTCATGCTCCCAACTCTTGGTGGCTCACCACTGAACACTCCA
3571 AACCCTGCTTAAAGAAGTTGATTTATTTGAAAGCCAGGGTAAAGATTGCTA
3622 AGGCTTGTCTCCTCTCCCAGTGGGAAGAGAGAGGTTCTGTTGGTGTCCTGG
3673 TTGAATTGCTTTGCAGAGAAGTCAATGCCCATCACCCTTGATGGGGTCAG
3724 CCTAGGCTGGGGCAGATGGAGAAGGCTTTGGACAGGAAAAAGTGAGCAGG
3775 ATGGTAGTCTAGGCCAGGAGAAGTGTTTGAACAAAGCAGCAGAGATGAGAC
3826 TCAGTAGACCATGGGAAGGGGGTGGCTGGCTTCACGAGAGGTGGGGGCTAA
```

FIG. 6. (Page 3 of 4)

```
3877 GGGGCCTGGAATCCAGGCTAAAGACCACACCTACATGTGGCAAGCACCAAG
3928 ACAGGCATTTGAGGGTTTCCAAATCCTCAGGTCTCTTGCTGGGGTCTGGAA
3979 TTTGGAAGGGGAATCCACCAGCCATGGGGGCATCAGAGGAGAGACTTAGGC
4030 AGCGCTGTGGGAGGTTGGCAGATTCCAGGAGTGACAGAGGAGGTTTTTGGT
```

FIG. 6. *(Page 4 of 4)*

```
  1 CTGCAGAGGATAGAAAAAAG0CCCTCTGATACCTCAAGTTAGTTTCACCTTTA
    -PST1-

54 AAGAAGGTCGGAAGTAAAGACGCAAAGCCTTTCCCGGACGTGCGGAAGGGCAA

107 CGTCCTTCCTCATGGCCGGAAATGGAACTTTAATTTCCCGTTCCCCCCAACCA

160 GCCCGCCCGAGAGAGTGACTCTCACGAGAGCCGCGAGAGTCAGCTTGGCCAAT

213 CCGTGCGGTCGGCGGCCGCTCCCTTTATAAGCCGACTCGCCCGGCAGCGCACC

****************************************************
266 GGGTTGCGGAGGGTGGGCCTGGGAGGGGTGGTGGCCATTTTTTGTCTAACCCT

****************************************************
319 AACTGAGAAGGGCGTAGGCGCCGTGCTTTTGCTCCCCGCGCGCTGTTTTTCTC

****************************************************
372 GCTGACTTTCAGCGGGCGGAAAAGCCTCGGCCTGCCGCCTTCCACCGTTCATT

****************************************************
425 CTAGAGCAAACAAAAAATGTCAGCTGCTGGCCCGTTCGCCCCTCCCGGGGACC hTR
    ****************************************************
478 TGCGGCGGGTCGCCTGCCCAGCCCCCGAACCCCGCCTGGAGGCCGCGGTCGGC

****************************************************
531 CCGGGGCTTCTCCGGAGGCACCCACTGCCACCGCGAAGAGTTGGGCTCTGTCA

****************************************************
584 GCCGCGGGTCTCTCGGGGGCGAGGGCGAGGTTCAGGCCTTTCAGGCCGCAGGA

****************************************************
637 AGAGGAACGGAGCGAGTCCCCGCGCGCGGCGCGATTCCCTGAGCTGTGGGACG

*************************>
690 TGCACCCAGGACTCGGCTCACACATGCAGTTCGCTTTCCTGTTGGTGGGGGGA

743 ACGCCGATCGTGCGCATCCGTCACCCCTCGCCGGCAGTGGGGGCTTGTGAACC

796 CCCAAACCTGACTGACTGGGCCAGTGTGCTGCAAATTGGCAGGAGACGTGAAG

849 GCACCTCCAAAGTCGGCCAAAATGAATGGGCAGTGAGCCGGGGTTGCCTGGAG
```

FIG. 9. (Page 1 of 2)

```
902 CCGTTCCTGCGTGGGTTCTCCCGTCTTCCGCTTTTTGTTGCCTTTTATGGTTG

955 TATTACAACTTAGTTCCTGCTCTGCAG
                -PST1-
```

FIG. 9. (Page 2 of 2)

PEPTIDES RELATED TO TPC2 AND TPC3, TWO PROTEINS THAT ARE COEXPRESSED WITH TELOMERASE ACTIVITY

CROSS-REFERENCE TO RELATED APPLICATIONS

This application continuation application of U.S. patent application Ser. No. 08/710,249, filed Sep. 13, 1996, now U.S. Pat. No. 5,858,777, which is a continuation-in-part of U.S. patent application Ser. No. 08/583,808, filed Jan. 5, 1996, now abandoned, and claims the benefit of Provisional Application No. 60/003,492, filed Sep. 9, 1995, each of which are incorporated herein by reference.

FIELD OF THE INVENTION

The present invention provides methods and reagents for regulating telomere length and modulating telomerase activity in mammalian cells as well as for detecting, diagnosing, and treating related diseases and conditions in humans and other mammals. In an important embodiment, the invention provides oligonucleotide probes and primers, polynucleotide plasmids, peptides, proteins, antibodies, and enzymes relating to genes and gene products that regulate telomere length and telomerase activity in mammalian cells. The invention has diverse applications and provides important advances in the fields of molecular biology, chemistry, pharmacology, and medical therapeutic and diagnostic technology.

BACKGROUND OF THE INVENTION

The DNA at the ends of the telomeres of chromosomes in mammalian cells consists of double- and single-stranded nucleic acid composed of many tandem repeats of a simple nucleotide sequence referred to as the telomeric repeat sequence. Telomeres help maintain chromosome structure and function; the loss of telomeric DNA can activate the cellular processes that detect and control DNA damage and monitor and control cell proliferation and senescence. The maintenance of telomeres and the regulation of telomere length are vital cellular functions involved in transmitting genetic information from generation to generation, aging, the control of cell growth, and cancer. See Harley, 1991, *Mutation Research* 256:271–282; and Blackburn, 1992, *Annu. Rev. Biocheni.* 61:113–129, each of which is incorporated herein by reference (note: references cited herein are provided for convenience; such citations are not to be construed as an admission of prior invention).

The multi-component telomerase ribonucleoprotein enzyme catalyzes the synthesis of the first strand of telomeric DNA synthesized during telomere elongation, using the RNA component of the enzyme as a template. Although the RNA component of human telomerase (hTR) and other mammalian telomerase enzymes has been identified, isolated, characterized, and described in the scientific literature, the protein components of the telomerase enzyme as well as most other cellular macromolecules involved in telomere maintenance and the regulation of telomere length and telomerase activity in mammalian cells have not. See Feng et al., 1995, *Science* 269:1236–1241; PCT patent publication No. 96/01835; and pending U.S. patent application Ser. No. 08/521,634, filed Aug. 31, 1995, and Ser. No. 08/330,123, filed Oct. 27, 1994, each of which is incorporated herein by reference.

Many useful methods and reagents relating to telomere and telomerase biology have been described. See, e.g., U.S. Pat. No. 5,489,508; PCT patent publication Nos. 95/23572, 95/13381, 95/13382, and 95/13383; and U.S. patent application Ser. No. 08/632,662, filed Apr. 15, 1996, each of which is incorporated herein by reference. Significant improvements to and new opportunities for telomere- and telomerase-mediated therapies as well as related assays, screens, diagnostic methods, and reagents could be realized and obtained, however, if additional cellular macromolecules involved in mammalian telomere maintenance and the regulation of telomere length and telomerase activity could be identified, characterized, and made available in pure or isolatable form. In particular, the characterization of the nucleotide and corresponding amino acid sequences of such macromolecules could provide new and useful recombinant expression vectors and plasmids, as well as related reagents useful in medical therapeutic and diagnostic technology.

SUMMARY OF THE INVENTION

The present invention provides methods and reagents for regulating telomere length and modulating telomerase activity in mammalian cells as well as for detecting, diagnosing, and treating related diseases and conditions in humans and other mammals.

In one embodiment, the invention provides recombinant mammalian host cells containing:

(i) a recombinant or synthetic nucleic acid comprising at least about 10 to 15 to 25 to 100 or more contiguous nucleotides corresponding to an open reading frame sequence of a human gene TPC2 contained in a human DNA insert of an ~3.5 kb NotI-BstEII restriction fragment of plasmid pGRN109 (on deposit with the American Type Culture Collection under the accession number ATCC 97708); or a synthetic or recombinant peptide or protein comprising at least about 6 to 10 to 15 to 25 to 100 or more contiguous amino acids corresponding to an amino acid sequence encoded by said open reading frame sequence; and (ii) a recombinant or synthetic nucleic acid comprising at least about 10 to 15 to 25 to 100 or more contiguous nucleotides corresponding to an open reading frame sequence of a human gene TPC3 contained in a human DNA insert of an ~1.4 kb EcoRI-BamHI restriction fragment of plasmid pGRN92 (ATCC 97707); or a synthetic or recombinant peptide or protein comprising at least about 6 to 10 to 15 to 25 to 100 or more contiguous amino acids corresponding to an amino acid sequence encoded by said open reading frame sequence of gene TPC3;

said TPC2 and TPC3 genes characterized in coding for proteins that regulate telomere length or modulate telomerase activity and are present in human or other mammalian cells that express telomerase activity.

Other mammalian host cells provided by the invention include those that comprise either or both TPC2- and TPC3-derived recombinant or synthetic nucleic acids, peptides, or proteins. Furthermore, the invention also provides such cells further modified to contain a synthetic or recombinant nucleic acid comprising at least about 10 to 15 to 25 to 100 or more contiguous nucleotides corresponding to a contiguous nucleotide sequence of human hTR located in an ~2.5 kb HindIII-SacI restriction fragment of pGRN33 (ATCC 75926).

The recombinant host cells of the invention have application in many useful methods also provided by the invention. For example, the invention provides recombinant host cells comprising novel expression vectors with expression control sequences operatively linked to nucleotide sequences encoding amino acids in a sequence substantially identical to the amino acid sequences encoded by the human TPC2 or TPC3 genes and, optionally, a recombinant hTR gene. These recombinant host cells are useful for producing recombinant human telomerase, for use in screens to identify agents that modulate telomerase activity or regulate telomere length, as well as for a variety of other purposes described more fully below. The recombinant host cells of the invention can also be incorporated into the germ line and/or somatic tissues of non-human transgenic mammals, as well as be administered to mammals for therapeutic purposes.

In another embodiment, the invention provides synthetic and recombinant oligonucleotides and nucleic acids in a variety of forms, i.e., isolatable, isolated, purified, or substantially pure, and for a variety of purposes, i.e., as probes or primers, as polynucleotide plasmids and vectors for introducing recombinant gene products that regulate telomere length or modulate telomerase activity in mammalian host cells, as restriction fragments for creating useful nucleic acids, and as reagents for therapeutic, diagnostic, and other applications. In particular, the invention provides recombinant or synthetic nucleic acids comprising at least about 10 to 15 to 25 to 100 or more contiguous nucleotides substantially identical or complementary in sequence to a contiguous nucleotide sequence located in either:

(i) an open reading frame sequence of a human gene TPC2 contained in a human DNA insert of an ~3.5 kb NotI-BstEII restriction fragment of plasmid pGRN109; or (ii) an open reading frame sequence of a human gene TPC3 contained in a human DNA insert of an ~1.4 kb EcoRI-BamHI restriction fragment of plasmid pGRN92.

The novel oligonucleotide probes and primers of the invention typically comprise nucleotides in a sequence substantially identical or complementary to a sequence of nucleotides in a TPC2 or TPC3 gene or gene product to allow specific hybridization thereto in a complex mixture of nucleic acids. Such probes and primers therefore have useful application in a variety of diagnostic, therapeutic, and other applications.

The expression vectors of the invention typically comprise expression control sequences operatively linked to a nucleotide sequence encoding amino acids in a sequence identical to a sequence of amino acids in a TPC2 or TPC3 protein gene product. Such expression vectors have many useful applications, including in therapeutic methods of the invention as gene therapy vectors for modulating telomerase activity, either to activate or inhibit that activity, or for regulating telomere length, either to increase or decrease the length, in a target cell or tissue.

Gene therapy expression vectors of the invention also include those that encode variants or "muteins" of the TPC2 and/or TPC3 proteins, i.e., express proteins that differ from TPC2 and/or TPC3 by deletion, substitution, and/or addition of one or more amino acids. The gene therapy vectors of the invention may also, however, encode useful nucleic acids, such as hTR, or antisense nucleic acids or ribozymes that target the TPC2, TPC3, and/or hTR gene products, i.e., mRNA and telomerase RNA. Such vectors are useful in the therapeutic methods of the invention for treating or preventing diseases or conditions in which modulation of telomerase activity or telomere length can be of benefit. For example, in telomerase positive cancer cells, inhibition of telomerase activity can prevent telomere maintenance in those cells, inducing upon continued proliferation telomere loss, cell crisis, and death. For such purposes, the gene therapy vectors of the invention that express a non-functional TPC2 or TPC3 mutein or variant protein or other nucleic acid that can inhibit telomerase formation or telomere elongation by telomerase activity in the cell, such as by competing for RNA component or protein components, inhibition of endogenous gene expression, or other means, are preferred.

In another embodiment, the present invention provides peptides, proteins, antibodies, and enzymes, relating to genes and gene products that regulate telomere length and telomerase activity in mammalian cells. In particular, the invention provides synthetic or recombinant peptides or proteins comprising at least about 6 to 10 to 15 to 25 to 100 or more contiguous amino acids identical in sequence to an amino acid sequence encoded by an open reading frame sequence of a human gene located in either:

(i) an 3.5 kb NotI-BstEII restriction fragment of plasmid pGRN109; or (ii) an ~1.4 kb EcoRI-BamHI restriction fragment of plasmid pGRN92.

The present invention provides the proteins encoded by the TPC2 and TPC3 genes in isolatable form from host cells expressing recombinant TPC2 and/or TPC3 protein, as well as in purified and substantially pure form from synthesis in vitro or by purification from recombinant host cells or by purification of the naturally occurring proteins using antibodies or other reagents of the invention. Such proteins have application in methods for reconstituting in vitro telomerase or other enzymatic activities that maintain telomeres and regulate telomere length. These methods in turn have application in screens for therapeutic agents, for diagnostic tests, and for other applications. In addition, peptides corresponding to the amino acid sequences of TPC2 or TPC3 proteins can also be used to regulate telomere length and telomerase activity in mammalian cells.

The proteins and peptides of the invention can also be used to generate antibodies specific for TPC2 or TPC3 proteins or for particular epitopes on those proteins. Thus the invention provides polyclonal and monoclonal antibodies that specifically bind to TPC2 or TPC3 proteins. These antibodies can in turn be used to isolate TPC2 or TPC3 proteins from normal or recombinant cells and so can be used to purify the proteins as well as other proteins associated therewith. These antibodies also have important application in the detection of cells comprising TPC2 or TPC3 proteins in complex mixtures of cells. Such detection methods have application in screening, diagnosing, and monitoring diseases and other conditions, such as cancer, pregnancy, or fertility, because the TPC2 and TPC3 proteins are present in most cells capable of elongating telomeric DNA and expressing telomerase activity.

The immunogenic peptides and proteins of the invention can also be used in therapeutic immunization and vaccination procedures. See U.S. provisional patent application Ser. No. 60/008,949, filed Oct. 20, 1995, incorporated herein by reference. The invention provides a method of immunizing a subject, as well as vaccines useful in the method, against cells that maintain telomeres and express telomerase activity that comprises administering an immnunostimulating amount of such peptides or proteins of the invention.

In another embodiment, the invention provides a subtraction hybridization differential display method to identify, isolate, and clone expressed sequence tags (ESTs) of mRNA species encoding rare proteins, such as those involved in telomere elongation and the regulation of telomere length and telomerase activity. This method comprises the steps of:

(i) obtaining mRNA from a first population of mammalian cells which contain said rare protein, i.e., a protein component of telomerase, and from a second population of mammalian cells which do not contain said rare protein;

(ii) subjecting such mRNA to reverse-transcription and second-strand synthesis to form first and second cDNA preparations, said first and second cDNA preparations differing from one another with respect to presence or absence of cDNA molecules encoding said rare protein and a label incorporated into one of said first and second cDNA preparations;

(iii) combining said cDNA preparations under conditions such that complementary strands of cDNA from said first and second cDNA preparations anneal to form a mixture of double-stranded and single-stranded cDNA; and (iv) separating cDNA comprising said label from cDNA that does not, thereby forming an isolated preparation of cDNA from said first population that has been depleted from complementary cDNA in said second population and enriched for said cDNA encoding said rare protein. Steps (iii) and (iv) of the above method can be repeated as often as desired, and the cDNA isolated after completion of step (iv) can be amplified by PCR, to provide cDNA preparations greatly enriched for the desired cDNA.

These and other embodiments of the invention will be described in detail below.

BRIEF DESCRIPTION OF THE DRAWINGS

FIG. 1, in parts A, B, and C, is a bar graph showing the results of RT-PCR analysis using primers specific for TPC2 (FIG. 1A) or TPC3 (FIG. 1B) cDNA. In this and the other bar graphs, the number over each bar is the numerical result obtained; for RT-PCR results, this number was generated by scanning autoradiograms or PhosphorImager™ screens (Molecular Dynamics) of the RT-PCR products after gel electrophoresis. Under these test conditions, TPC2 and TPC3 mRNA is absent or detectable only at very low levels in the telomerase negative cell lines tested (labeled "Mortal" in the Figure) and detectable in all (most at clearly detectable levels) telomerase positive cell lines tested (labeled "Immortal" in the Figure).

FIG. 2, in parts A, B, and C, is a bar graph showing the results of an RT-PCR analysis of hTR RNA and TPC2 and TPC3 mRNA levels as well as telomerase activity in a variety of cell lines. FIG. 2B shows how TPC3 mRNA levels correlate with telomerase activity (as measured using the TRAP assay) in a variety of cell lines. The IMR90, HTB-153, WI-38 VA13, KMSF, and T0 (unactivated T cells; note that T7 represents activated T cells) express no or only very low levels of telomerase activity.

FIG. 4 lists portions of the nucleotide sequence (SEQ ID NO: 1) and deduced amino acid sequence (SEQ ID NO: 2) of the TPC2 open reading frame corresponding to the human TPC2 gene, mRNA, and protein products. In the Figure, as well as throughout the specification and Figures, nucleotides and amino acids are represented using standard abbreviations and designations; however, ambiguous nucleotides are represented as shown in the key at the bottom of FIG. 4. The initiating methionine codon is believed to be at nucleotides 16–18 of the sequence; the termination codon is marked with "- - -".

FIG. 6 lists the nucleotide sequence (SEQ ID NO: 3) and deduced a amino acid sequence (SEQ ID NO: 4) of the TPC3 open reading frame corresponding to the human TPC3 gene, mRNA, and protein products. The initiating methionine codon is marked with "* * *" and the stop codon with "- - -".

FIG. 9 lists the nucleotide sequence (SEQ ID NO: 5) of the hTR gene and corresponding RNA transcript; the sequence shown is that of one strand of an ~1 kb PstI restriction fragment that can be isolated from plasmid pGRN33. The sequence of the mature hTR transcript, which serves as the template in the telomerase ribonucleoprotein, is marked with * * *—the 3' end of the transcript is marked with an ">".

Figure 1C:
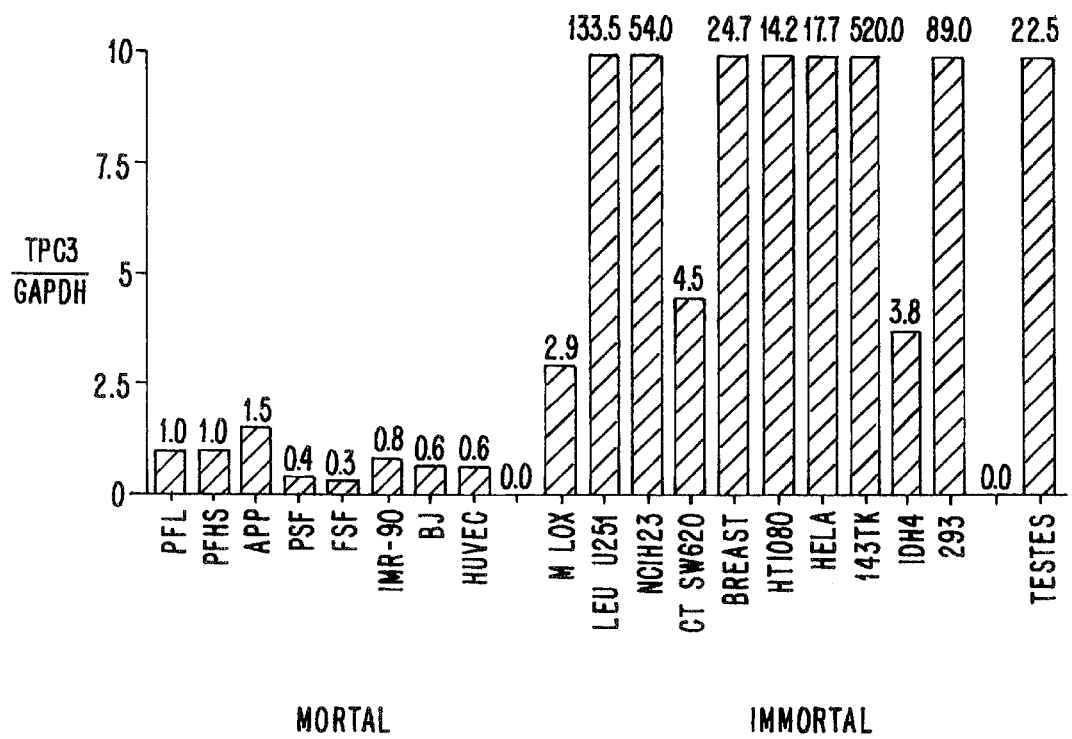
FIG. 1C shows TPC3 mRNA levels normalized to GAPDH levels and illustrates the difference in TPC3 mRNA levels between mortal and immortal cells (the spaces marked "0.0" are provided merely as breaks in the graphed data). GAPDH mRNA was used as a control; due to its greater abundance, the RT-PCR of the GAPDH samples was allowed to complete fewer cycles of PCR than used for the TPC2 or TPC3 samples.

These Figures are discussed in more detail below, where a variety of preferred embodiments of the invention are described.

DESCRIPTION OF THE PREFERRED EMBODIMENTS

The present invention provides methods and reagents for regulating telomere length and modulating telomerase activity in mammalian cells as well as for detecting, diagnosing, and treating related diseases and conditions in humans and other mammals. To facilitate understanding and practice of the invention in its many and diverse applications, this description is organized as shown below.

I. DEFINITIONS
II. CLONING AND CHARACTERIZATION OF THE TPC2 AND TPC3 GENES
III. RECOMBINANT HOST CELLS
IV. OLIGONUCLEOTIDES AND NUCLEIC ACIDS
V. PEPTIDES AND PROTEINS
VI. ANTIBODIES
VII. METHODS
VIII. EXAMPLES

I. DEFINITIONS

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, preferred methods and materials are described. For purposes of the present invention, the following terms are defined below.

"Antibody" refers to naturally occurring and recombinant polypeptides and proteins encoded by immunoglobulin genes, or fragments thereof, that specifically bind to or "recognize" an analyte or "antigen". Immunoglobulin genes include the kappa, lambda, alpha, gamma, delta, epsilon and mu constant region genes, as well as myriad immunoglobulin variable region genes. An antibody can exist as an intact immunoglobulin or as any one of a number of well characterized fragments, e.g., Fab' and F(ab)'$_2$ fragments, produced by various means, including recombinant methodology and digestion with various peptidases.

"cDNA" refers to deoxyribonucleic acids produced by reverse-transcription and typically second-strand synthesis of mRNA or other RNA produced by a gene; if double-stranded, a cDNA molecule has both a coding or sense and a non-coding or antisense strand.

"Complementary to" refers to a polynucleotide sequence that can hybridize specifically to another polynucleotide sequence; for example, a nucleic acid comprising nucleotides in the sequence "5'-TATAC" is complementary to a nucleic acid comprising nucleotides in the sequence "5'-GTATA"

"Corresponds to" or "corresponding to" refers to (i) a polynucleotide having a nucleotide sequence that is substantially identical or complementary to all or a portion of a reference polynucleotide sequence or encoding an amino acid sequence identical to an amino acid sequence in a peptide or protein; or (ii) a peptide or polypeptide having an amino acid sequence that is substantially identical to a sequence of amino acids in a reference peptide or protein.

"Encoding" refers to the inherent property of specific sequences of nucleotides in a nucleic acid, such as a gene in a chromosome or an mRNA, to serve as templates for synthesis of other polymers and macromolecules in biological processes having a defined sequence of nucleotides (i.e., rRNA, tRNA, other RNA molecules) or amino acids and the biological properties resulting therefrom. Thus a gene encodes a protein, if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. A nucleic acid that encodes a protein includes any nucleic acids that have different nucleotide sequences but encode the same amino acid sequence of the protein due to the degeneracy of the genetic code. Nucleic acids and nucleotide sequences that encode proteins may include introns.

"Expression control sequence" refers to nucleotide sequences in nucleic acids that regulate the expression (transcription and/or translation) of a nucleotide sequence operatively linked thereto. Expression control sequences can include, for example and without limitation, sequences of promoters, enhancers, transcription terminators, a start codon (i.e., ATG), splicing signals for introns, and stop codons.

"Immunoassay" refers to an assay that utilizes an antibody to bind an analyte specifically. An immunoassay is characterized by the use of specific binding properties of a particular antibody to isolate, target, and/or quantify the amount of an analyte.

"Label" or "labeled" refers to a detectable marker and to the incorporation of such a marker into a nucleic acid, protein, or other molecule. The label may be detectable directly, i.e., the label can be a radioisotope (e.g., $^3$H,$^{14}$C, $^{35}$S, 125I, $^{131}$I) or a fluorescent or phosphorescent molecule (e.g., FITC, rhodamine, lanthanide phosphors), or indirectly, i.e., by enzymatic activity (e.g., horseradish peroxidase, beta-galactosidase, luciferase, alkaline phosphatase) or ability to bind to another molecule (e.g., streptavidin, biotin, an epitope). Incorporatior of a label can be achieved by a variety of means, i.e., by use of radiolabeled or biotinylated nucleotides in polymerase-mediated primer extension reactions, epitope-tagging, or binding to an antibody. Labels can be attached directly or via spacer arms of various lengths to reduce steric hindrance.

"Naturally occurring" refers to a substance, typically an amino acid, nucleotide, nucleic acid, or protein, that exists in nature without human intervention. For example, deoxyribonucleic acid or DNA is naturally occurring.

"Oligonucleotide" refers to a polymer composed of a multiplicity of nucleotide units (ribonucleotides or deoxyribonucleotides or related structural variants or synthetic analogs thereof) linked via phosphodiester bonds (or related structural variants or synthetic analogs thereof. Thus, while the term "oligonucleotide" typically refers to a nucleotide polymer in which the nucleotides and the linkages between them are naturally occurring; the term also refers to various analogs, such as, for example and without limitation, peptide-nucleic acids (PNAs), phosphoramidates, phosphorothioates, methyl phosphonates, 2-O-methyl ribonucleic acids, and the like. An oligonucleotide is typically rather short in length, generally from about 10 to 30 nucleotides, but the term can refer to molecules of any length, although the term "polynucleotide" or "nucleic acid" is typically used for large oligonucleotides.

"Open reading frame" refers to a nucleotide sequence that encodes a polypeptide or protein and is bordered on the 5'-end by an initiation codon (ATG) or another codon that does not encode a stop codon and on the 3'-end by a stop codon but otherwise does not contain any in-frame stop codons between the codons at the 5'-border and the 3'-border.

"Pharmaceutical composition" refers to a composition suitable for pharmaceutical use in a mammal. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier"

refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in *Remington's Pharmaceutical Sciences*, 19th Ed. (Mack Publishing Co., Easton, 1995). Preferred pharmaceutical carriers depend upon the intended mode of administration of the active agent. Typical modes of administration include enteral (i.e., oral) or parenteral (i.e., subcutaneous, intramuscular, or intravenous; intraperitoneal injection; or topical, transdermal, or transmucosal administration).

"Physiological conditions" refer to temperature, pH, ionic strength, viscosity, and like biochemical parameters that are compatible with a viable organism and/or that typically exist intracellularly in a viable mammalian cell. For example, the intracellular conditions in a mammalian cell grown under typical laboratory culture conditions are physiological conditions. Suitable in vitro reaction conditions for PCR and many polynucleotide enzymatic reactions and manipulations are generally physiological conditions. In general, in vitro physiological conditions comprise 50–200 mM NaCl or KCl, pH 6.5–8.5, 20–45 degrees C., and 0.001–10 mM divalent cation (e.g., $Mg^{++}$, $Ca^{++}$); preferably about 150 mM NaCl or KCl, pH 7.2–7.6, 5 mM divalent cation, and, often, including 0.01–1.0 percent nonspecific protein (e.g., BSA). A non-ionic detergent (Tween, NP40, Triton X-100) can also be present, usually at about 0.001 to 2%, typically 0.05–0.2% (v/v). Particular aqueous conditions may be selected by the practitioner according to conventional methods. For general guidance, the following buffered aqueous conditions may be applicable: 10–250 mM NaCl, 5–50 mM Tris HCl, pH 5–8, with optional addition of divalent cation (s) and/or metal chelators and/or nonionic detergents and/or membrane fractions and/or antifoam agents and/or scintillants.

"Polynucleotide" or "nucleic acid" refers to an oligonucleotide and is typically used to refer to oligonucleotides greater than 30 nucleotides in length.

Conventional notation is used herein to portray polynucleotide sequences: the left-hand end of single-stranded polynucleotide sequences is the 5'-end; the left-hand direction of double-stranded polynucleotide sequences is referred to as the 5'-direction. The direction of 5' to 3' addition of nucleotides to nascent RNA transcripts is referred to as the transcription direction; the DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences". Polynucleotides and recombinantly produced protein, and fragments or analogs thereof, may be prepared according to methods known in the art and described in Maniatis et al., *Molecular Cloning: A Laboratory Manual*, 2nd Ed., (1989), Cold Spring Harbor, N.Y., and Berger and Kimmel, *Methods in Enzymolog*, Volume 152, *Guide to Molecular Cloning Techniques* (1987), Academic Press, Inc., San Diego, Calif., which are incorporated herein by reference.

"Polypeptide," "peptide" and "protein" are used interchangeably herein to refer to a polymer of amino acid residues and to variants and synthetic analogs of the same. Thus, these terms apply to amino acid polymers in which one or more amino acid residues is a synthetic non-naturally occurring amino acid, such as a chemical analog of a corresponding naturally occurring amino acid, as well as to naturally occurring amino acid polymers. Conventional notation is used herein to portray polypeptide sequences: the left-hand end of polypeptide sequences is the amino-terminus; the right-hand end of polypeptide sequences is the carboxy-terminus. The term "recombinant protein" refers to a protein that is produced by expression of a recombinant DNA molecule that encodes the amino acid sequence of the protein. Terms used to describe sequence relationships between two or more polynucleotides or potypeptides include "reference sequence", "comparison window", "sequence identity", "percentage of sequence identity", and "substantial identity". A "reference sequence" is a defined sequence used as a basis for a sequence comparison and may be a subset of a larger sequence, i.e., a complete cDNA, protein, or gene sequence. Generally, a reference sequence is at least 12 but frequently 15 to 18 and often at least 25 nucleotides (or other monomer unit) in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically at least 12 contiguous residues that is compared to a reference sequence; the comparison window may comprise additions or deletions (i.e., gaps) of about 20 percent or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Dr., Madison, Wis.) or by inspection, and the best alignment (i.e., resulting in the highest percentage of homology over the comparison window) generated by any of the various methods is selected.

"Primer" refers to an oligonucleotide, i.e., a purified restriction fragment or a synthetic oligonucleotide, that is capable of acting as a point of initiation of synthesis when placed under conditions in which synthesis of a primer extension product complementary to a nucleic acid strand (the "template") is induced, i.e., in the presence of nucleotides and an agent for polymerization such as DNA polymerase and at a suitable temperature and pH. The primer is preferably single-stranded for maximum efficiency in amplification but may alternatively be double-stranded. If double stranded, the primer may need to be treated to separate its strands before being used to prepare extension products. Primers are typically oligodeoxyribonucleotides, but a wide variety of synthetic and non-naturally occurring oligonucleotide primers can be used for various applications.

A primer must be sufficiently long to prime the synthesis of extension products in the presence of the agent for polymerization. The length of a primer depends on many factors, including application, temperature to be employed, template, reaction conditions, other reagents, and source of primers. For example, depending on the complexity of the target sequence, the oligonucleotide primer typically contains 15–25 or more nucleotides, although it may contain fewer nucleotides. Short primer molecules generally require cooler temperatures to form stable hybrid complexes with template. Primers can be large polynucleotides, such as from about 200 nucleotides to several kilobases or more. A primer must be substantially complementary to the sequence on the template to which it is designed to hybridize to serve as a site for the initiation of synthesis but need not reflect the exact sequence of the template. For example, non-complementary nucleotides may be attached to the 5'-end of the primer, with the remainder of the primer sequence being complementary to the template. Alternatively, non-complementary nucleotides or longer sequences can be interspersed into a primer, provided that the primer sequence has sufficient complementarity with the sequence of the template to hybridize therewith and thereby form a template for synthesis of the extension product of the primer.

"Probe" refers to a molecule that binds to a specific sequence or sub-sequence or other moiety of another molecule. Unless otherwise indicated, the term "probe" typically refers to an oligonucleotide probe that binds to another nucleic acid, often called the "target nucleic acid", through complementary base pairing. Probes may bind target nucleic acids lacking complete sequence complementarity with the probe, depending upon the stringency of the hybridization conditions. Probes can be directly or indirectly labeled.

"Recombinant" refers to methods and reagents in which nucleic acids synthesized or otherwise manipulated in vitro are used to produce gene products encoded by those nucleic acids in cells or other biological systems. For example, an amplified or assembled product polynucleotide may be inserted into a suitable DNA vector, such as a bacterial plasmid, and the plasmid can be used to transform a suitable host cell. The gene is then expressed in the host cell to produce the recombinant protein. The transformed host cell may be prokaryotic or eukaryotic, including bacterial, mammalian, yeast, Aspergillus, and insect cells. A recombinant polynucleotide may serve a non-coding function (e.g., promoter, origin of replication, ribosome-binding site, etc.) as well.

"Recombinant host cell" refers to a cell that comprises a recombinant nucleic acid molecule, typically a recombinant plasmid or other expression vector. Thus, for example, recombinant host cells can express genes that are not found within the native (non-recombinant) form of the cell.

"Selected from" refers, in connection with sequences, to one sequence sharing identity with another sequence.

"Sequence identity" refers to sequences that are identical (i.e., on a nucleotide-by-nucleotide or amino acid-by-amino acid basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

"Specifically binds to" refers to the ability of one molecule, typically a macromolecule such as an antibody or oligonucleotide, to contact and associate with another specific molecule even in the presence of many other diverse molecules. For example, a single-stranded nucleic acid can "specifically bind to" a single-stranded oligonucleotide that is complementary in sequence, and an antibody "specifically binds to" or "is specifically immunoreactive with" its corresponding antigen. Thus, under designated immunoassay conditions, an antibody binds preferentially to a particular protein and not in a significant amount to other proteins present in the sample. Specific binding to a protein under such conditions requires an antibody selected for its specificity for a particular protein. To select antibodies specifically immunoreactive with a particular protein, one can employ a variety of means, i.e., solid-phase ELISA immunoassays are routinely used to select monoclonal antibodies specifically immunoreactive with a protein. See Harlow and Lane (1988), *Antibodies, A Laboratory Manual*, Cold Spring Harbor Publications, New York.

"Specific hybridization" refers to the formation of hybrids between a probe polynucleotide (e.g., a polynucleotide of the invention which may include substitutions, deletions, and/or additions) and a specific target polynucleotide (e.g., a polynucleotide having the sequence of a TPC2 or TPC3 gene or gene product), wherein the probe preferentially hybridizes to the specific target and not to other polynucleotides in the mixture that do not share sequence identity with the target.

"Substantial identity" or "substantially identical" denotes a characteristic of a polynucleotide or polypeptide that comprises a sequence that is at least 80 percent identical, preferably at least 85 percent and often 90 to 95 percent identical, more usually at least 99 percent identical, to a reference sequence over a comparison window of at least 20 nucleotide positions, frequently over a window of at least 25 to 50 nucleotides, wherein the percentage of sequence identity is calculated by comparing the reference sequence to the polynucleotide sequence, which may include deletions or additions that total 20 percent or less of the reference sequence, over the window of comparison. The reference sequence may be a subset of a larger sequence.

"Stringent conditions" refer to temperature and ionic conditions used in nucleic acid, hybridization. The stringency required is nucleotide sequence dependent and also depends upon the various components present during hybridization. Generally, stringent conditions are selected to be about 5 to 20 degrees C. lower than the thermal melting point ($T_m$) for the specific sequence at a defined ionic strength and pH. The $T_m$ is the temperature (under defined ionic strength and pH) at which 50% of a target sequence hybridizes to a complementary probe.

"Substantially pure" means an object species is the predominant species present (i.e., on a molar basis, more abundant than any other individual macromolecular species in the composition), and a substantially purified fraction is a composition wherein the object species comprises at least about 50 percent (on a molar basis) of all macromolecular species present. Generally, a substantially pure composition means that about 80 to 90 percent or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition.

"Suitable reaction conditions" are those conditions suitable for conducting a specified reaction using commercially available reagents. Such conditions are known or readily established by those of skill in the art for a variety of reactions. For example, suitable polymerase chain reaction (PCR) conditions include those conditions specified in U.S.

Pat. Nos. 4,683,202; 4,683,195; 4,800,159; and 4,965,188, each of which is incorporated herein by reference. As one example and not to limit the invention, suitable reaction conditions can comprise: 0.2 mM each dNTP, 2.2 mM $MgCl_2$, 50 mM KCl, 10 mM Tris-HCl, pH 9.0, and 0.1% Triton X-100.

"Telomere length regulatory protein" and "telomerase regulatory protein" refers to polypeptides involved in telomere metabolism and telomerase activity. Such proteins include telomerase, the protein components of telomerase, proteins that selectively bind nucleic acids containing telomere repeat sequences or telomeric ends, proteins required for telomere repair, maintenance, and/or elongation, and proteins necessary for expression or formation of active telomerase enzyme. Although the present invention relates to such proteins generally, mammalian telomerase, and particularly human telomerase, and related proteins are provided as preferred embodiments.

"Telomerase activity" refers to the ability of telomerase protein components to associate with one another and the RNA component of telomerase either in vivo or in vitro into a multi-component enzyme that can elongate telomeric DNA. A preferred assay method for detecting telomerase activity is the TRAP assay. See PCT patent publication No. 95/13381, supra. This assay measures the amount of radioactive nucleotides incorporated into elongation products, polynucleotides, formed by nucleotide addition to a telomerase substrate or primer. The radioactivity incorporated can be measured as a function of the intensity of a band on a PhosphorImager™ screen exposed to a gel on which the radioactive products are separated. A test experiment and a control experiment can be compared by visually using the PhosphorImager™ screens. See also the commercially available TRAP-eze™ telomerase assay kit (Oncor); and Morin, 1989, *Cell* 59:521–529.

II. CLONING AND CHARACTERIZATION OF THE TPC2 AND TPC3 GENES

The present invention provides methods and reagents for regulating telomere length and modulating telomerase activity in mammalian cells as well as for detecting, diagnosing, and treating related diseases and conditions in humans and other mammals. The present invention arose in part out of an effort to clone the protein components of telomerase and other protein components of macromolecules that regulate telomere length and telomerase activity in human and other mammalian cells. These rare proteins and the m nRNAs that encode these proteins are present in very low abundance in mammalian cells, necessitating the use of a novel mRNA isolation and identification method called "subtraction hybridization differential display."

In brief, this method involves obtaining mRNA from a first population of mammalian cells which contain the rare or low abundant protein of interest and from a second population of mammalian cells that contain 10- to 100-fold lower levels of the rare protein. The two mRNA populations are then individually used to generate cDNA preparations by reverse-transcription and second-strand synthesis to form first and second cDNA preparations. A detectable label is incorporated as well into the second cDNA preparation. The two cDNA preparations are then denatured and combined under conditions such that complementary strands of cDNA from the two cDNA preparations anneal to form a mixture of double-stranded and single-stranded cDNA. The mixture of cDNAs is then separated into two different populations, one comprising the label and one that does not, thereby forming an isolated, unlabeled preparation of cDNA that has been enriched for cDNA encoding the rare protein of interest. The steps of hybridization and separation can be repeated as often as desired, and the cDNA isolated after the separation step can be amplified by PCR, to provide cDNA preparations greatly enriched for the desired cDNA. Typically after two cycles of subtraction, cDNAs corresponding to abundant transcripts are depleted more than 100-fold and low abundant transcripts are enriched in the subtracted cDNA libraries. The reproducibility of the method is excellent, and the method can be used to identify low abundant gene products such as those encoding telomere length and telomerase regulatory proteins.

To isolate cDNAs corresponding to telomere length and telomerase regulatory proteins, cDNA libraries were prepared from six different cells lines or tissues, three of which were "telomerase positive" (i.e., the cells express telomerase activity; the IDH4 and 293 cell lines, and testes tissue), and three of which were "telomerase negative" (i.e., the cells do not express telomerase activity; the HUVEC, BJ, and IMR-90 cell lines). These cDNA libraries were subjected to subtraction hybridization against the telomerase negative HUVEC cDNA library. Then, differential display was performed by first replicating each of the six subtracted cDNA libraries with either a single 5'-arbitrary primer or in a PCR with a 5'-arbitrary primer and a 3'-polydT primer, separating the replication products by gel electrophoresis, and identifying and isolating the differentially expressed products (identified visually as bands on a gel).

This process generated a number of differentially expressed cDNAs. Two of these cDNAs that were present in the cDNA libraries generated from the telomerase positive cell lines but not present (or present at much lower levels) in the telomerase negative cell lines, and that were later identified as originating from the 3'-ends of mRNA produced by the TPC2 and TPC3 genes, were isolated, cloned, and characterized by DNA sequence analysis. The DNA sequence analysis was used to design oligonucleotide primers that, in turn, were used to perform reverse-transcription and PCR (RT-PCR) on mRNA prepared from each of the same panel of six cell lines used to prepare the subtracted cDNA libraries. This RT-PCR experiment was designed to confirm that the mRNA corresponding to the putatively differentially expressed cDNAs is expressed at much higher levels in telomerase positive cell lines. The results were as predicted: the RT-PCR generated products of the predicted size; for the primers specific for the TPC2 mRNA, a substantial amount of product was generated using IDH4 mRNA, while lower amounts of product were generated using 293 and testes mRNA, and product was almost undetectable in mRNA prepared from HUVEC, BJ, and IMR-90 cells; for the primers specific for the TPC3 mRNA, product was generated only using mRNA from the telomerase positive cell lines.

To extend the analysis of the expression pattern of TPC2 and TPC3 in various cell lines and tissues, RT-PCR with primers specific for nucleotide sequences in the cDNAs corresponding to the differentially expressed TPC2 and TPC3 mRNAs was performed on a variety of cell lines. As a control, RT-PCR with primers specific for nucleotide sequences in GAPDH mRNA (GAPDH is a "housekeeping" enzyme present in both telomerase positive and telomerase negative cell lines) was performed as well. In brief, the primers used for TPC2 were:

tpc-p1  5'(SEQ ID NO. 6)'-ATGGGGATTCCAGGGTGGAGCT-3', and tpc-p4  5'(SEQ ID NO. 7)-ACCTGCTCTCAGGGCCCACAAGT-3';

and the primers used for TPC3 were:

tpc-p13 5'(SEQ ID NO. 8)-TAAGACAAAGAACAGGTCACAACA-3', and tpc-p14 5'(SEQ ID NO. 9)-ATTTGTGCTTAGAGGTCGTGCCAG-3'.

The RT-PCR was performed by making first strand cDNA made from total RNA with random hexamer primers and then PCR-amplifying the single-stranded cDNA with one of the two primer sets above, following the protocol of 16 to 28 cycles of PCR amplification (typically, 16 cycles for GAPDH mRNA, 25 cycles for TPC2 mRNA, and 27 cycles for TPC3 mRNA), with each cycle consisting of a step at 94 degrees C. for 45 sec., 65 degrees C. for 45 sec., and 72 degrees C. for 90 sec. Other illustrative RT-PCR primers and conditions are shown in Parts C and D of the Examples below.

FIG. 1, in parts A, B, and C, shows the results of RT-PCR analysis using primers specific for the TPC2 (FIG. 1A) or TPC3 (FIG. 1B) cDNA. Under these test conditions, TPC2 and TPC3 mRNA is absent or detectable only at very low levels in the telomerase negative cell lines tested (labeled "Mortal" in the Figure) and detectable in all (most at clearly detectable levels) telomerase positive cell lines tested (labeled "Immortal" in the Figure). These results, which show that TPC2 and TPC3 mRNA is present in testes tissue as well as most tumor cell lines but absent or present at lower abundance in normal cell lines, demonstrate how the methods of the invention for detecting and quantitating TPC2 and/or TPC3 gene products can be used to detect immortal cells, especially telomerase positive cancer cells, and so to diagnose cancer and other diseases and conditions in humans and other mammals. FIG. 1C shows TPC3 mRNA levels normalized to GAPDH levels and illustrates the clear difference in TPC3 mRNA levels between mortal and immortal cells. This RT-PCR analysis also indicated that, as expected, the TPC2 and TPC3 mRNA is present in very low abundance even in telomerase positive cells (TPC2 or TPC3 mRNA amplification products detected after ~25 cycles; GAPDH or HPRT detected after ~15 or ~20 cycles, respectively). Confirmatory evidence for the low abundance of TPC2 mRNA in telomerase positive cells was obtained in the cloning of a cDNA corresponding to one-half of the full length TPC2 mRNA, where a primary screen of a lambda GT11 cDNA library from telomerase positive 293 cells showed that only one of ~1.4 million plaques was positive, indicating a very rare transcript.

Figure 2A:
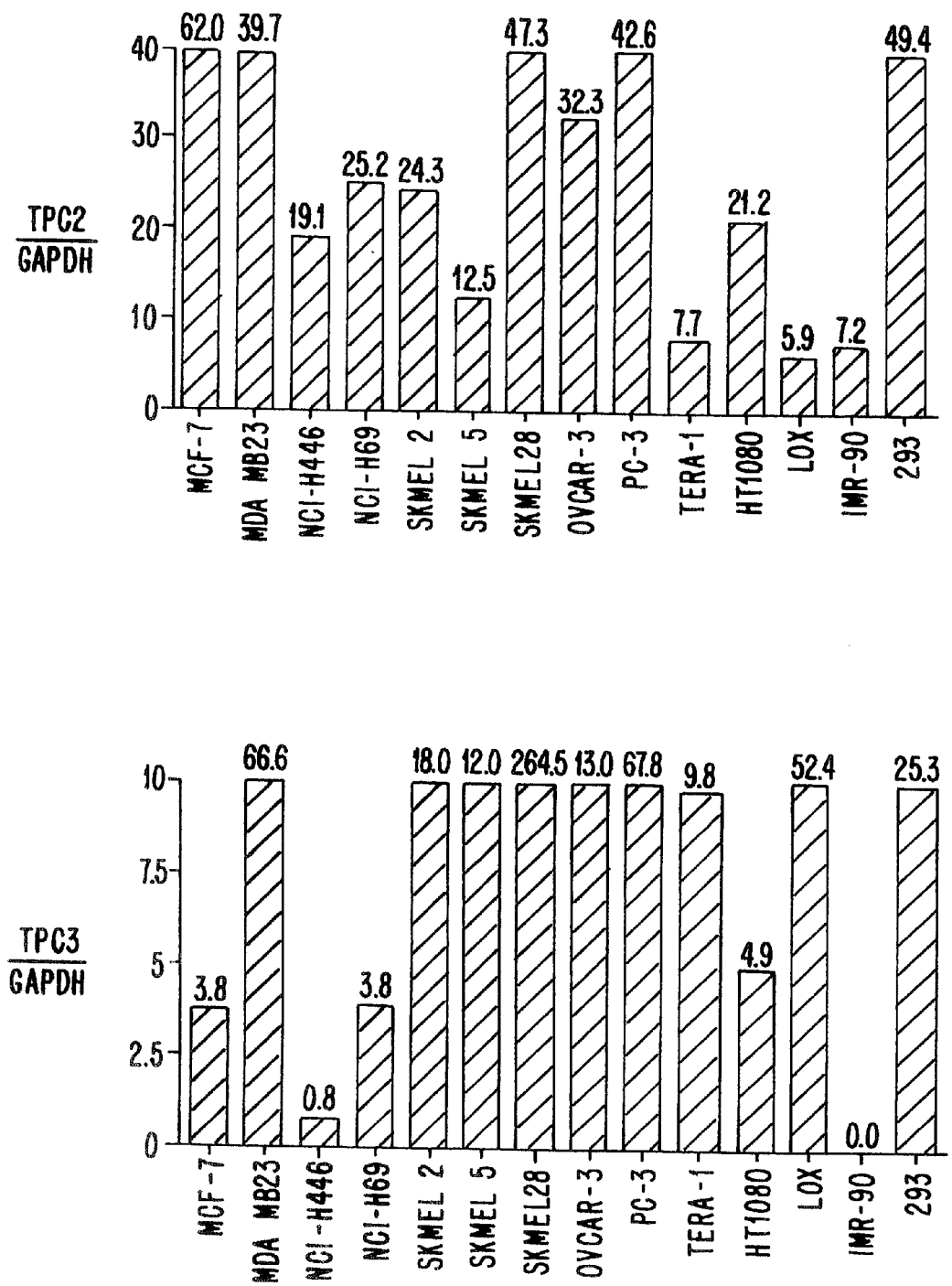
FIG. 2A shows TPC2 and TPC3 mRNA levels normalized to GAPDH mRNA levels in various cell lines, all of which are telomerase positive except IMR-90, and demonstrates a correlation in the levels of these two telomere length and telomerase activity regulatory proteins.
Figure 2C:
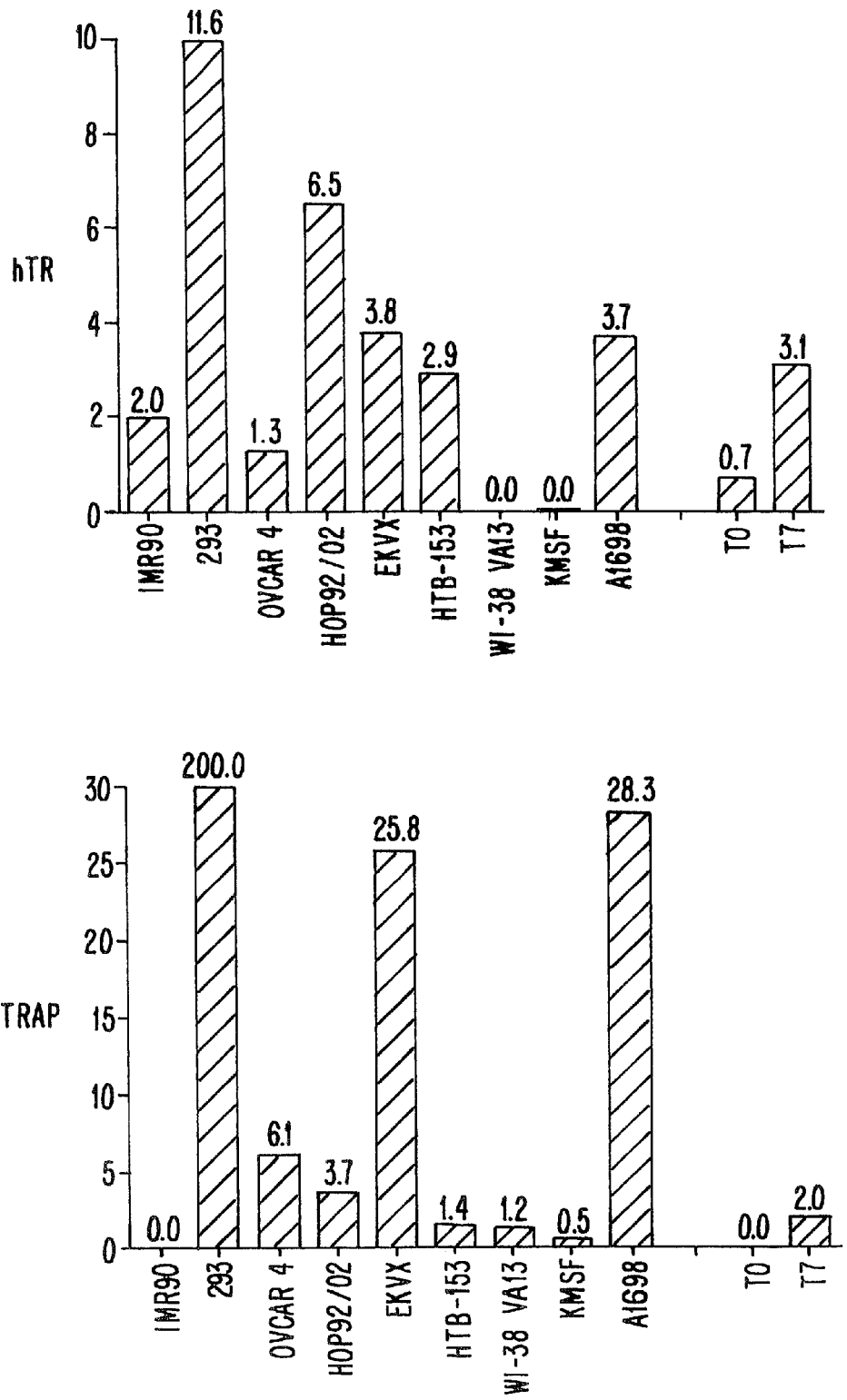
FIG. 2C shows how hTR RNA levels correlate with telomerase activity levels in a variety of cell lines. Taken together, these results show that TPC2 and TPC3 mRNA levels correlate with hTR levels and with telomerase activity levels in a variety of mortal and immortal cells lines.

FIG. 2, in parts A, B, and C, is a bar graph showing the results of an RT-PCR analysis of hTR RNA and TPC2 and TPC3 mRNA levels as well as telomerase activity in a variety of cell lines. FIG. 2A shows TPC2 and TPC3 mRNA levels normalized to GAPDH mRNA levels in various cell lines, all of which are telomerase positive except IMR-90, and demonstrates a correlation in the levels of these two telomere length and telomerase activity regulatory proteins. FIG. 2B shows how TPC3 mRNA levels correlate with telomerase activity levels in a variety of cell lines. The IMR90, HTB-153, WI-38 VA13, KMSF, and T0 (unactivated T cells; note that T7 represents activated T cells) express no or only very low levels of telomerase activity. FIG. 2C shows how hTR RNA levels correlate with telomerase activity levels in a variety of cell lines. The RT-PCR protocol for hTR RNA is described in Part D of the Examples; the nucleotide sequence of the hTR gene and transcribed RNA is shown in FIG. 9.

Taken together, these Figures show that TPC2 and TPC3 mRNA levels as well as hTR levels correlate with telomerase activity levels in a variety of mortal and immortal cells lines. These results demonstrate how the methods of the invention for detecting TPC2 or TPC3 gene products can be used to detect immortal cells, especially telomerase positive cancer cells, and so to diagnose cancer and other diseases and conditions in humans and other mammals. These results also demonstrate the utility of the methods of the invention in which the detection or quantitation of TPC2 or TPC3 gene products, together with measurements of other factors, such as telomere length, telomerase activity, or hTR levels, can be used to identify immortal cells, such as cancer cells, or to evaluate the proliferative capacity of a cell.

The absence or very low abundance of the TPC2 and TPC3 gene products in telomerase negative mortal cells and the low but clearly detectable abundance of those gene products in telomerase positive immortal cells demonstrate the utility of the methods and reagents of the invention for detecting the presence gene products that encode proteins such as the protein components of telomerase and other proteins that regulate telomere length and telomerase activity in mammalian cells. A comparison of telomere length by mean terminal restriction fragment (mean TRF) analysis of immortal cell lines with TPC2 mRNA levels indicates that TPC2 mRNA levels are inversely related to telomere length. In one test, ten immortal cell lines with relatively high TPC2 mRNA levels had mean TRFs of ~2.5 to 5.0 kb, whereas two immortal cell lines with very low TPC2 mRNA levels had mean-TRFs of ~17.5 to 35 kb (probability of this difference arising by chance is less than 1%). In general, TPC2 mRNA levels also correlate well with telomerase activity levels in most cell lines tested.

Tests such as those described above can also be used to determine the mechanism of action by which the TPC2 and TPC3 gene products serve to regulate telomere length and telomerase activity. The tests on TPC2 provide some indication that the TPC2 gene product functions, at least in part, by acting as an indicator of telomere length, much like the yeast EST1 protein. TPC2 is up-regulated in most tumor cell lines and in testes cells and down-regulated in normal cell lines. However, some cell lines with apparently high levels of telomerase activity and very long telomeres have low levels of TPC2 mRNA. As noted above, however, telomerase positive cell lines that have relatively low TPC2 levels also have relatively high mean TRFs, i.e., skin melanoma LOX (~35.2 kb TRF), testes embryonic carcinoma Tera-1 (~27.0 kb), and lung carcinoma NCI-H23 (~17.5 kb). In contrast, skin melanoma lines SK MEL2 (~2.3 kb), SK MEL28 (~15.7 kb), SK MEL5 (~4.0 kb), and testes tissue (~15 kb) have relatively lower mean TRFs and relatively higher TPC2 mRNA levels. Because all of these cell lines have relatively high telomerase activity and high hTR levels, the tests indicate that cell lines with relatively long telomeres in general have low TPC2 mRNA levels, suggesting that the TPC2 protein may encode a protein with a telomere-sensing function. The analysis of TPC3 mRNA levels and telomerase activity in the same cell lines indicates that the TPC3 gene product may act as a core component of the telomerase enzyme.

Significant additional information regarding the mechanism of action of the TPC2 and TPC3 gene products in the regulation of telomere length and telomerase activity can be derived by analysis of the nucleotide sequence and corresponding amino acid sequence of the open reading frames of the corresponding genes. The subtraction hybridization differential display identification and cloning generated only cDNAs corresponding to the 3'-ends of the TPC2 and TPC3 mRNA gene products, but the nucleotide sequence information generated from those cDNAs provided a means to attempt to identify and isolate clones in cDNA libraries prepared from telomerase positive cell lines that comprise additional portions of the mRNA.

Full length cDNA for the TPC2 and TPC3 gene products was obtained by a variety of methods, including the screening of subtracted and other specialized libraries and the use of 5'-RACE. Initially, a lambda GT11 cDNA library containing human cDNA from 293 cells (a telomerase positive human-transformed kidney cell line available from ATCC) was screened to identify lambda clones that hybridized to the short TPC2 and TPC3 cDNAs obtained by subtraction hybridization differential display. Then, after screening additional cDNA libraries and combining fragments from various subclones, full length open reading frames and genes were assembled into the plasmids pGRN92 (comprises the open reading frame of the TPC3 gene) and pGRN109 (comprises the open reading frame of the TPC2 gene).

For example, for TPC2, cDNA inserts in lambda clones were identified by screening with TPC2-specific probes and subcloned into plasmid pGEX and derivative vectors (Pharmacia) to yield plasmids that contained TPC2 cDNA in various reading frames to test expression products and obtain partial nucleotide sequence and deduced amino acid sequence information about the open reading frame of the TFPC2 mRNA. In the case of TPC3, for example, cDNA fragments were cloned into pBluescript IIsk vector (Stratagene) to generate vectors for sequencing and analysis.

Figure 3:
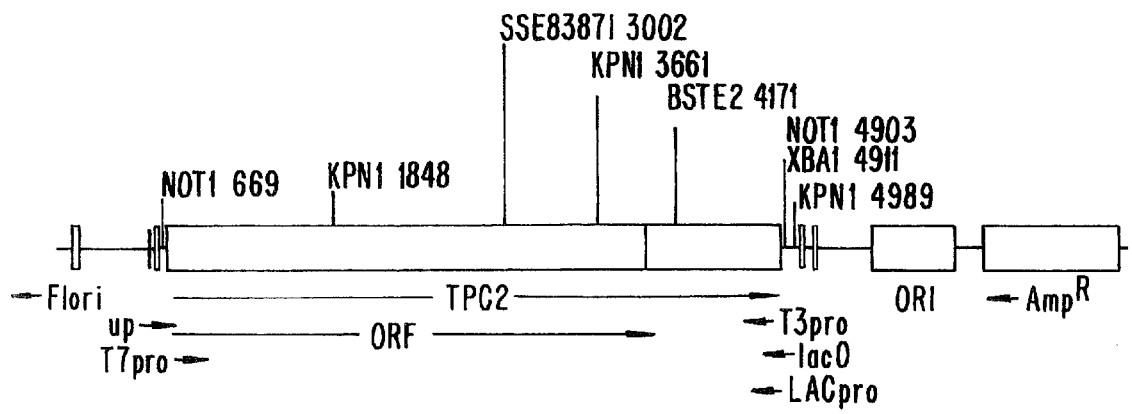
FIG. 3 shows a restriction site and function map of the ~7.2 kb plasmid pGRN109, which contains an 3.5 kb NotI-BstEII restriction fragment that contains an ~3.3 kb open reading frame encoding the TPC2 protein (labeled "ORF" and "TPC2").
Figure 5:
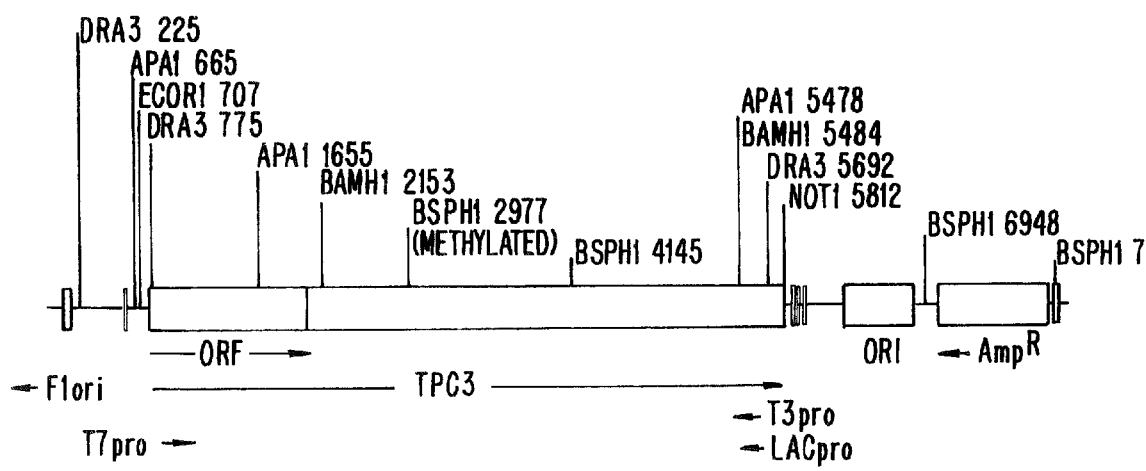
FIG. 5 shows a restriction site and function map of the ~8 kb plasmid pGRN92, which contains an ~1.4 kb EcoRI-BamHI restriction fragment that contains an ~1.1 kb open reading frame encoding the TPC3 protein (labeled "ORF" and "TPC3").

FIG. 3 shows a restriction site and function map of the ~7.2 kb plasmid pGRN109, which contains an ~3.5 kb NotI-BstEII restriction fragment that contains an ~3.3 kb open reading frame encoding the TPC2 protein (labeled "ORF" and "TPC2"). FIG. 4 lists portions of the nucleotide sequence and deduced amino acid sequence of the TPC2 open reading frame corresponding to the human TPC2 gene, mRNA, and protein products. FIG. 5 shows a restriction site and function map of the ~8 kb plasmid pGRN92, which contains an ~1.4 kb EcoRI-BamHI restriction fragment that contains an ~1.1 kb open reading frame encoding the TPC3 protein (labeled "ORF" and "TPC3"). FIG. 6 lists the nucleotide sequence and deduced amino acid sequence of the TPC3 open reading frame corresponding to the human TPC3 gene, mRNA, and protein products. The initiating methionine codon is marked with "***" and the stop codon with "- - -". Plasmid pGRN92 does not comprise nucleotides 1–82 shown in FIG. 6.

Neither the TPC2 nor the TPC3 open reading frame or other gene sequences show significant homology to sequences in public databases other than to ESTs; however, both have motif signatures. TPC2 contains two WW domains and one L22 signature domain; TPC3 contains a homeobox domain. The "homeobox" is a protein domain of 60 amino acids (see Gehring, 1992, Trends Biochem. Sci. 17:277–280) first identified in a number of Drosophila homeotic and segmentation proteins and since found to be extremely well conserved in many animals, including vertebrates. This domain binds DNA through a helix-turn-helix type of structure. Proteins that contain homeobox domains are likely to play a role in development; most are known to be sequence specific DNA-binding transcription factors. Recent publications suggest that homeobox domains can bind RNA as well. See Dubnau and Struhl, Feb. 22, 1996, Nature 379:694. The homeobox domain in TPC3 is: (SEQ ID NO: 10)LAMCTNLPEARVQVWFKNRRAKFR.

TPC2 contains two WW domains and an L22 ribosomal RNA signature domain. The ribosomal protein L22 is a protein component of the large ribosomal subunit that, in *E. coli*, binds 23S rRNA; the protein belongs to a family of ribosomal proteins. See Gantt et al., 1991, EMBO J. 10:3073–3078. For TPC2, this domain is: (SEQ ID NO: 11)SSSKVHSFGKRDQAIRRNPNVPVVV. The WW domain, also known as rsp5 or WWP, is a short conserved region in a number of unrelated proteins, among them dystrophin, responsible for Duchenne muscular dystrophy. The domain spans about 35 residues, can be repeated up to 4 times in some proteins, and has been shown to bind proteins with particular proline-motifs, [A/P]-P-P-[A/P]-Y (SEQ ID NO: 12), and so somewhat resembles SH3 domains. The WW domain is frequently associated with other proteins in signal transduction processes and appears to contain beta-strands grouped around four conserved aromatic positions, generally Trp; the name WWP derives from the presence of these conserved Trp and Pro residues. For TPC2, this domain is represented by three amino acid residue sequences: WSYGVCRDGRVFFINDQLRCT-TWLHP (SEQ ID NO: 12); WFVLADYCLFYY-KAEKKRSSXSIP (SEQ ID NO: 14); and WEEGFTEE-GASYFIDHNQQTTAFRHP (SEQ ID NO: 15).

The availability of plasmids encoding the TPC2 and TPC3 open reading frames provides a wide variety of benefits, including the benefit of recombinant host cells that express recombinant gene products comprising TPC2 and/or TPC3 open reading frame sequences or sequences encoding products that react specifically with TPC2 and/or TPC3 gene products.

II. RECOMBINANT HOST CELLS

In one embodiment, the invention provides recombinant mammalian host cells containing:

(i) a recombinant or synthetic nucleic acid comprising at least about 10 to 15 to 25 to 100 or more contiguous nucleotides corresponding to an open reading frame sequence of a human gene TPC2 contained in a human DNA insert of an ~3.5 kb NotI-BstEII restriction fragment of plasmid pGRN109; or a synthetic or recombinant peptide or protein comprising at least about 6 to 10 to 15 to 25 to 100 or more contiguous amino acids corresponding to an a amino acid sequence encoded by said open reading frame sequence; and (ii) a recombinant or synthetic nucleic acid comprising at least about 10 to 15 to 25 to 100 or more contiguous nucleotides corresponding to an open reading frame sequence of a human gene TPC3 contained in a human DNA insert of an ~1.4 kb EcoRI-BamHI restriction fragment of plasmid pGRN92; or a synthetic or recombinant peptide or protein comprising at least about 6 to 10 to 15 to 25 to 100 or more contiguous amino acids corresponding to an amino acid sequence encoded by said open reading frame sequence of gene TPC3;

said TPC2 and TPC3 genes characterized in coding for proteins that regulate telomere length or modulate telomerase activity and are present in human or other mammalian cells that express telomerase activity.

Other mammalian host cells provided by the invention include those that comprise either or both TPC2- and TPC3-derived recombinant or synthetic nucleic acids, peptides, or proteins. Furthermore, the invention also provides such cells further modified to contain a synthetic or recombinant nucleic acid comprising at least about 10 to 15 to 25 to 100 or more contiguous nucleotides corresponding to a contiguous nucleotide sequence of human hTR located in an ~2.5 kb HindIII-SacI restriction fragment of pGRN33 (ATCC 75926).

The recombinant host cells of the invention have application in many useful methods also provided by the invention. For example, the invention provides recombinant host cells comprising novel expression vectors with expression control sequences operatively linked to nucleotide sequences encoding amino acids in a sequence substantially identical to the proteins encoded by the human TPC2 or TPC3 genes, optionally with a recombinant hTR gene as well. These recombinant host cells are useful for producing recombinant human telomerase, for use in screens to identify agents that modulate telomerase activity or regulate telomere length, as well as for a variety of other purposes described below. The recombinant host cells of the invention can also be incorporated into the germ line and/or somatic tissues of non-human transgenic mammals, as well as be administered to mammals for therapeutic purposes.

Thus, genomic clones of a gene that regulates telomere length or telomerase activity, such as the human TPC2 or TPC3 gene, or recombinant versions thereof, including versions that encode mutein TPC2 or TPC3 gene products, may be used to construct homologous targeting constructs for generating cells and transgenic nonhuman animals having at least one functionally disrupted (or otherwise altered) allele. Guidance for construction of homologous targeting constructs may be found in the art, including: Rahemtulla et al., 1991, *Nature* 353: 180; Jasin et al., 1990, *Genes Devel.* 4:157; Koh et al., 1992, *Science* 256:1210; Molina et al., 1992, *Nature* 357:161; Grusby et al., 1991, *Science* 253:1417; and Bradley et al., 1992, *Bio/Technology* 10:534. See also U.S. Pat. Nos. 5,464,764 and 5,487,992. Transgenic cells and/or transgenic non-human animals may be used to screen for antineoplastic agents and/or to screen for potential carcinogens, as inappropriate expression of a protein that regulates telomere length or telomerase activity may result in a pre-neoplastic or neoplastic state or other disease state or condition. Homologous targeting can be used to generate so-called "knockout" mice, which are heterozygous or homozygous for an inactivated allele. Such mice may be sold commercially as research animals for investigation of immune system development, neoplasia, spermatogenesis, or as pets, or for animal products (foodstuff), or other purposes.

Chimeric transgenic mice are derived according to Hogan et al., 1988, *Manipulating the Mouse Embryo: A Laboratory Manual*, Cold Spring Harbor Laboratory, and *Teratocarcinomas and Embryonic Stem Cells: A Practical Approach*, E. J. Robertson, ed., IRL Press, Washington, D.C. (1987). Embryonic stem cells are manipulated according to published procedures (*Teratocarcinonias and Embryonic Stem Cells: A Practical Approach*, E. J. Robertson, ed., IRL Press, Washington, D.C. (1987); PCT patent publication No. 96/22362; Zjilstra et al., 1989, *Nature* 342:435; and Schwartzberg et al., 1989, *Science* 246:799, each of which is incorporated herein by reference).

Additionally, a TPC2 or TPC3 cDNA or genomic clone may be used to construct transgenes for expressing polypeptides at high levels and/or under the transcriptional control of transcription control sequences which do not naturally occur adjacent to the gene (or vice-versa, i.e., the promoter of the TPC2 or TPC3 gene is positioned in front of a reporter gene for use in screening or other use). For example but not limitation, a constitutive promoter (e.g., an HSV-tk or pgk (phosphoglycerate kinase) promoter) or a cell-lineage specific transcriptional regulatory sequence (e.g., an CD4 or CD8 gene promoter/enhancer) may be operably linked to a protein encoding polynucleotide sequence to form a transgene (typically in combination with a selectable marker such as a neo gene expression cassette). Such transgenes can be introduced into cells (e.g., ES cells, hematopoietic stem cells, cancer cells), and transgenic cells, cell lines, and transgenic nonhuman animals may be obtained according to conventional methods therewith.

The recombinant host cells of the invention are often prepared using, or serve as a source of, valuable oligonucleotide and nucleic acid reagents provided by the present invention, such as the expression control vectors noted above.

These nucleic acid reagents are described in more detail in the following section.

IV. OLIGONUCLEOTIDES AND NUCLEIC ACIDS

In another embodiment, the invention provides synthetic and recombinant oligonucleotides and nucleic acids in a variety of forms, i.e., isolatable, isolated, purified, or substantially pure, and for a variety of purposes, i.e., as probes or primers, as polynucleotide plasmids and vectors for introducing recombinant gene products that regulate telomere length or modulate telomerase activity in mammalian host cells, as restriction fragments for creating useful nucleic acids, and as reagents for therapeutic, diagnostic, and other applications. Isolated or purified polynucleotides of the invention typically are less than ~10 kb in size. In particular, the invention provides recombinant or synthetic nucleic acids comprising at least about 10 to 15 to 25 to 100 or more contiguous nucleotides substantially identical or complementary in sequence to a contiguous nucleotide sequence located in either:

(i) an open reading frame sequence of a human gene TPC2 contained in a human DNA insert of an ~3.5 kb NotI-BstEII restriction fragment of plasmid pGRN109; or (ii) an open reading frame sequence of a human gene TPC3 contained in a human DNA insert of an ~1.4 kb EcoRI-BamHI restriction fragment of plasmid pGRN92.

The novel oligonucleotide probes and primers of the invention typically comprise nucleotides in a sequence substantially identical or complementary to a sequence of nucleotides in a TPC2 or TPC3 gene or gene product to allow specific hybridization thereto in a complex mixture of nucleic acids. Nucleotide substitutions, deletions, and additions may be incorporated into the polynucleotides of the invention. Nucleotide sequence variation may result from sequence polymorphisms of various alleles, minor sequencing errors, and the like. The minimum length of a polynucleotide required for specific hybridization to a target sequence depends on several factors: G/C content, positioning of mismatched bases (if any), degree of uniqueness of the sequence as compared to the population of target polynucleotides, and chemical nature of the polynucleotide (e.g., methylphosphonate backbone, polyamide nucleic acid, phosphorothioate, etc.), among others.

The probes and primers of the invention have useful application in a variety of diagnostic, therapeutic, and other applications. Because they are expressed differentially between immortal human cells lines, TPC2 and TPC3 genes and gene products serve as telomerase activity and tumor cell markers. Oligonucleotides corresponding to unique TPC2 or TPC3 gene sequences can be used as primers or probes, may be attached to other nucleic acids, proteins, labels, etc., and are useful for a variety of purposes, including, for example, as diagnostic probes for tumor cells in clinical specimens. The oligonucleotides of the invention can be used as hybridization probes or PCR primers to detect the presence of TPC2 or TPC3 gene products, to diagnose a neoplastic disease characterized by the presence of an elevated or reduced TPC2 or TPC3 mRNA level in cells, to perform tissue typing (i.e., identify tissues characterized by the expression of telomerase or TPC2 or TPC3 mRNA), and the like. Probes can be used to detect TPC2 or TPC3-specific nucleotide sequences in a DNA sample, such as for forensic DNA analysis or for diagnosis of diseases characterized by amplification, alteration, and/or rearrangements of the TPC2 or TPC3 genes. Certain preferred oligonucleotides of the invention typically comprise at least 8 to 10 to 15 to 25 to 99 to 250 to 1000 or more contiguous nucleotides capable of hybridizing under stringent hybridization conditions to nucleic acids corresponding to a nucleotide sequence in the ~3.5 kb NotI-BstEII insert of pGRNI09 or the ~41.4 kb EcoRI-BamHI insert of pGRN92 and are useful as probes, primers, antisense therapeutics, and ribozyme therapeutics, for example.

Where expression of a polypeptide is not desired, polynucleotides of this invention need not encode a functional protein. Polynucleotides of this invention may serve as hybridization probes and/or PCR primers and/or LCR oligomers for detecting RNA or DNA sequences. Alternatively, polynucleotides of this invention may serve as hybridization probes or primers for detecting RNA or DNA sequences of related genes, for example, genes that encode structurally or evolutionarily related proteins. For such hybridization and other applications, such as those involving PCR, the polynucleotides of the invention need not encode a functional polypeptide. Thus, certain polynucleotides of the invention may contain substantial deletions, additions, nucleotide substitutions, and/or transpositions, so long as the ability of specific hybridization to or specific amplification of a TPC2 or TPC3 gene or mRNA gene product is retained.

As one example, antisense polynucleotides can include nucleotide substitutions, additions, deletions, or transpositions, so long as specific hybridization to the relevant target sequence, typically an mRNA, is retained as a functional property of the polynucleotide. Complementary antisense polynucleotides include soluble antisense RNA or DNA oligonucleotides that can hybridize specifically to mRNA species and genes and so prevent either transcription of the gene to produce the mRNA and/or translation of the mRNA. Antisense polynucleotides of various lengths may be used, although such antisense polynucleotides typically comprise a sequence of at least about 25 consecutive nucleotides that are substantially identical to a naturally occurring TPC2 or TPC3 gene sequence. Antisense polynucleotides may be produced from a heterologous expression cassette in a transfectant cell or transgenic cell, such as a transgenic pluripotent hematopoietic stem cell used to reconstitute all or part of the hematopoietic stem cell population of an individual. Alternatively, the antisense polynucleotides may comprise soluble oligonucleotides that are administered to the external milieu, either in the culture medium in vitro or in the circulatory system or interstitial fluid in vivo. Soluble antisense polynucleotides present in the external milieu have been shown to gain access to the cytoplasm and inhibit translation of specific mRNA species. In some embodiments the antisense polynucleotides comprise methylphosphonate or other synthetic moieties. For general methods relating to antisense polynucleotides, see *Antisense RNA and DNA* (1988), D. A. Melton, Ed., Cold Spring Harbor Laboratory, Cold Spring Harbor, N.Y.

The inhibitory nucleic acid also can be a so-called "sense" or other nucleic acid, i.e., a triplex-forming nucleic acid. As one example, expression of recombinant TPC3 mRNA in a cancer cell line resulted in the inhibition of telomerase activity by over 90%. In this example, the entire ~1.1 kb coding sequence of the TPC3 gene was isolated as an EcoRI fragment (~2.1 kb) from vector pTFATPC3.9 and inserted into the EcoRI site of mammalian expression vector pBBS212 to give rise to two vectors: pGRN111, in which the sense strand of the TPC3 gene is operatively linked to the myelo proliferative sarcoma virus (MPSV) promoter, and pGRN112, in which the antisense strand is operatively linked to the MPSV promoter. Vector pTATPC3.9 was constructed by ligation of TPC3 5'-RACE product (~2.1 kb) into pCRII vector (Invitrogen). The sense and antisense vectors, as well as control vector pBBS212, were used to transform HeTe7 cells by electroporation. The medium was changed to selection medium containing hygromycin (300 $\mu$g/ml) and puromycin (0.2 $\mu$g/ml) for four weeks to obtain individual clones. The individual clones were then isolated, expanded, and assayed for the expression of sense or antisense TPC3 gene product and vector transcription by RT-PCR. The positive clones were then assayed for telomerase activity using the TRAP assay, and mean TRF values were measured at different time points.

Figure 7:
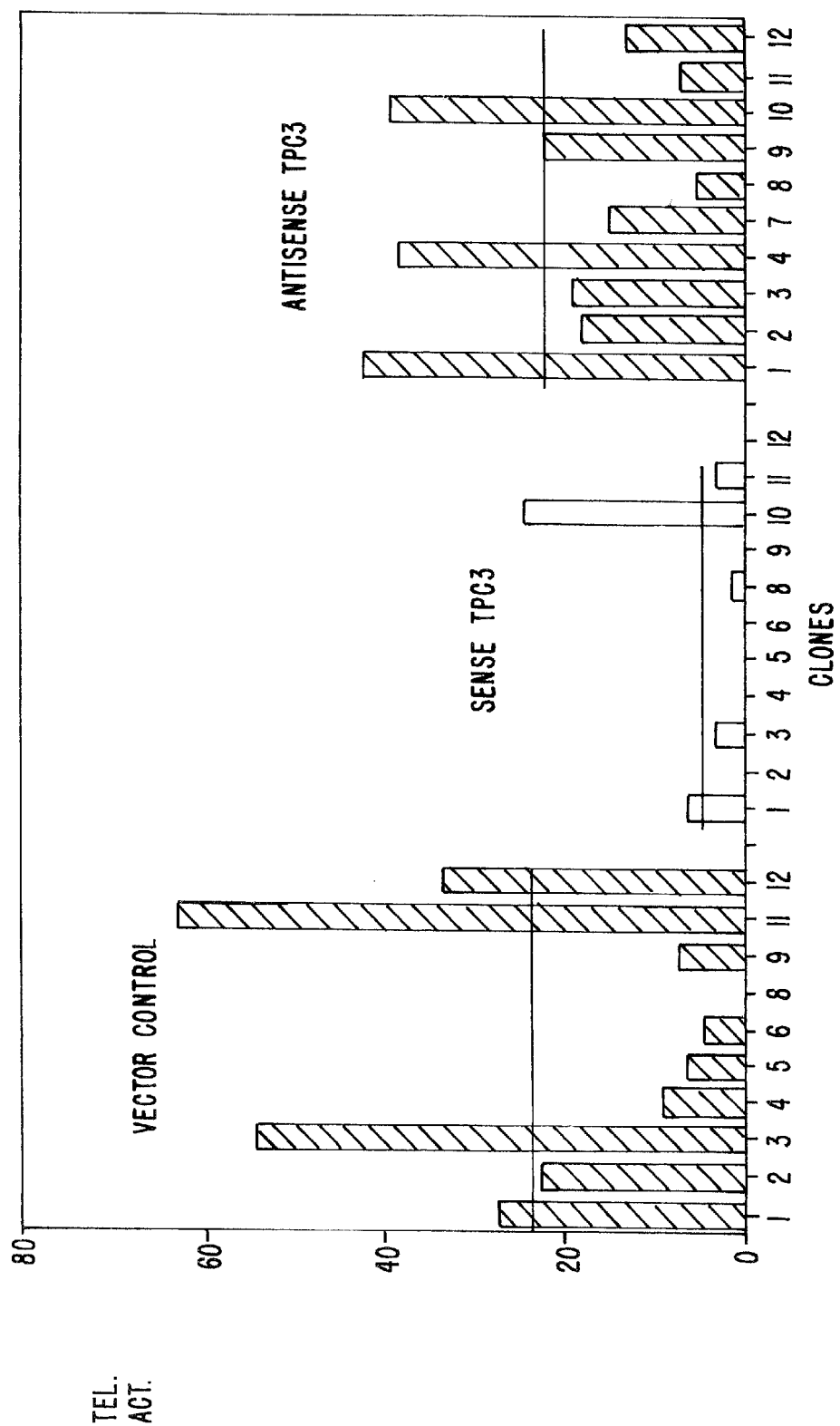
FIG. 7 shows the results of an analysis of telomerase activity levels in stable recombinant HeTe7 clones expressing the sense or antisense mRNA of gene TPC3 or a control vector. The recombinant sense TPC3 mRNA reduced telomerase activity markedly in these cells.
Figure 8:
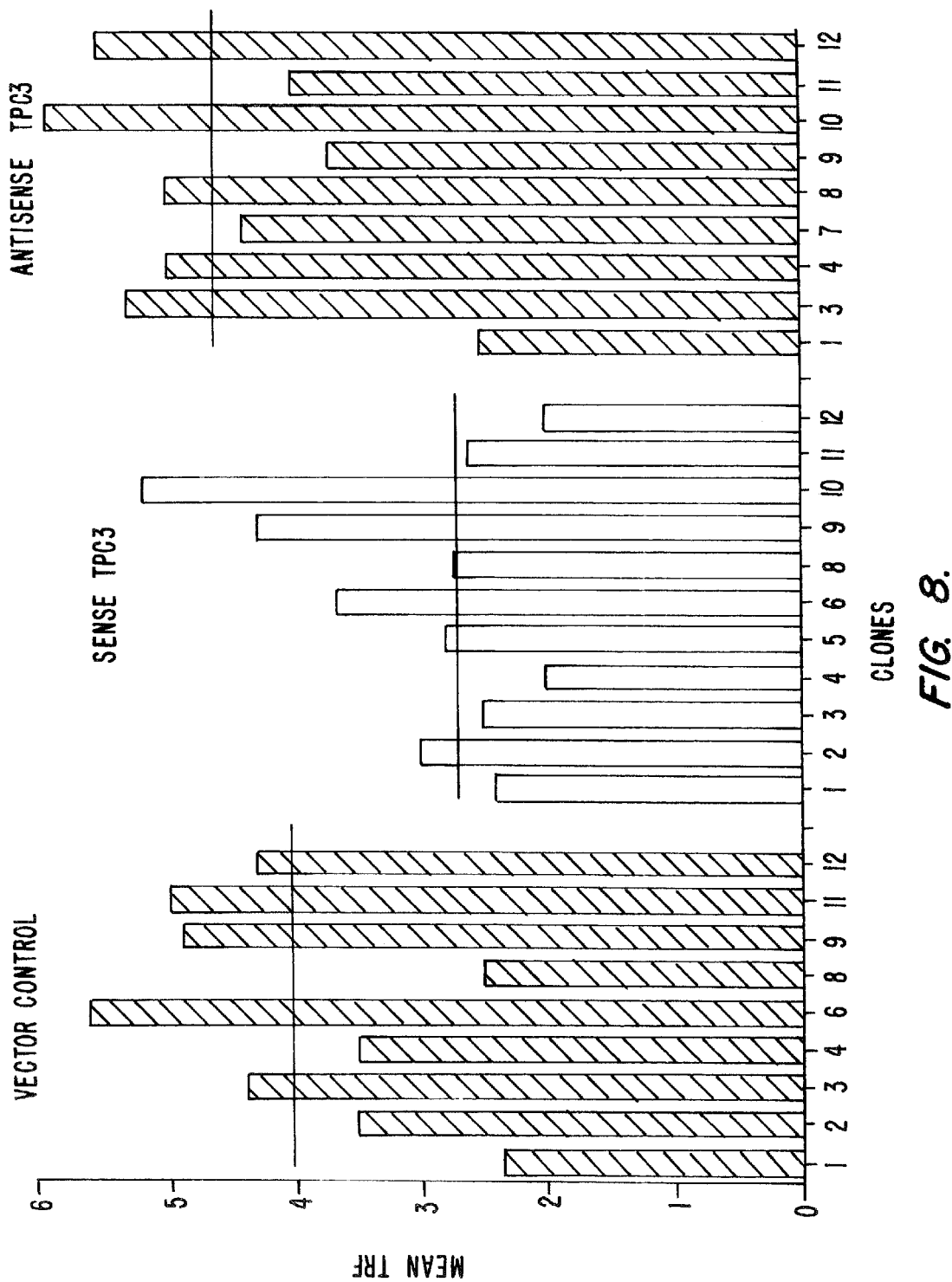
FIG. 8 shows the results of an analysis of telomere length in stable recombinant HeTe7 clones expressing the sense or antisense mRNA of gene TPC3 or a control vector. The recombinant TPC3 sense mRNA decreased telomere length (mean TRF) in the cells.

FIG. 7 shows the results of the analysis of telomerase activity levels in recombinant HeTe7 cells expressing the sense or antisense mRNA of gene TPC3 or a control vector. As noted above, presence of the recombinant sense mRNA reduced telomerase activity markedly in these cells. FIG. 8 shows the results of the analysis of telomere length in recombinant HeTe7 cells expressing the sense or antisense mRNA of gene TPC3 or a control vector. The recombinant TPC3 sense mRNA decreased the mean TRF in the cells. Thus, the recombinant TPC3 gene product can regulate not only telomerase activity but also telomere length in these cells. This experiment shows how the recombinant nucleic acids of the invention can be expressed by transfecting the cell with an expression vector comprising expression control sequences operatively linked thereto. Fragments or analogs of TPC2 or TPC3 can also be expressed and function to compete with other active components of enzymes that regulate telomere length or telomerase activity. Assembly of ribonucleoproteins or other macromolecules with non-functional components results in non-functional complexes and subsequent decrease in associated activity, i.e., telomerase activity, telomere maintenance, and telomere length.

The expression vectors of the invention typically comprise expression control sequences operatively linked to a nucleotide sequence encoding amino acids in a sequence identical to a sequence of amino acids in a TPC2 or TPC3 protein gene product. The operably linked nucleotide sequence typically encodes at least 5 to 9 amino acids, or encodes all of or at least an active portion of the TPC2 or TPC3 proteins, or encode from 15 to 20 to 25 to 100 or more contiguous amino acids in a sequence selected from the amino acid sequences of TPC2 or TPC3, or variant but related sequences thereto. For example, useful TPC2 and TPC3 variant proteins include fusion proteins, in which all or a portion of the TPC2 or TPC3 protein is fused to peptide or polypeptide that imparts some useful feature, such as a binding site for use in affinity purification, i.e., a polyhistidine tag of about six histidine residues or the maltose binding protein. Preferably, these amino acid sequences occur in the given order of the naturally occurring proteins (in the amino-terminal to carboxy-terminal orientation) but may comprise other intervening and/or terminal sequences; generally such polypeptides are less than 1000 amino acids in length, more usually less than about 500 amino acids in lengths, and frequently about 200 amino acids in length. The degeneracy of the genetic code gives a finite set of polynucleotide sequences encoding these amino acid sequences; this set of degenerate sequences may be readily generated by hand or by computer using commercially available software (Wisconsin Genetics Software Package Release 7.0). These and other expression vectors of the invention have many useful applications, including in therapeutic methods of the invention as gene therapy vectors for modulating telomerase activity, either to activate or inhibit that activity, or for regulating telomere length, either to increase or decrease the length, in a target cell or tissue.

Thus, the gene therapy expression vectors of the invention include those that encode variants or "muteins" of the TPC2 and/or TPC3 proteins, i.e., express proteins that differ from TPC2 and/or TPC3 by deletion, substitution, and/or addition of one or more amino acids. The gene therapy vectors of the invention may also, however, encode other useful nucleic acids, such as hTR, or antisense nucleic acids or ribozymes that target the TPC2, TPC3, and/or hTR gene products, i.e., mRNA and telomerase RNA. The vectors of the invention can also code for the expression of a protein which, when presented as an inunmunogen, elicits the production of an antibody that specifically binds to TPC2 or TPC3 proteins or cells expressing those proteins. Such vectors can also code for a structurally-related protein, such as a TPC2 or TPC3 protein fragment or analog. These vectors are useful in the therapeutic methods of the invention for treating or preventing diseases or conditions in which modulation of telomerase activity or telomere length can be of benefit. For example, in telomerase positive cancer cells, inhibition of telomerase activity can prevent telomere maintenance in those cells, inducing upon continued proliferation telomere loss, cell crisis, and death. For such purposes, the gene therapy vectors of the invention that express a non-functional TPC2 or TPC3 mutein or variant protein or other nucleic acid (i.e., over expression of TPC3 mRNA) that can inhibit telomerase formation or telomere elongation by telomerase activity in the cell, such as by competing for RNA component or protein components, inhibition of endogenous gene expression, or other means, are preferred.

Expression vectors of the invention comprise expression and replication signals compatible with the host cell of interest, i.e., sequences that facilitate transcription and translation (expression sequences) of the coding sequences, such that the encoded polypeptide product is produced. Construction of such polynucleotides is well known in the art and is described further in Maniatis et al., supra. For example, but not for limitation, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector. A typical eukaryotic expression cassette will include a polynucleotide sequence encoding a polypeptide linked downstream (i.e., in translational reading frame orientation; polynucleotide linkage) of a promoter such as the HSV, tk, pgk, metallothionein, or any of a wide variety of other promoters suitable for use in mammalian cells, optionally linked to an enhancer and a downstream polyadenylation site (e.g., an SV40 large T Ag poly A addition site). Expression vectors useful for expressing the recombinant TPC2, TPC3, and other proteins of this invention include viral vectors such as retroviruses, adenoviruses and adeno-associated viruses, i.e., for therapeutic methods, plasmid vectors such as pcDNA1 (Invitrogen, San Diego, Calif.), in which the expression control sequence comprises the CMV promoter, cosmids, liposomes, and the like. Viral and plasmid vectors are often preferred for transfecting mammalian cells.

The nucleic acid reagents of the invention also include reagents useful in identifying, isolating, and cloning nucleic acids that encode proteins that interact with TPC2 and TPC3 gene products as well as mammalian (i.e., mouse) homologs of human TPC2 and TPC3 genes. Homologous DNA can be readily identified by screening a genomic or cDNA clone library prepared from the mammalian cells of interest, such as a mouse, rat, rabbit, or other cells, i.e., in yeast artificial chromosomes, cosmids, or bacteriophage lambda (e.g., Charon 35), with a polynucleotide probe comprising a sequence of about at least 24 (or in the range of 15 to 30 or more) contiguous nucleotides (or their complement) of the cDNA sequences of TPC2 or TPC3 disclosed herein. Typically, hybridization and washing conditions are performed at varying degrees of stringency according to conventional hybridization procedures. Positive clones are isolated and sequenced. For illustration and not for limitation, a full length polynucleotide corresponding to the open reading frame sequences of the TPC2 and TPC3 genes can be labeled and used as a hybridization probe to isolate genomic clones from a murine or other mammalian genomic clone or cDNA library (i.e., those available from Promega Corporation, Madison, Wis.).

The nucleic acids of the invention can also be employed to isolate and identify gene products that interact with or bind to TPC2 and/or TPC3 gene products. The yeast "two-hybrid" system (see Chien et al., 1991, *Proc. Natl. Acad. Sci.* (USA) 88:9578) utilizes expression vectors that encode the predetermined polypeptide sequence as a fusion protein and is used to identify protein-protein interactions in vivo through reconstitution of a transcriptional activator (see Fields and Song, 1989, *Nature* 340:245). Usually the yeast Gal4 transcription protein, which consists of separable domains responsible for DNA-binding and transcriptional activation, serves as the transcriptional activator. Polynucleotides encoding two hybrid proteins, one consisting of the yeast Gal4 DNA-binding domain fused to a polypeptide sequence of a first protein and the other consisting of the Gal4 activation domain fused to a polypeptide sequence of a second protein (either the first or second protein typically is a number of different proteins to be screened for ability to interact specifically with the other protein), are constructed and introduced into a yeast host cell. Intermolecular binding, if any, between the two fusion proteins reconstitutes the Gal4 DNA-binding domain with the Gal4 activation domain, which leads to the transcriptional activation of a reporter gene (e.g., lacZ, HIS3) operably linked to the Gal4 binding site. Typically, the two-hybrid method is used to identify novel polypeptide sequences which interact with a known protein.

The invention also provides two- and three-hybrid systems, typically in the form of polynucleotides encoding a first hybrid protein comprising either TPC2 or TPC3, a second hybrid protein, and a reporter gene, wherein said polynucleotide(s) are either stably replicated or introduced for transient expression. The host organism can be a yeast cell (e.g., *Saccharomyces cervisiae*) in which the reporter gene transcriptional regulatory sequence comprises a Gal4-responsive promoter (binding site). Yeast cells comprising (1) an expression cassette encoding a Gal4 DNA binding domain (or Gal4 activator domain) fused to a binding fragment of TPC2 or TPC3 protein; (2) an expression cassette encoding a Gal4 DNA activator domain (or Gal4 binding domain, respectively) fused to a member of a cDNA library; and (3) a reporter gene (e.g., beta-galactosidase) comprising a cis-linked Gal4 transcriptional response element, can be used to screen cDNAs to identify those that encode polypeptides that bind to TPC2 and/or TPC3 proteins specifically. Yeast two-hybrid systems may be used to screen a mammalian (typically human) cDNA expression library, such as, for example, a cDNA library produced from human mature B cell line (Namalwa) mRNA (see Ambrus et al., 1993, *Proc. Natl. Acad. Sci.* (U.S.A.)). Once cDNAs encoding such interacting polypeptides are identified, the resulting polypeptides can be cloned, characterized, and used to screen compounds to identify compounds that can inhibit the binding interaction.

Notwithstanding the many and diverse application of the oligonucleotide and nucleic acid reagents of the invention, one important application relates to the production of recombinant peptides and proteins of the invention, as discussed in the following section.

V. PEPTIDES AND PROTEINS

In another embodiment, the present invention provides peptides, proteins, antibodies, and enzymes relating to genes and gene products that regulate telomere length and telomerase activity in mammalian cells. In particular, the invention provides synthetic or recombinant peptides or proteins comprising at least about 6 to 10 to 15 to 25 to 100 or more contiguous amino acids identical in sequence to an amino acid sequence encoded by an open reading frame sequence of a human gene located in either:

(i) an 3.5 kb NotI-BstEII restriction fragment of plasmid pGRN109; or
  (ii) an ~1.4 kb EcoRI-BamHI restriction fragment of plasmid pGRN92.

The present invention provides the peptides and proteins encoded by the TPC2 and TPC3 genes, as well as fragments and analogs thereof, in isolatable form from eukaryotic or prokaryotic host cells expressing recombinant TPC2 and/or TPC3 protein, or from an in vitro translation system, as well as in purified and substantially pure form from synthesis in vitro or by purification from recombinant host cells or by purification of the naturally occurring proteins using antibodies or other reagents of the invention. Methods for expression of heterologous proteins in recombinant hosts, chemical synthesis of polypeptides, and in vitro translation are well known in the art and are described further in Maniatis et al. and Berger and Kimmel, supra. Such proteins have application in methods for reconstituting in vitro telomerase or other enzymatic activities that maintain telomeres and regulate telomere length. These methods in turn have application in screens for therapeutic agents, for diagnostic tests, and for other applications.

Because they are expressed differentially between immortal human cells lines, TPC2 and TPC3 genes and gene products serve as telomerase activity and tumor cell markers. Polypeptides having the full or partial amino acid sequence of TPC2 or TPC3 proteins are useful, for example, in the production of antibodies against TPC2 or TPC3 proteins and that are useful in the detection of TPC2 or TPC3 proteins in tumor cells. The invention provides purified TPC2 and TPC3 proteins having an amino acid sequence substantially identical to the amine acid sequences encoded by the open reading frames of the TPC2 and TPC3 genes. Such genes include human allelic variants or mammalian cognate genes that can be obtained in accordance with and using the reagents provided by the present invention.

The invention also provides TPC2 and TPC3 protein analogs, non-naturally occurring polypeptides comprising at least 5 to 10 to 15 to 20 to 25 to 100 or more amino acids in a contiguous sequence selected from the amino acid sequences of the TPC2 and TPC3 proteins but include one or more deletions or additions of amino acids, either at the amino- or carboxy-termini, or internally, or both; analogs may further include sequence transpositions. Analogs may also comprise amino acid substitutions, preferably conservative substitutions. Analogs include active fragments as well as various muteins. For example, single or multiple amino acid substitutions (preferably conservative amino acid substitutions) may be made in the naturally occurring sequence. Preferred amino acid substitutions include those that: (1) reduce susceptibility to proteolysis, (2) reduce susceptibility to oxidation, (3) alter post-translational modification of the analog, possibly including phosphorylation, and (4) confer or modify other physicochemical or functional properties of such analogs. TPC2 or TPC3 protein analogs can be immunogenic for TPC2 or TPC3 proteins, i.e., when presented as an immunogen, the analog elicits the production of an antibody that specifically binds to TPC2 or TPC3 proteins. Active fragments can be identified empirically by generating fragments of the full length protein by deletion from either the amino-terminus or the carboxy-terminus or both, and testing the resulting fragments for activity.

Conservative amino acid substitution is a substitution of an amino acid by a replacement amino acid which has similar characteristics (e.g., those with acidic properties: Asp and Glu). A conservative (or synonymous) amino acid substitution does not substantially change the structural characteristics of the parent protein (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (1984), Creighton (ed.), W. H. Freeman and Company, New York; Introduction to Protein Structure (1991), C. Branden and J. Tooze, Garland Publishing, New York, N.Y.; and Thornton et al., 1991, *Nature* 354:105; which are incorporated herein by reference. The following six groups each contain amino acids that are conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W).

Analogs may include heterologous sequences generally linked at the amino- or carboxy-terminus, wherein the heterologous sequence(s) confer a functional property to the resultant analog not shared by the native protein. Such analogs are referred to as fusion proteins and for purposes of the present invention typically comprise a TPC2 or TPC3 protein or analog and an additional peptide or protein moiety. Fusion proteins usefully combine properties of two different polypeptides or proteins, and can be used, for example, to confer a label, such as a polyhistidine polypeptide or a maltose binding protein, useful in affinity isolation of the fusion protein or to protect the fusion protein from degradation inside a cell. The fusion protein may comprise a linker peptide with desired properties, for example, a peptidase site that renders the TPC2 or TPC3 protein or analog cleavable from the remainder of the fusion protein. The fusion protein can also confer an antigenic epitope to the TPC2 or TPC3 protein of interest; antibodies that bind the epitope could then be used to immunoprecipitate the fusion protein for purification or to identify associated proteins.

Thus, the invention provides recombinant fusion proteins in which all or a portion of the TPC2 or TPC3 protein is fused to another polypeptide or protein of interest. For example, plasmids pGRN103, pGRN104, pGRN106, and pGRN110 are expression plasmids of the invention that code for the expression of novel fusion proteins of the invention that comprise a portion of either TPC2 or TPC3 protein and maltose binding protein (MBP). These vectors were created using the commercially available pMALc2 expression vector and system (New England Biolabs). Plasmid pGRN 103 encodes a fusion protein comprising the amino-terminal portion of TPC3 protein and MBP and was prepared by replacing the XmnI-PstI restriction fragment of plasmid pMALc2 with the PvuII-PstI restriction fragment of plasmid pGRN92. Plasmid pGRN104 encodes a fusion protein comprising the carboxy-terminal portion of TPC3 protein and MBP and was prepared by replacing the Ecl136II-BamHI restriction fragment of plasmid pMALc2 with the BspEI (treated with Klenow in the presence of dCTP and dGTP only)-BamHI restriction fragment of plasmid pGRN92. Plasmid pGRN106 encodes a fusion protein comprising the amino-terminal portion of TPC2 protein and MBP and was prepared by replacing the SalI-PstI restriction fragment of plasmid pMALc2 with a SalI-Sse8387I restriction fragment that can be isolated from plasmid pGRN109. Plasmid pGRN110 encodes a fusion protein comprising the carboxy-terminal portion of TPC2 protein and MBP and was prepared by inserting a restriction fragment containing the carboxy-terminal portion of the open reading frame of TPC2 into plasmid pMALc2 such that the fusion protein shown below (SEQ ID NO: 16) results from expression of the plasmid in *E. coli* W3110 cells (only the ends of the MBP and TPC2 proteins at the junction region are shown):

known structure and/or function. See *Proteins, Structures and Molecular Principles* (1984), Creighton (ed.), W. H. Freeman and Company, New York, incorporated herein by reference. Methods to identify protein sequences that fold into a known three-dimensional structure are known. See Bowie et al., 1991, *Science* 253:164. Recognized sequence motifs and structural conformations may be used to define structural and functional domains. Computer programs GAP, BESTFIT, FASTA, and TFASTA in the Wisconsin Genetics Software Package (Genetics Computer Group, 575 Science Dr., Madison, Wis.) can be used to identify sequences in databases, such as GenBank/EMBL, that have regions of homology. Neural network methods, whether implemented in hardware or software, may be used to: (1) identify related protein sequences and nucleotide sequences, and (2) define structural or functional domains in polypeptides. See Brunak et al., 1991, *J. Mol. Biol.* 220:49, incorporated herein by reference.

Thus, one class of preferred peptides and proteins of the invention are fragments of the TPC2 or TPC3 proteins having amino- and/or carboxy-termini corresponding to amino acid positions near functional domain borders. Alternative fragments may also be prepared. The choice of the amino- and carboxy-termini of such fragments rests with the discretion of the practitioner and is based on considerations such as ease of construction, stability to proteolysis, thermal stability, immunological reactivity, amino- or carboxyl-terminal residue modification, or other considerations.

The immunogenic peptides and proteins of the invention can be used in therapeutic immunization and vaccination procedures. See U.S. provisional patent application Serial No. 60/008,949, filed Oct. 20, 1995, incorporated herein by reference. The invention therefore provides a method of

```
        Maltose Binding Protein
****************************************><**Junction*
ProAsnIleProGlnMetSerAlaPheTrpTyrAlaValArgThrAlaValIleAsnAla
AlaSerGlyArgGlnThrValAspGluAlaLeuLysAspAlaGlnThrAsnSerSerSer
AsnAsnAsnAsnAsnAsnAsnAsnAsnLeuGlyIleGluGlyArgIleSerGluPhe
                     TPC Protein
*Junction*><*******************************************
AlaAlaAlaSerThrLueAspLeuLysMetThrGlyArgAspLeuLeuLysAspArgSer
*************************************************************
LeuLysProValLysIleAlaGluSerAspThrAspValLysLeuSerIlePheCysGlu
```

These and other fusion proteins of the invention can be isolated in accordance with standard procedures and then used to immunize animals, i.e., mouse and rabbits, for the production of polyclonal antisera and monoclonal antibodies, as described in the following section.

TPC2 or TPC3 proteins, analogs, peptides, and polypeptides can also be prepared by chemical synthesis using well known methods. For example, various peptides with amino acid sequences corresponding to sequences of the TPC2 and TPC3 proteins can be chemically synthesized in vitro and used to generate antibodies that specifically bind to TPC2 and/or TPC3 proteins. Illustrative peptides of the invention include RGLKRQSDERKRDRE (SEQ ID NO: 17) and KVTSPLQSPTKAKPK, (SEQ ID NO: 18) which have been chemically synthesized in vitro and used to immunize animals to generate antibodies specific for TPC3 protein. Such peptides may correspond to structural and functional domains identified by comparison of the nucleotide and/or amino acid sequence data of a gene or protein to public or other sequence databases. Computerized comparison methods can be used to identify sequence motifs or predicted protein conformation domains that occur in other proteins of immunizing a subject, as well as vaccines useful in the method, against cells that maintain telomeres and express telomerase activity, such as cancer cells, that comprise administering an immunostimulating amount of such peptides or proteins of the invention.

Peptides and proteins of the invention are suitably obtained in substantially pure form if at least about 50 percent. (w/w) or more pure and substantially free of interfering proteins and contaminants. Preferably, these polypeptides are isolated or synthesized in a purity of at least 80 percent (w/w) or, more preferably, in at least about 95 percent (w/w), and are substantially free of other proteins or contaminants.

One important application of the peptides and proteins of the invention is the generation of antibodies that specifically bind to TPC2 or TPC3 proteins, as discussed in the following section.

VI. ANTIBODIES

The proteins and peptides of the invention can also be used to generate antibodies specific for TPC2 or TPC3 proteins, or for particular epitopes on those proteins. TPC2 or TPC3 proteins, fragments thereof, or analogs thereof, can be used to immunize an animal for the production of specific antibodies. For example, but not for limitation, a recombinantly produced fragment of a TPC2 or TPC3 protein or a fusion protein can be injected into a mouse along with an adjuvant following immunization protocols known to those of skill in the are so as to generate an immune response. Alternatively, or in combination with a recombinantly produced polypeptide, a chemically synthesized peptide having an amino acid sequence corresponding to a TPC2 or TPC3 protein may be used as an immunogen to raise antibodies which bind a TPC2, TPC3, or another telomere- or telomerase-related protein. Immunoglobulins that bind the target protein with a binding affinity of at least about $1\times10^6$ $M^{-1}$ can be harvested from the immunized animal as an antiserum, and may be further purified by immunoaffinity chromatography or other means.

Additionally, spleen cells can be harvested from the immunized animal (typically rat or mouse) and fused to myeloma cells to produce a bank of monoclonal antibody-secreting hybridoma cells. The bank of hybridomas can be screened for clones that secrete immunoglobulins that bind the protein of interest specifically, i.e., with an affinity of at least $1\times10^7$ $M^{-1}$. Animals other than mice and rats may be used to raise antibodies; for example, goats, rabbits, sheep, and chickens may also be employed to raise antibodies reactive with a TPC2 or TPC3 protein. Transgenic mice having the capacity to produce substantially human antibodies also may be immunized and used for a source of antiserum and/or for making monoclonal antibody secreting hybridomas.

Thus, the invention provides polyclonal and monoclonal antibodies that specifically bind to TPC2 or TPC3 proteins. Bacteriophage antibody display libraries may also be screened for phage able to bind peptides and proteins of the invention specifically. Combinatorial libraries of antibodies have been generated in bacteriophage lambda expression systems and may be screened as bacteriophage plaques or as colonies of lysogens. For general methods to prepare antibodies, see *Antibodies: A Laboratory Manunal* (1988), E. Harlow and D. Lane, Cold Spring Harbor Laboratory, Cold Spring Harbor, N.Y., incorporated herein by reference.

These antibodies can in turn be used to isolate TPC2 or TPC3 proteins from normal or recombinant cells and so can be used to purify the proteins as well as other proteins associated therewith. Such antibodies are useful in the detection of TPC2 or TPC3 proteins in samples and in the detection of cells comprising TPC2 or TPC3 proteins in complex mixtures of cells. Such detection methods have application in screening, diagnosing, and monitoring diseases and other conditions, such as cancer, pregnancy, or fertility, because the TPC2 and TPC3 proteins are present in most cells capable of elongating telomeric DNA and expressing telomerase activity and are present in those cells at levels significantly higher than the levels observed in telomerase negative cells.

For some applications of the antibodies of the invention, such as identifying immuno-crossreactive proteins, the desired antiserum or monoclonal antibody(ies) is/are not monospecific. In these or other instances, it may be preferable to use a synthetic or recombinant fragment of a TPC2 or TPC3 protein as an antigen rather than the entire protein. More specifically, where the object is to identify immuno-crossreactive polypeptides that comprise a particular structural moiety, such as a DNA-binding domain, it is preferable to use as an antigen a fragment corresponding to part or all of a commensurate structural domain in the TPC2 or TPC3 protein.

Cationized or lipidized antibodies reactive with TPC2 or TPC3 can be used therapeutically to treat or prevent diseases of excessive or inappropriate expression (e.g., neoplasia) of these proteins and the processes regulated thereby. Other methods of the invention are discussed in the following section.

VII. METHODS

The various reagents of the invention described above have a wide variety of applications. The provision of polynucleotides capable of hybridizing to TPC2 or TPC3 cDNA and antibodies that specifically bind to TPC2 or TPC3 proteins allows one to detect expression of TPC2 and TPC3 in cells. The detection of TPC2 or TPC3 gene expression in cells suspected of being cancerous is useful in the diagnosis of cancer. Accordingly, this invention provides methods of detecting TPC2 or TPC3 mRNA or protein in a cell by hybridization or immunoassay methods. Hybridization methods can involve any pf the routine methods including Northern blotting; Southern hybridization; amplification of target or probe nucleic acids by PCR, b-DNA, antibodies labeled with enzymes, LCR, Q-beta replicase, or 3SR; and the like, may also be used.

The polynucleotide sequences of the present invention can be used for forensic identification of individual humans, such as for identification of decedents, determination of paternity, criminal identification, and the like. The invention also provides TPC2 or TPC3 polynucleotide probes for diagnosis of disease states (e.g., neoplasia or pre-neoplasia) by detection of a TPC2 or TPC3 mRNA or rearrangements or amplification of the TPC2 or TPC3 gene in cells explanted from a patient, or detection of a pathognomonic TPC2 or TPC3 allele. Cells which contain an altered amount of TPC2 or TPC3 mRNA as compared to non-neoplastic or non-diseased cells of the same cell type(s) can be identified as candidate diseased cells in accordance with the methods of the invention. Similarly, the detection of pathognomonic rearrangements or amplification of the TPC2 or TPC3 gene locus or closely linked loci in a cell sample will identify the presence of a pathological condition or a predisposition to developing a pathological condition (e.g., cancer, genetic disease).

The isolation of three telomerase-related and telomere length regulatory components, TPC2, TPC3, and hTR, allows the production of recombinant telomerase comprising one or more of these components. In one method, recombinant telomerase is produced by expressing a TPC2 or TPC3 protein or active TPC2 or TPC3 analog and/or recombinant hTR in a cell. In another, telomerase is re-constituted in vitro. The recombinant RNA component of telomerase can be, for example, an RNA molecule derived from the sequence encoded by the ~2.5 kb HindII-SacI insert of pGRN33 (ATCC 75926). Recombinant telomerase is useful, for example for screening assays to determine whether a compound modulates telomerase activity.

Telomerase- and telomere length-modulating agents which reduce a cell's capacity to repair telomere DNA damage (e.g., by inhibiting endogenous naturally occurring telomerase) are candidate antineoplastic agents. Candidate antineoplastic agents are then tested further for antineoplastic activity in assays which are routinely used to predict suitability for use as human antineoplastic drugs. Examples of these assays include, but are not limited to, assays to measure the ability of the candidate agent (1) to inhibit anchorage-independent transformed cell growth in soft agar, (2) to reduce tumorigenicity of transformed cells transplanted into nu/nu mice, (3) to reverse morphological transformation of transformed cells, (4) to reduce growth of transplanted tumors in nu/nu mice, (5) to inhibit formation of tumors or pre-neoplastic cells in animal models of spontaneous or chemically-induced carcinogenesis, and (6) to induce a more differentiated phenotype in transformed cells.

Administration of an efficacious dose of an agent capable of specifically inhibiting telomere-maintenance or telomerase activity to a patient can be used as a therapeutic or prophylactic method for treating pathological conditions (e.g., cancer, inflammation, lymphoproliferative diseases, autoimmune disease, neurodegenerative diseases, and the like), which are effectively treated by modulating telomerase activity and telomere length. Additional embodiments directed to modulation of neoplasia or cell death include methods that employ specific inhibitory nucleic acids, e.g., sense or antisense polynucleotides corresponding to nucleotide sequences encoding TPC2, TPC3, or a cognate mammalian TPC2 or TPC3 protein.

The foregoing description of the preferred embodiments of the present invention has been presented for purposes of illustration and description and is not intended to be exhaustive or to limit the invention to the precise form disclosed but instead to illuminate the many modifications and variations possible in light of the invention and description and to include such modifications and variations as may be apparent to a person skilled in the art in light of this description within the scope of this invention and the claims thereto. All publications and patent documents cited in this application are incorporated by reference in their entirety for all purposes to the same extent as if each individual publication or patent document were so individually denoted.

VIII. EXAMPLES

The following examples are given to illustrate but not limit the invention. Generally, the nomenclature used herein and many of the laboratory procedures in cell culture, molecular genetics, and nucleic acid chemistry and hybridization described below are those well known and commonly employed in the art. All percentages given throughout the specification and examples are based upon weight unless otherwise indicated. All protein molecular weights are based on mean average molecular weights unless otherwise indicated.

A. Methods In Molecular Genetics

Standard techniques are used for recombinant nucleic acid methods, polynucleotide synthesis, in vitro polypeptide synthesis, microbial culture and transformation (e.g., electroporation), and the like. Generally enzymatic reactions and purification steps using commercially available starting materials are performed according to the manufacturer's specifications. The techniques and procedures are generally performed according to conventional methods in the art and various general references (see, generally, Sambrook et al. *Molecular Cloning: A Laboratory Manual*, 2d ed. (1989); Cold Spring Harbor Laboratory Press, Cold Spring Harbor, N.Y., incorporated herein by reference) referenced herein.

Oligonucleotides can be synthesized on an Applied Bio Systems or other commercially available oligonucleotide synthesizer according to specifications provided by the manufacturer. Polynucleotide primers may be prepared using any suitable method, such as, for example, the phosphotriester and phosphodiester methods, or automated embodiments thereof. In one such automated embodiment, diethylphosphoramidites are used as starting materials and may be synthesized as described by Beaucage et al., 1981, *Tetrahedron Letters* 22:1859, and U.S. Pat. No. 4,458,066.

Methods for PCR amplification are known in the art (PCR Technology: *Principles and Applications for DNA Amplification*, Ed. Erlich, Stockton Press, New York, N.Y. (1989); *PCR Protocols: A Guide to Methods and Applications*, eds. Innis, Gelfland, Sninsky, and White, Academic Press, San Diego, Calif. (1990); Mattila et al., 1991, *Nucleic Acids Res.* 19:4967; Eckert and Kunkel, 1991, *PCR Methods and Applications* 1:17; and the U.S. Patents noted above. Optimal PCR and hybridization conditions will vary depending upon the sequence composition and length(s) of the targeting polynucleotide(s) primers and target(s) employed, and the experimental method selected by the practitioner. Various guidelines may be used to select appropriate primer sequences and hybridization conditions (see, Sambrook et al., supra). Generally PCR is carried out in a buffered aqueous solution, preferably at a pH of 7–9, most preferably about 8. The deoxyribonucleoside triphosphates dATP, dCTP, dGTP, and TTP are also added to the synthesis mixture in adequate amounts, and the resulting solution is heated to about 85–100 degrees C. for about 1 to 10 minutes, preferably from 1 to 4 minutes. After this heating period, the solution is allowed to cool to about 20–40 degrees C. for primer hybridization. To the cooled mixture is added an agent for polymerization, and the reaction is allowed to occur under conditions known in the art. This synthesis reaction may occur at from room temperature up to a temperature just over which the agent for polymerization no longer functions efficiently. Thus, for example, if a heat-labile DNA polymerase is used as the agent for polymerization, the synthesis temperature is generally no greater than about 45 degrees C. The agent for polymerization may be any compound or system that will function to accomplish the synthesis of primer extension products, including enzymes. Suitable enzymes for this purpose include, for example, *E. coli* DNA polymerase I or the Klenow fragment thereof, Taq DNA polymerase, and other available DNA polymerases.

The newly synthesized strand and its complementary nucleic acid strand form double-stranded molecules used in the succeeding steps of the process. In the next step, the strands of the double-stranded molecule are separated using any of the procedures described above to provide single-stranded molecules. The steps of strand separation and extension product synthesis can be repeated as often as needed to produce the desired quantity of the specific nucleic acid sequence. The amount of the specific nucleic acid sequence produced will accumulate in an exponential fashion.

B. Subtractive Hybridization Differential Display

Both the subtractive hybridization method and the differential display method have disadvantages for isolating rare mRNAs that are differentially expressed. Subtractive hybridization can be useful for enriching a pool of non-abundant cDNA species, but conventional screening of the resultant library(ies), even if PCR amplified, is biased in favor of identifying species that are still abundant within the selected non-abundant cDNA pool, making difficult the isolation of very rare cDNA species with a conventional subtractive hybridization enrichment protocol. Differential display of mRNA amplified by PCR is biased by the initial abundance of the various mRNA species and often under-represents or fails to detect rare mRNA species among the many mRNA species that are more abundant and not substantially differentially expressed.

The present invention provides a subtractive hybridization differential display method that is particularly preferred for isolating rare mRNAs, such as those expressed by the TPC2 and TPC3 genes. In brief, this method comprises the steps of: (1) one or more cycles of subtractive hybridization of two cDNA populations to generate a population of subtracted cDNA that is selectively enriched for cDNA species of low abundance mRNAs that are present at higher levels in one of the two cDNA populations, and (2) differential display of the cDNA on an electrophoretic gel and recovery of individual differentially expressed cDNAs by recovery from the gel. PCR amplification, under suitable PCR conditions, of said subtracted cDNA population with a 5' primer of arbitrary nucleotide sequence and optionally with a 3' primer comprising poly(dT) and/or poly(dT) and two or more arbitrary nucleotides at the 3' end to generate PCR products is typically used to replicate or amplify a subtracted library.

To accomplish the initial step(s) of subtractive hybridization, RNA prepared by conventional methods from a first cell population and RNA from a second cell population are separately reverse-transcribed and second-strand synthesized to form two pools of double-stranded cDNA, a tester pool comprising sequences of the mRNA species(s) for which enrichment is desired, and a driver pool comprising the sequences to be subtracted from the tester pool. The two pools may be fragmented by endonuclease digestion (restriction endonuclease or non-specific endonuclease) if desired to degrade cDNA consisting of tandem repeated sequences and to enhance hybridization efficiency. The driver pool is labeled, such as by photobiotinylation or attachment of another suitable recoverable label. The driver pool and tester pool are denatured and mixed together in a reaction mixture under hybridization conditions and incubated for a suitable hybridization period. The reaction mixture is contacted with a ligand which binds the recoverable label on the driver cDNA and which can be readily recovered from the reaction mixture (e.g., using avidin attached to magnetic beads), such that a substantial fraction of the driver cDNA and any tester cDNA hybridized thereto is selectively removed from the reaction mixture.

The remaining reaction mixture is enriched for tester cDNA species that are preferentially expressed in the first cell population as compared to the second cell population. The enriched (subtracted) tester cDNA pool may be subjected to one or more additional rounds of subtractive hybridization with a pool of labeled driver cDNA, which may be substantially identical to the initial pool of driver cDNA or which may represent a different cell population having mRNA species which are desired to be subtracted from the subtracted tester cDNA pool. A variety of means for accomplishing the subtractive hybridization(s) and suitable methodological guidance are available to the artisan. See Lee et al., 1991, *Proc. Natl. Acad. Sci.* (U.S.A.) 88:2825; Milner et al., 1995, *Nucleic Acids Res.* 23:176; Luqmani et al., 1994, *Anal. Biochem.* 222: 102; Zebrowski et al., 1994, *Anal. Biochem.* 222:285; Robertson et al., 1994, *Genomics* 23:42; Rosenberg et al., 1994, *Proc. Natl. Acad. Sci.* (U.S.A.) 91:6113; Li et al., 1994, *Biotechiniques* 16:722; Hakvoort et al., 1994, *Nucleic Acids Res.* 22:878; Satoh et al., 1994, *Mutat. Res.* 316:25; Marechal et al., 1993, *Anal. Biochem.* 208:330; El-Deiry et al., 1993, *Cell* 75:817; Hara et al., 1991, *Nucleic Acids Res.* 19:7097; and Herfort and Garber, 1991, *Biotechniques* 11:598, each of which is incorporated herein by reference.

After the subtractive hybridization is completed, the subtracted tester cDNA is subjected to differential display. The general strategy involves amplification of cDNAs from the subtracted tester cDNA pool by PCR using one or a set of arbitrary sequence primers. Arbitrary primers are selected according to various criteria at the discretion of the practitioner so that each will amplify only a fraction of the DNAs in the subtracted cDNA pool so that the amplification products can be resolved and individually recovered on a separation system, such as a polyacrylamide gel. In part because the number and complexity of cDNA species represented in any particular subtracted tester pool may vary considerably depending upon the nature and complexity of the driver and tester pools, the selection of arbitrary primers and their sequence(s) is determined by the practitioner with reference to the literature. See U.S. patent application Ser. No. 08/ 235,180, filed Apr. 29, 1994; Linskens et al., 1995, *Nucleic Acids Res.* 23 (16): 3244–3251; Liang et al., 1993, *Nucleic Acids Res.* 21:3269; Utans et al., 1994, *Proc. Natl. Acad. Sci.* (U.S.A.) 91:6463; Zimmermann et al., 1994, *Proc. Natl. Acad. Sci.* (U.S.A.) 91:5456; Fischer et al., 1995, *Proc. Natl. Acad. Sci.* (U.S.A.) 92:5331; Lohmann et al., 1995, *Biotechniques* 18:200; Reeves et al., 1995, *Biotechniques* 18:18; and Maser et al., 1995, *Semin. Nephrol.* 15:29, each of which is incorporated herein by reference.

The subtracted tester cDNA pool and a separate cDNA pool prepared in the same way from a cell line or tissue that does not express (or expresses at lower levels) the rare protein is amplified with suitable arbitrary primer(s) (i.e., primers having a predetermined sequence that is selected without reference to a sequence of a desired differentially expressed mRNA) for suitable number of amplification cycles to generate sufficient amplification product for display and recovery of desired species, as can be determined empirically. The primer(s) may comprise 5'-terminal sequences which serve to anchor other PCR primers (distal primers) and/or which comprise a restriction site or half-site or other ligatable end. The amplified products are usually labeled and are typically resolved by electrophoresis on a polyacrylamide gel; the location(s) where label is present in the subtracted tester cDNA but not present (or present at much lower levels) in the control cDNA are excised, and the labeled product(s) is (are) recovered from the gel portion, typically by elution.

The resultant recovered product species (typically an expressed sequence tag or EST cDNA) can be subcloned into a replicable vector with or without attachment of linkers, amplified further, and/or sequenced directly. Once the EST(s) is recovered, it can be used to obtain a substantially full length cDNA from a cDNA library. The EST(s) can be sequenced and the sequence information used to generate a primer for primer extension (5'-RACE), or the EST can be labeled and used as a hybridization probe to identify larger cDNA clones from a cDNA library. Genomic or full length cDNA clones corresponding to ESTs can be isolated from clone libraries (e.g., available from Clontech, Palo Alto, Calif.) using the labeled EST (e.g., by nick-translation or end-labeling) or other hybridization probes with nucleotide sequences corresponding to those identified in the EST in conventional hybridization screening methods.

Thus, double stranded cDNA is made from total RNA purified by CsCl gradient centrifugation. In general, mix 5 μg of total RNA, 0.5 μg oligo dT (12 to 18 bases), and water (deionized water is routinely used) in a total of 7 μl, denature RNA at 95 degrees C. for 5 to 10 minutes, and placed on ice. The denatured RNA and oligo dT is then added to a tube containing 4 μl of 5× first strand synthesis buffer (BRL), 2 μl of 0.1 M DTT (BRL), 1 μl of dNTP (10 mM each), and 1 μl of RNAsin (Pharmacia), and warmed for 2 minutes at 42 degrees C. About 5 µl of Superscript II™ reverse transcriptase (BRL) is added to the reaction mixture, and first strand cDNA synthesis is performed at 42 degrees C. for 60 minutes. Then, the reaction mixture is placed on ice and is ready for the synthesis of second strand. The first strand cDNA is added to a tube containing 111.1 µl of water, 16 µl of 10× E. coli DNA ligase buffer, 3 µl of dNTP (10 mM each), 1.5 µl of E. coli DNA ligase (15 units, BRL), 7.7 µl E. coli DNA polymerase (40 units, Pharmacia), and 0.7 µl of E. coli RNAse H (BRL). The reaction mixture is incubated for two hours at 16 degrees C. , and then 1 µl of T4 DNA polymerase (10 units, Pharmacia) is added. The incubation continues for 5 more minutes at the same temperature, and the reaction is stopped by the addition of 2 µl of 0.5 M EDTA and phenol/chloroform extraction, usually performed twice. The double-stranded cDNA is precipitated with ethanol and resuspended in 12 µl of TE buffer.

The cDNA is then modified by the addition of linkers. Mix 10 µl of cDNA prepared as above with 4 µl of 10× buffer for RsaI, 21 µl of water, and 5 µl of RsaI (25–50 units), and incubate the mixture for two hours at 37 degrees C. Four µl is removed and checked on an agarose gel (1%) along with the uncut cDNA for completion of digestion. The restriction enzyme is then inactivated for 10 min. at 65 degrees C.

The linkers are prepared as double stranded oligonucleotides by mixing 10 µg of each of:

NotA (5'-pATAGCGGCCGCAAGAATCA-NH$_2$-3')(SEQ ID NO: 19) ; and

NotB (5'-TGAATTCTTGCGGCCGCTAT-3')(SEQ ID NO: 20) ; or

Ancol (5'-pCAGAAGCTTGGTTGGATCCAGCAAG-NH$_2$-3')(SEQ ID NO: 21) ; and

PCR02 (5° CTTGCTGGATCCAACCAAGCTTCTG-3') (SEQ ID NO: 22), with 5.6 µl 10× buffer (One for all™, Pharmacia) and water to a final volume of 56 µl. Heat the mixture at 58 degrees C. for 5 minutes, then 55 degrees C. for 5 minutes, and then 45 degrees C. for 10 minutes. Add 55 µl of double stranded oligonucleotide NotAB to the tube containing the digested tester cDNA (HUVEC, BJ, IMR90, IDH4, 293 or testes tissue—the telomerase negative cell lines are used as controls). Add 55 µl of double stranded oligonucleotide Ancol-PCR02 to the tube containing the digested driver cDNA (HUVEC). To both tubes add 2 µl of 100 mM ATP, 3.3 µl of 10× lipase buffer (Pharmacia), 1 µl of T4 DNA ligase (Pharmacia), and water to 100 µl. The reaction mixture is incubated at 15 degrees C overnight. The reaction mixture is then removed from a 15 degrees C. water bath to room temperature and incubated for another two hours. The ligated cDNA is extracted with phenol/chloroform twice and ethanol precipitated. The pellet is resuspended in 12 µl of TE buffer. Half of the product is loaded on a 1.4% low melting point agarose gel, and DNA with a size range from 100 to 1600 base pairs is excised.

PCR amplification of the tester and driver cDNA libraries is carried out by taking about 1 µl of each gel slice isolated as above (melted at 65 degrees C. before use) and mixing with 10 µl of NotB (for testers—this oligonucleotide serves as both the 5' and 3' primers) or PCR02 (for the driver), 5 µl of 10× PCR buffer, 6 µl dNTP (2.5 mM each), 1 unit of Taq polymerase (Boehringer Mannheim or Perkin Elmer), 1 unit of Pfu polymerase (Stratagene), 0.2 µg of gene 32 protein (Boehringer Mannheim), and water to 50 µl. PCR is performed for 20 cycles at 94 degrees C. for 45 sec., 60 degrees C. for 45 sec., and 72 degrees C. for 2 min., with a 5 min. extension at 72 degrees C. after completion of the last cycle.

The driver is PCR amplified in multiple reactions to make enough DNA for photobiotinylation.

Photobiotinylation of the driver cDNA is conveniently accomplished as follows. About 100 µg of driver cDNA in 1 mM EDTA is mixed with 100 µl of photo biotin (Vector). This mixture is placed on ice with the lid open and irradiated for 15 min. with a light source located about 10 cm away from the tube. After the irradiation, 30 µl of 1 M Tris-Cl (pH 9.1) is added to the tube, and the biotinylated DNA is extracted with water-saturated butanol several times (4×) until the orange color disappears from the aqueous phase. The extraction process is repeated once, and the biotinylated DNA is precipitated with ethanol and resuspended in TE buffer to a final concentration of 1 µg/µl.

Subtraction hybridization is conveniently accomplished as follows. Mix 8 µg of biotinylated driver DNA with 0.4 µg of tester DNA (concentrations estimated by OD measurement and ethidium bromide staining of the gel). The mixed DNA is precipitated with ethanol and resuspended in 10 µl of HE buffer (10 mM HEPES, pH 7.3, 1 mM EDTA). The DNA is denatured at 100 degrees C. for 4 min. and transferred to ice. About 10 µl of 2× hybridization solution containing 1.5 M NaCl, 50 mM HEPES, pH 7.3,10 mM EDTA, and 0.2% SDS is then added to the tube. Two drops of mineral oil are added, and the DNA is denatured again at 100 degrees C. for 4 min. and transferred to a water bath at 68 degrees C. The hybridization is performed at this temperature for 22 hours. Biotinylated DNA is removed with streptavidin MagneSphere™ Paramagnetic Particles (Promega), and the tester DNA remaining is recovered.

A second subtraction is performed by mixing recovered tester DNA (about 80 µl) with 8 µl (8 µg) of biotinylated driver DNA and then precipitation with ethanol. The precipitated DNA pellet is resuspended in 10 µl of HE buffer. The denaturation, hybridization, and recovery are performed as above; however, the second hybridization is performed for only 2 hours at 68 degrees C. PCR amplify the recovered DNA (0.3 µl) for 18 cycles in a reaction mixture containing 2 µl of 10× Pfu polymerase buffer, 2.5 µl of 2.5 mM dNTP, 0.2 µl of Taq polymerase (1 unit), 0.4 µl of Pfu polymerase (1 unit), 0.04 µl of T4 gene 32 protein, and water to 20 µl. The products are checked on a 1% agarose gel to confirm relative concentrations. The subtraction hybridization can be repeated on these samples. The final subtracted samples are PCR amplified (18 cycles) and diluted (1 to 10 or 1 to 15) and used for enhanced differential display.

Enhanced differential display of subtracted cDNA involves PCR amplification with 5' arbitrary primer(s) and a 3' oligo dT primer with two randomized bases at the 3' end, recovery of bands identified as containing cDNA corresponding to differentially expressed mRNAs, and PCR amplification, sequencing, and/or cloning of the bands identified. Add 1 µl of one 5' primer (20 µM stock) or two 5' primers (half of each) or 1.2 µl of one 5' primer (1 µl) and one 3' primer (0.2 µl) to the tube. Add 1 µl of subtracted DNA to the same tube. To this mixture, add 8 µl of cocktail mix containing 1 µl of 10× PCR buffer for Pfu polymerase (commercially available), 1 µl of dNTP (2.5 mM each), 0.3 mM alpha-$^{32}$P-dATP, 0.1 µl of Taq polymerase, 0.2 µl of Pfu polymerase (Stratagene), 0.02 µl of T4 gene 32 protein (Boehringer Mannheim), and 5.38 µl water. Overlay one drop of mineral oil, and PCR amplify for 4 cycles at 94 degrees C. for 45 sec., 39 degrees C. for 1 min., and 72 degrees C. for 1 min., and then 22 cycles at 94 degrees C for 45 sec., 60 degrees C. for 1 min., and 72 degrees C. for 1 min., with a final extension for 5 min. at 72 degrees C. About 5 µl of formamide/dye is added to the PCR product, and the products are denatured at 95 degrees C. for 2–3 min. and loaded onto a prewarmed 6% polyacrylamide sequencing gel, which is run at 1900 to 2000 constant voltage (do not allow current to reach 50 mA) until the xylene cyanol dye is one inch from the bottom of the gel. The gel is dried under vacuum at 80 degrees C. for 45 min. and exposed to PhosphorImager™ screen (for notebook record) and/or then to X-ray film at room temperature for one or two days (tape the gel to the film and punch three holes at the three corner of the gel and film for easy identification of bands).

Differentially expressed gene fragments appear as bands on the screen or film that are present in the lanes on the gel corresponding to the cDNA of the tester cells but present at lower levels or absent from the lanes corresponding to the cDNA of the control lanes. The bands can be recovered from the gel by first aligning the gel with the film or screen (based on the three holes and marks) and then excising the bands of interest with a razor blade and transferring the gel slice to an Eppendorf™ tube. Rinse the razor blade between each cutting operation to avoid cross contamination. To remove the urea and paper backing used with sequencing gels without substantial loss of the desired DNA, add about 900 μl of TE buffer to the tube containing the gel slice, incubate the tube at room temperature for 10 min., and then remove and discard the paper and TE buffer. To prepare a solution of the desired DNA from the gel slice, the gel slice is suspended in 40 μl of TE buffer containing 100 mM NaCl and heated for 10 min. at 95–98 degrees C. The liquid is collected (a short centrifugation collects the liquid at the bottom of the tube) and serves as a source of the desired DNA.

This DNA can be PCR-amplified by placing 1–3 μl of recovered DNA in a 50 μl total reaction volume in a reaction mixture containing 6 μl of total primer(s), 5 μl of 10× PCR buffer for Pfu polymerase, 6 μl of dNTP (2.5 mM each), 0.25 μl of Taq polymerase, 0.5 μl of Pfu polymerase, 0.05 μl of T4 gene 32 protein, and water. The PCR is performed for 25 cycles at 94 degrees C. for 45 sec., 60 degrees C. for 1 min., and 72 degrees C. for 1 min., with a 5 min. extension at 72 degrees C. at the end of the last cycle. The PCR products can be stored or further processed, i.e., subcloned and sequenced.

The availability of plasmids comprising restriction fragments corresponding to the open reading frames of the TPC2 and TPC3 genes makes possible the efficient isolation of these gene and gene products from other mammalian cells as well as the chemical synthesis in vitro of these genes and gene products and related reagents, i.e., peptides, oligonucleotides, antibodies, and antibody fragments.

C. RT-PCR Protocol for TPC3

Cell extracts are prepared using CHAPS, as described for the TRAP assay (TRAP-eze™ kit, Oncor). About 2 μl of cell extract are used per assay; typically 30–35 cycles of PCR are performed. Total RNA is prepared using the TRIzol™ RNA extraction method (Life Technologies) on cell pellets or CHAPS extracts. Each PCR tube contains: 15 μl of water; 2.5 μl of 25 μM Mn(OAc)$_2$; 5.5 μl of 5× EZ buffer (Perkin Elmer); 0.3 μl of 25 μM dNTPs; 1 μl of rTth DNA polymerase buffer (Perkin Elmer); 0.1 μl (300 μM) of primer TF2 (5'-CTCACTGTAGACACTGCCTCAGTTTC-3')(SEQ ID NO: 23); and 0.1 μl (300 μM) of primer TR2 (5'-CAGAGGCTGGCACTGGAACTCAAGATC-3')(SEQ ID NO: 24) in a total volume of ~25 μl. RT-PCR conditions include a six minute treatment at 94 degrees C. to denature protein-RNA complexes; a thirty minute treatment at 65 degrees C. for the reverse transcription reaction; a 1.5 minute treatment at 94 degrees C. to denature DNA-RNA complexes; thirty cycles of PCR amplification with each cycle comprising a 30 second treatment at 94 degrees C. and a 30 second treatment at 65 degrees C.; and a final extension reaction by treatment for seven minutes at 60 degrees C. After PCR, the samples can be analyzed by gel electrophoresis using 1× TBE polyacrylamide gels and staining with SYBR-Green I. Tests showed that this primer set amplifies band of correct size in both mortal and immortal cell lines and demonstrate that the TPC3 mRNA is expressed more abundantly in immortal cell lines.

D. RT-PCR Protocol for hTR

First strand cDNA synthesis is performed by mixing total RNA (1 μg) with 40 to 80 ng random hexamer in 11 μl, heating to 95 degrees C. for 5 min. to denature the nucleic acids (the thermal cycler may be used for this step), and then cooling on ice. The reaction mixture (8 μl) containing 4 μl of 5× buffer (BRL, provided with the RTase), 2 μl of 0.1 M DTT, 1 μl of 10 mM dNTP (each), and 1 μl of RNAse inhibitor (P1harmacia) is added to the denatured RNA and hexamer mixture and placed in a water bath at 42 degrees C. After a 1–2 min. incubation, 1 μl of Superscript II™ RTase (BRL) is added to the mixture and the incubation continued for 60 min. at 42 degrees C. The reaction is stopped by heating the tube containing the reaction mixture for 10 min. at 95 degrees C. The first strand cDNA is collected by precipitation and brief centrifugation and aliquoted to new tubes, in which it can be quickly frozen on dry ice and stored at −80 degrees C., if necessary, for later use.

PCR amplification of hTR cDNA with specific primer sets can be generally accomplished as follows. About 1 μl of cDNA is used for each primer set. For a 10 μl PCR with $^{32}$P-dATP nucleotide, 1 μl of cDNA is mixed with 1 μl of 10× Taq buffer, 20 pmol of each primer, 1 μl of 2.5 mM dNTP, 5 μCi alpha-$^{32}$P-dATP, 1 unit of Taq polymerase (Boehringer Mannheim), 1 unit of Taq antibody (Clontech), 0.2 μg of T4 gene 32 protein (Boehringer Mannheim), and water to 10 μl. One drop of mineral oil is then added to the tube. The conditions for PCR amplification for hTR are about 20 cycles of amplification, with each cycle comprising a treatment at 94 degrees C. for 45 sec., 60 degrees C. for 45 sec., and 72 degrees C. for 1.5 min. The primers used for the RT-PCR of hTR are shown below.

Upstream primer: F3b, 5'-TCTAACCCTAACTGAGAAGGGCGTAG-3'(SEQ ID NO:25);

Downstream primer: R3c, 5'-GTTTGCTCTAGAATGAACGGTGGAAG-3'(SEQ ID NO:26).

Amplification of hTR with the F3b and R3c primer pair produces a 126 bp product. PCR products labeled with 32p can be conveniently detected by adding 5 μl of a formamide/dye mixture to the products, heating the products to denature the nucleic acids, separating the products by 6% urea polyacrylamide gel electrophoresis, and then exposing a PhosphorImager™ cassette or X-ray film to the gel.

The invention has been described in terms of preferred embodiments and illustrated by way of example and is claimed below.

What is claimed is:

1. A purified, synthetic or recombinant peptide, containing the amino acid sequence of SEQ. ID NO:2 (TPC2) or SEQ. ID NO:4 (TPC3), or an enzymatically active fragment thereof.

2. The peptide of claim 1 containing the amino acid sequence of SEQ. ID NO:2.

3. The peptide of claim 1 containing the amino acid sequence of SEQ. ID NO:4.

4. The peptide of claim 1 containing an enzymatically active fragment of SEQ. ID NO:2.

5. The peptide of claim 1 containing an enzymatically active fragment of SEQ. ID NO:4.

6. The peptide of claim 1, comprising the sequence RGLKRQSDERKRDRE (SEQ. ID NO:17) or KVTSPLQSPTKAKPK (SEQ. ID NO:18).

7. The peptide of claim 1, comprising the sequence LAMCTNLPEARVQVW FKNRRAKFR (SEQ. ID NO:10) or SSSKVHSFGKRDQAIRRNPNVPVVV (SEQ. ID NO:11).

8. The peptide of claim 1, comprising the sequence WSYGVCR DGRVFFINDQLRCTTWLHP (SEQ. ID NO:13), WFVLADYCLFYYKAEKKR SSXSIP (SEQ. ID NO:14), or WEEGFTEEGASYFIDHNQQTTAFRHP (SEQ. ID NO:15).

9. The peptide of claim 1, comprising at least 25 contiguous amino acids of SEQ. ID NOs:2 or 4.

10. The peptide of claim 1 that is a fusion peptide.

11. The fusion protein of claim 10 that has maltose binding activity.

12. A method for obtaining a peptide according to claim 2, comprising combining a sample containing the peptide with an antibody specific for a peptide according to claim 2, and recovering peptide bound to the antibody.

13. A method for obtaining a peptide according to claim 3, comprising combining a sample containing the peptide with an antibody specific for a peptide according to claim 3, and recovering peptide bound to the antibody.

14. A method for obtaining a peptide according to claim 4, comprising combining a sample containing the peptide with an antibody specific for a peptide according to claim 4, and recovering peptide bound to the antibody.

15. A method for obtaining a peptide according to claim 5, comprising combining a sample containing the peptide with an antibody specific for a peptide according to claim 3, and recovering peptide bound to the antibody.

* * * * *

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
         (A) LENGTH: 4232 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: CDS
         (B) LOCATION: 1..3315
         (D) OTHER INFORMATION: /product= "TPC2"

(ix) FEATURE:
         (A) NAME/KEY: unsure
         (B) LOCATION: 651
         (D) OTHER INFORMATION: /note= "N = probably C"

(ix) FEATURE:
         (A) NAME/KEY: unsure
         (B) LOCATION: 660
         (D) OTHER INFORMATION: /note= "N = probably C"

(ix) FEATURE:
         (A) NAME/KEY: unsure
         (B) LOCATION: 1142
         (D) OTHER INFORMATION: /note= "N = probably T"

(ix) FEATURE:
         (A) NAME/KEY: unsure
         (B) LOCATION: 1160
         (D) OTHER INFORMATION: /note= "N = maybe G"

(ix) FEATURE:
         (A) NAME/KEY: unsure
         (B) LOCATION: 1188
         (D) OTHER INFORMATION: /note= "N = probably G"

(ix) FEATURE:
         (A) NAME/KEY: unsure
         (B) LOCATION: 1211
         (D) OTHER INFORMATION: /note= "N = probably C"

(ix) FEATURE:
         (A) NAME/KEY: unsure
         (B) LOCATION: 1225
         (D) OTHER INFORMATION: /note= "N = probably G"

(ix) FEATURE:
         (A) NAME/KEY: unsure
         (B) LOCATION: 1230
         (D) OTHER INFORMATION: /note= "N = probably G"

(ix) FEATURE:
         (A) NAME/KEY: unsure
         (B) LOCATION: 1238
         (D) OTHER INFORMATION: /note= "N = probably C"

(ix) FEATURE:
         (A) NAME/KEY: unsure
         (B) LOCATION: 1247
         (D) OTHER INFORMATION: /note= "N = probably A"

(ix) FEATURE:
         (A) NAME/KEY: unsure
         (B) LOCATION: 1301
         (D) OTHER INFORMATION: /note= "N = probably G"

(ix) FEATURE:

```
          (A) NAME/KEY: unsure
          (B) LOCATION: 1375
          (D) OTHER INFORMATION: /note= "N = probably C"

(ix) FEATURE:
          (A) NAME/KEY: unsure
          (B) LOCATION: 1379
          (D) OTHER INFORMATION: /note= "N = probably C"

(ix) FEATURE:
          (A) NAME/KEY: unsure
          (B) LOCATION: 1391
          (D) OTHER INFORMATION: /note= "N = probably C"

(ix) FEATURE:
          (A) NAME/KEY: unsure
          (B) LOCATION: 1407
          (D) OTHER INFORMATION: /note= "N = probably C"

(ix) FEATURE:
          (A) NAME/KEY: unsure
          (B) LOCATION: 1530
          (D) OTHER INFORMATION: /note= "N = probably G"

(ix) FEATURE:
          (A) NAME/KEY: unsure
          (B) LOCATION: 1543
          (D) OTHER INFORMATION: /note= "N = probably G"

(ix) FEATURE:
          (A) NAME/KEY: unsure
          (B) LOCATION: 1545
          (D) OTHER INFORMATION: /note= "N = probably G"

(ix) FEATURE:
          (A) NAME/KEY: unsure
          (B) LOCATION: 1586
          (D) OTHER INFORMATION: /note= "N = probably G"

(ix) FEATURE:
          (A) NAME/KEY: unsure
          (B) LOCATION: 1588
          (D) OTHER INFORMATION: /note= "N = probably G"

(ix) FEATURE:
          (A) NAME/KEY: unsure
          (B) LOCATION: 1652
          (D) OTHER INFORMATION: /note= "N = probably G"

(ix) FEATURE:
          (A) NAME/KEY: unsure
          (B) LOCATION: 1685
          (D) OTHER INFORMATION: /note= "N = probably C"

(ix) FEATURE:
          (A) NAME/KEY: unsure
          (B) LOCATION: 1688
          (D) OTHER INFORMATION: /note= "N = probably G"

(ix) FEATURE:
          (A) NAME/KEY: unsure
          (B) LOCATION: 1707
          (D) OTHER INFORMATION: /note= "N = probably C"

(ix) FEATURE:
          (A) NAME/KEY: unsure
          (B) LOCATION: 1719
          (D) OTHER INFORMATION: /note= "N = probably C"

(ix) FEATURE:
          (A) NAME/KEY: unsure
          (B) LOCATION: 1725
          (D) OTHER INFORMATION: /note= "N = probably C"

(ix) FEATURE:
          (A) NAME/KEY: unsure
          (B) LOCATION: 1734
          (D) OTHER INFORMATION: /note= "N = probably C"
```

(ix) FEATURE:
             (A) NAME/KEY: unsure
             (B) LOCATION: 1789
             (D) OTHER INFORMATION: /note= "N = probably G"

(ix) FEATURE:
             (A) NAME/KEY: unsure
             (B) LOCATION: 1796
             (D) OTHER INFORMATION: /note= "N = probably A"

(ix) FEATURE:
             (A) NAME/KEY: unsure
             (B) LOCATION: 1816
             (D) OTHER INFORMATION: /note= "N = probably G"

(ix) FEATURE:
             (A) NAME/KEY: unsure
             (B) LOCATION: 1824
             (D) OTHER INFORMATION: /note= "N = probably G"

(ix) FEATURE:
             (A) NAME/KEY: unsure
             (B) LOCATION: 1929
             (D) OTHER INFORMATION: /note= "N = probably G"

(ix) FEATURE:
             (A) NAME/KEY: unsure
             (B) LOCATION: 1935
             (D) OTHER INFORMATION: /note= "N = maybe C"

(ix) FEATURE:
             (A) NAME/KEY: unsure
             (B) LOCATION: 1941
             (D) OTHER INFORMATION: /note= "N = probably G"

(ix) FEATURE:
             (A) NAME/KEY: unsure
             (B) LOCATION: 3828
             (D) OTHER INFORMATION: /note= "N = maybe A"

(xi) SEQUENCE DESCRIPTION: SEQ ID NO:1:

CCGCGCTCGG CGAACATGGC GGCGGCGACG GTCGGGCGGG ACACTTTACC TGAGCATTGG      60

TCCTACGGGG TGTGCCGGGA TGGCCGCGTC TTCTTCATCA ATGACCAGCT CCGCTGCACG     120

ACCTGGCTGC ACCCGCGCAC CGGGGAGCCC GTCAACTCGG GCCACATGAT CCGCTCAGAC     180

CTGCCCCGCG GCTGGGAGGA GGGCTTCACG GAGGAGGGCG CCAGCTACTT CATCGACCAT     240

AACCAGCAGA CCACAGCATT CAGGCATCCT GTGACGGGAC AGTTTTCTCC AGAAAATAGT     300

GAATTCATTC TTCAAGAAGA GCCGAATCCA CATATGTCGA AGCAAGACAG AAACCAAAGA     360

CCGTCCAGCA TGGTCAGTGA ACATCCACG GCTGGGACCG CCTCCACCCT GGAGGCCAAG      420

CCTGGACCCA AGATCATAAA GTCCAGCAGT AAAGTCCACA GCTTTGGGAA GAGAGACCAG     480

GCCATTCGGA GGAACCCCAA TGTTCCCGTG GTGGTGAGGG GCTGGCTGCA CAAGCAGGAC     540

AGTTYTGGGA TGAGGCTGTG GAAAAGGAGG TGGTTTGTGC TTGCTGATTA CTGCTTATTT     600

TACTATAAAG CCGAGAAGAA GCGGTCCTCG NGGAGCATCC CCTTGCCCAG NTACGTGATN     660

TCTCCTGTGG CCCCTGAGGA TCGCATAAGC CGCAAATATT CCTTTAAGGC TGTGCACACG     720

GGGATGCGAG CGCTCATCTA TAACAGCTCC ACAGCGGGCT CTCAGGCCGA GCAGTCAGGC     780

ATGAGGACCT ACTACTTCAG TGCCGACACC CAGGAGGACA TGAACGCTTG GGTCAGGGCC     840

ATGAACCAGG CTGCACAGGT GCTGTCTCGA TCGTCACTGA AGAGGGATAT GGAGAAGGTG     900

GAGCGGCAGG CTGTCCCCCA GGCCAACCAC ACAGAGTCCT GTCACGAATG TGGCCGGGTG     960

GGACCCGGAC ATACGAGAGA TTGTCCTCAT CGTGGCCATG ATGACATTGT CAACTTCGAG    1020

AGGCAGGAGC AGGAGGGAGA GCAGTACCGT TCCCAGAGGG ACCCACTGGA GGGCAAGCGG    1080

GACCGGAGCA AGGCCAGGTC TCCGTACTCG CCAGCCGAGG AGGATGCCTT GTTTATGGAT    1140

-continued

```
TNACCCAYTG GCCCAAGAGN CCAGCAGGCA CAGCCCCAAC GGGCAGANAA RAATGGAATG    1200

CTGCCTGCYT NATATGGCCC AGGANAACAN AATGGGANTG GTGGGTNCCA GCGGGCYTTT    1260

CYTCCCAGGA CCAACCYTGA AAAACACAGC CAAAGGAAGA NCAATCTGGC CCAGGTGGAG    1320

CACTGGGCAA GGGCCCAGAA AGGGGATAGC AGGAGTCTTC CCTTGGACCA GACGNTTCNT    1380

CGCCAGGGTC NTGGCCAATC CCTGTCNTTC CCAGAAAACT ACCAGAYTYT TCCCAAGAGC    1440

ACCCGACACC CCTCGGGGGG YTCYTCGCCA CYTCCCCGAA ACCTGCCAAG TGACTACAAG    1500

TATGCGCAGG ACCGAGCCAG CCACCTGAAN ATGTCGAGTG AANANCGCCG NGGCGCACCG    1560

GGATGGCACC GTGTGGCAGY TCTACNANTG GCAGCAGCGC CAGCAGTTCC GGCACGGCAG    1620

CCCCACAGCG CCCATCTGCC TTGGCTCCCC ANAGTTCACC GACCAGGGCC GGAGCAGGAG    1680

CATGNTANAG GTGCCCCGCT CCATYTNTGT GCCTCCATNT CCYTNGGACA TCCNTCCCCC    1740

AGGACCCCCA AGGGTYTTCC CACCCCGGCG GCCACACACA CCAGCAGANC GAGTCNCAGT    1800

GAAGCCACCG GACCANARGA RGANTGTGGA CATCTCCCTG GGGGATTCTC CATGGGTTAC    1860

ATGAMCCACA CCGTCAGCGC TCCCAGTTTA CATGGAAAAT CGGCTGATGA TACCTACCTC    1920

CAGCTGAANA AARANCTGGA NTACCTGGAT CTAAAGATGA CAGGCCGGGA CCTTCTCAAG    1980

GATCGAAGTC TGAAGCCTGT GAAGATCGCT GAGAGCGACA CTGACGTCAA ACTGAGCATC    2040

TTCTGTGAAC AAGACAGGGT CCTCCAGGAC TTGGAAGACA AGATACGAGC CCTTAAAGAG    2100

AACAAAGACC AGCTAGAATC TGTGCTGGAG GTGTTGCACA GACAGATGGA GCAGTACCGA    2160

GACCAGCCCC AGCACTTGGA GAAGATTGCC TACCAGCAGA AGTTGCTGCA GGAGGACCTT    2220

GTCCATATCC GAGCTGAGCT CTCCAGAGAG TCCACTGAGA TGGAAAATGC TTGGAACGAA    2280

TACCTGAAGT TGGAGAATGA TGTGGAACAG CTGAAGCAGA CCCTGCAGGA GCAACACAGA    2340

AGAGCCTTTT TTTTCCAGGA GAAATCGCAG ATACAGAAAG ATCTATGGAG AATTGAAGAT    2400

GTCACTGCAG GCCTGAGTGC AAATAAAGAG AACTTCAGAA TTCTAGTGGA GTCAGTAAAA    2460

AATCCGGAGA GAAAAACGGT GCCTTTGTTT CCTCACCCGC CTGTGCCTTC ACTCTCAACT    2520

TCTGAGAGCA AGCCGCCCCC ACAGCCCAGT CCTCCCACCA GCCCTGTGCG GACCCCTCTG    2580

GAGGTTCGAC TCTTCCCCCA GCTGCAAACC TACGTGCCGT ACCGACCTCA CCCACCCCAG    2640

CTGAGGAAAG TGACATCCCC CCTTCAGTCA CCAACTAAGG CGAAGCCCAA AGTTCAGGAA    2700

GATGAAGCAC CTCCCAGGCC CCCACTCCCC GAACTCTACA GCCCAGAGGA CCAGCCCCCG    2760

GCTGTGCCGC CTCTGCCAAG AGAGGCCACC ATCATCCGGC ACACATCTGT GCGGGCCTC    2820

AAGCGGCAGT CAGACGAGAG GAAGCGAGAC CGGGAGCTGG GGCAGTGTGT GAATGGGGAT    2880

TCCAGGGTGG AGCTGCGGTC GTATGTCAGT GAGCCTGAGC TGGCGACCCT CAGCGGGGAC    2940

ATGGCCCAGC CCTCCCTAGG ACTTGTGGGC CCTGAGAGCA GGTACCAGAC GCTGCCAGGC    3000

AGAGGGCTCT CAGGGTCCAC GTCAAGGCTC CAGCAGTCGT CCACCATTGC TCCCTACGTC    3060

ACACTCCGGA GGGGTCTCAA TGCCGAAAGC AGCAAGGCGA CCTTCCCTAG ACCTAAGAGT    3120

GCCTTGGAGC GCCTGTACTC AGGGGATCAC CAGCGAGGCA AGATGAGTGC AGAGGAGCAG    3180

CTGGAGCGCA TGAAGCGACA CCAGAAGGCC CTGGTCCGAG AGCGCAAGAG GACACTGGGC    3240

CAAGGGGAGA GGACGGGCCT GCCCTCATCT CGCTACCTCA GCCGGCCGCT CCCTGGAGAT    3300

CTTGGCTCAG TATGTTAGGA GGGGCCAGGC AGCGGGGCAG GGACAGGGAG CCGAGTGCCC    3360

CTCAGAGTCC CCCAAACACA AGCACATCAC ACCTCCCAGT GAGAGAGCTG TCCATTGACC    3420

TACATGGTTC AGAGAACACC CCACGGGGCT GTTTGTCCAC GACCCAGGCT GGACGAATGC    3480
```

```
CTGGTCAGAG GGTGACCTGA ACCAGAGCTG GAGTGAGGAT CAAACAGGCC CAGGAGCCTG    3540

AGGAAATACC CAGTCAGTCC TCCCAGCCGC GATGGAGAGG GGCCTTTGCA GGCGTTCGGA    3600

ATCTCGGCTG AATTCAGGAC CTGGGAATAC AGGGTTCAGA GAGGAGAGGA GGAAGATGGT    3660

GACATGATTT GGTTAGAAGC ACAAGCAAAC TGATCAGCCT CCCAGACCTG CCAGCAGATG    3720

CTGTGTGAGG GTGATGGAGC ACGGGGTCAC ACCCCTGCCC CAAGGGCCAC TGGTCTCCCT    3780

GGGCTTGCAG TGCAGAGGCC TCAGGGTGTC TGGGATTGCT GGGGAGGNCT GTGCTGCCCC    3840

CTGGTGGCGC TTCCTGGCGC TGCGCCCTGT CCACAGTCAC CTTAGGACCC TTTGGAAACA    3900

TTCCATTTGA CTTTTCCCTG TTGYTTGAAA TCCCATGTTT CCCTAAACCT CTAGCCTGAT    3960

TGTTCTTTCC CTAATTCATT GCACAAGCTC CTTTGCTTTT AGTGTTACCG CTCATTGCCT    4020

CTCTAATCCT GCCTGATTGT GTTTACAGAA GCTTCTGATT TGCATTGAAC ATGCTCTAAC    4080

TGGCCTGTGC TACTTATTAC CGGGCTTGTA ATAGCGGTTC TTGTCTCCAT AGCCTGTTGA    4140

GTGTTCCCAG ATGTGACTCA CCTTTCTGCT GCCCTCTTCA TGCAGGCCTA CTGACTCATA    4200

ATTCACTTGT CCGTCGACGC GGCCGCGAAT TC                                  4232
```

(2) INFORMATION FOR SEQ ID NO:2:

(i) SEQUENCE CHARACTERISTICS:
        (A) LENGTH: 1105 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..1105
        (D) OTHER INFORMATION: /note= "deduced amino acid sequence of
            TPC2 open reading frame"

(xi) SEQUENCE DESCRIPTION: SEQ ID NO:2:

```
Pro Arg Ser Ala Asn Met Ala Ala Ala Thr Val Gly Arg Asp Thr Leu
1               5                   10                  15

Pro Glu His Trp Ser Tyr Gly Val Cys Arg Asp Gly Arg Val Phe Phe
            20                  25                  30

Ile Asn Asp Gln Leu Arg Cys Thr Thr Trp Leu His Pro Arg Thr Gly
        35                  40                  45

Glu Pro Val Asn Ser Gly His Met Ile Arg Ser Asp Leu Pro Arg Gly
    50                  55                  60

Trp Glu Glu Gly Phe Thr Glu Gly Ala Ser Tyr Phe Ile Asp His
65                  70                  75                  80

Asn Gln Gln Thr Thr Ala Phe Arg His Pro Val Thr Gly Gln Phe Ser
            85                  90                  95

Pro Glu Asn Ser Glu Phe Ile Leu Gln Glu Glu Pro Asn Pro His Met
            100                 105                 110

Ser Lys Gln Asp Arg Asn Gln Arg Pro Ser Ser Met Val Ser Glu Thr
        115                 120                 125

Ser Thr Ala Gly Thr Ala Ser Thr Leu Glu Ala Lys Pro Gly Pro Lys
    130                 135                 140

Ile Ile Lys Ser Ser Ser Lys Val His Ser Phe Gly Lys Arg Asp Gln
145                 150                 155                 160

Ala Ile Arg Arg Asn Pro Asn Val Pro Val Val Arg Gly Trp Leu
            165                 170                 175

His Lys Gln Asp Ser Xaa Gly Met Arg Leu Trp Lys Arg Arg Trp Phe
```

-continued

```
                180                 185                 190
Val Leu Ala Asp Tyr Cys Leu Phe Tyr Tyr Lys Ala Glu Lys Lys Arg
            195                 200                 205
Ser Ser Xaa Ser Ile Pro Leu Pro Xaa Tyr Val Xaa Ser Pro Val Ala
        210                 215                 220
Pro Glu Asp Arg Ile Ser Arg Lys Tyr Ser Phe Lys Ala Val His Thr
225                 230                 235                 240
Gly Met Arg Ala Leu Ile Tyr Asn Ser Ser Thr Ala Gly Ser Gln Ala
            245                 250                 255
Glu Gln Ser Gly Met Arg Thr Tyr Tyr Phe Ser Ala Asp Thr Gln Glu
                260                 265                 270
Asp Met Asn Ala Trp Val Arg Ala Met Asn Gln Ala Ala Gln Val Leu
            275                 280                 285
Ser Arg Ser Ser Leu Lys Arg Asp Met Glu Lys Val Glu Arg Gln Ala
        290                 295                 300
Val Pro Gln Ala Asn His Thr Glu Ser Cys His Glu Cys Gly Arg Val
305                 310                 315                 320
Gly Pro Gly His Thr Arg Asp Cys Pro His Arg Gly His Asp Asp Ile
            325                 330                 335
Val Asn Phe Glu Arg Gln Glu Gln Glu Gly Glu Gln Tyr Arg Ser Gln
                340                 345                 350
Arg Asp Pro Leu Glu Gly Lys Arg Asp Arg Ser Lys Ala Arg Ser Pro
            355                 360                 365
Tyr Ser Pro Ala Glu Glu Asp Ala Leu Phe Met Asp Xaa Pro Xaa Gly
        370                 375                 380
Pro Arg Xaa Gln Gln Ala Gln Pro Gln Arg Ala Xaa Lys Asn Gly Met
385                 390                 395                 400
Leu Pro Xaa Xaa Tyr Gly Pro Gly Xaa Xaa Asn Gly Xaa Gly Gly Xaa
            405                 410                 415
Gln Arg Xaa Phe Xaa Pro Arg Thr Asn Xaa Glu Lys His Ser Gln Arg
                420                 425                 430
Lys Xaa Asn Leu Ala Gln Val Glu His Trp Ala Arg Ala Gln Lys Gly
            435                 440                 445
Asp Ser Arg Ser Leu Pro Leu Asp Gln Thr Xaa Xaa Arg Gln Gly Xaa
        450                 455                 460
Gly Gln Ser Leu Xaa Phe Pro Glu Asn Tyr Gln Xaa Xaa Pro Lys Ser
465                 470                 475                 480
Thr Arg His Pro Ser Gly Xaa Xaa Ser Pro Xaa Pro Arg Asn Leu Pro
            485                 490                 495
Ser Asp Tyr Lys Tyr Ala Gln Asp Arg Ala Ser His Leu Xaa Met Ser
                500                 505                 510
Ser Glu Xaa Arg Xaa Gly Ala Pro Gly Trp His Arg Val Ala Xaa Leu
            515                 520                 525
Xaa Xaa Ala Ala Ala Pro Ala Val Pro Ala Arg Gln Pro His Ser Ala
        530                 535                 540
His Leu Pro Trp Leu Pro Xaa Val His Arg Pro Gly Pro Glu Gln Glu
545                 550                 555                 560
His Xaa Xaa Gly Ala Pro Leu His Xaa Cys Ala Ser Xaa Ser Xaa Gly
            565                 570                 575
His Xaa Ser Pro Arg Thr Pro Lys Gly Xaa Pro Thr Pro Ala Ala Thr
        580                 585                 590
His Thr Ser Arg Xaa Ser Xaa Ser Glu Ala Thr Gly Pro Xaa Glu Xaa
            595                 600                 605
```

-continued

```
Cys Gly His Leu Pro Gly Gly Phe Ser Met Gly Tyr Met Xaa His Thr
    610                 615                 620
Val Ser Ala Pro Ser Leu His Gly Lys Ser Ala Asp Asp Thr Tyr Leu
625                 630                 635                 640
Gln Leu Xaa Lys Xaa Leu Xaa Tyr Leu Asp Leu Lys Met Thr Gly Arg
                645                 650                 655
Asp Leu Leu Lys Asp Arg Ser Leu Lys Pro Val Lys Ile Ala Glu Ser
                660                 665                 670
Asp Thr Asp Val Lys Leu Ser Ile Phe Cys Glu Gln Asp Arg Val Leu
            675                 680                 685
Gln Asp Leu Glu Asp Lys Ile Arg Ala Leu Lys Glu Asn Lys Asp Gln
    690                 695                 700
Leu Glu Ser Val Leu Glu Val Leu His Arg Gln Met Glu Gln Tyr Arg
705                 710                 715                 720
Asp Gln Pro Gln His Leu Glu Lys Ile Ala Tyr Gln Gln Lys Leu Leu
                725                 730                 735
Gln Glu Asp Leu Val His Ile Arg Ala Glu Leu Ser Arg Glu Ser Thr
                740                 745                 750
Glu Met Glu Asn Ala Trp Asn Glu Tyr Leu Lys Leu Glu Asn Asp Val
    755                 760                 765
Glu Gln Leu Lys Gln Thr Leu Gln Glu Gln His Arg Arg Ala Phe Phe
770                 775                 780
Phe Gln Glu Lys Ser Gln Ile Gln Lys Asp Leu Trp Arg Ile Glu Asp
785                 790                 795                 800
Val Thr Ala Gly Leu Ser Ala Asn Lys Glu Asn Phe Arg Ile Leu Val
                805                 810                 815
Glu Ser Val Lys Asn Pro Glu Arg Lys Thr Val Pro Leu Phe Pro His
                820                 825                 830
Pro Pro Val Pro Ser Leu Ser Thr Ser Glu Ser Lys Pro Pro Pro Gln
            835                 840                 845
Pro Ser Pro Pro Thr Ser Pro Val Arg Thr Pro Leu Glu Val Arg Leu
850                 855                 860
Phe Pro Gln Leu Gln Thr Tyr Val Pro Tyr Arg Pro His Pro Pro Gln
865                 870                 875                 880
Leu Arg Lys Val Thr Ser Pro Leu Gln Ser Pro Thr Lys Ala Lys Pro
                885                 890                 895
Lys Val Gln Glu Asp Glu Ala Pro Arg Pro Pro Leu Pro Glu Leu
                900                 905                 910
Tyr Ser Pro Glu Asp Gln Pro Ala Val Pro Pro Leu Pro Arg Glu
            915                 920                 925
Ala Thr Ile Ile Arg His Thr Ser Val Arg Gly Leu Lys Arg Gln Ser
    930                 935                 940
Asp Glu Arg Lys Arg Asp Arg Glu Leu Gly Gln Cys Val Asn Gly Asp
945                 950                 955                 960
Ser Arg Val Glu Leu Arg Ser Tyr Val Ser Glu Pro Glu Leu Ala Thr
                965                 970                 975
Leu Ser Gly Asp Met Ala Gln Pro Ser Leu Gly Leu Val Gly Pro Glu
            980                 985                 990
Ser Arg Tyr Gln Thr Leu Pro Gly Arg Gly Leu Ser Gly Ser Thr Ser
    995                 1000                1005
Arg Leu Gln Gln Ser Ser Thr Ile Ala Pro Tyr Val Thr Leu Arg Arg
    1010                1015                1020
```

```
Gly Leu Asn Ala Glu Ser Ser Lys Ala Thr Phe Pro Arg Pro Lys Ser
1025                1030                1035                1040

Ala Leu Glu Arg Leu Tyr Ser Gly Asp His Gln Arg Gly Lys Met Ser
                1045                1050                1055

Ala Glu Glu Gln Leu Glu Arg Met Lys Arg His Gln Lys Ala Leu Val
            1060                1065                1070

Arg Glu Arg Lys Arg Thr Leu Gly Gln Gly Arg Thr Gly Leu Pro
        1075                1080                1085

Ser Ser Arg Tyr Leu Ser Arg Pro Leu Pro Gly Asp Leu Gly Ser Val
        1090                1095                1100

Cys
1105

(2) INFORMATION FOR SEQ ID NO:3:

(i) SEQUENCE CHARACTERISTICS:
        (A) LENGTH: 4080 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 79..1380
        (D) OTHER INFORMATION: /product= "TPC3"

(xi) SEQUENCE DESCRIPTION: SEQ ID NO:3:

GGAAACGCAG TTTAAAACTC CAGCCCAGGC CCCGTCGCGC GTAGATGGCA GCGGAGGCGG      60

CGGCGCGGGC CGGGGTGA CCA GAT CCC GTT CAA ACT CAG CTG CCA CCA AGT       111
                    Pro Asp Pro Val Gln Thr Gln Leu Pro Pro Ser
                     1               5                  10

GCG CCT TTT CTC TCT GGA TTG CGA TTC TGC ACG AAT TTT CCA GTT GAG       159
Ala Pro Phe Leu Ser Gly Leu Arg Phe Cys Thr Asn Phe Pro Val Glu
            15                  20                  25

GGT GGT TCG GCG CTC AGC CAG CCT CTG CCC TCG AAG ACG CGG CCT TGG       207
Gly Gly Ser Ala Leu Ser Gln Pro Leu Pro Ser Lys Thr Arg Pro Trp
        30                  35                  40

TCT AGG AAC CTT CAG GCG GAT GCC GCC ATG CAG CAC TAC GGG GTG AAC       255
Ser Arg Asn Leu Gln Ala Asp Ala Ala Met Gln His Tyr Gly Val Asn
    45                  50                  55

GGC TAC TCA CTG CAC GCC ATG AAC TCA CTC AGC GCC ATG TAC AAC CTG       303
Gly Tyr Ser Leu His Ala Met Asn Ser Leu Ser Ala Met Tyr Asn Leu
60                  65                  70                  75

CAC CAG CAG GCA GCC CAG CAG GCC CAG CAT GCC CCC GAC TAC CGG CCT       351
His Gln Gln Ala Ala Gln Gln Ala Gln His Ala Pro Asp Tyr Arg Pro
                80                  85                  90

TCA GTG CAT GCG CTT ACA TTG GCT GAG CGC CTG GCT GGC TGT ACA TTT       399
Ser Val His Ala Leu Thr Leu Ala Glu Arg Leu Ala Gly Cys Thr Phe
            95                  100                 105

CAA GAC ATC ATC TTG GAG GCC CGT TAT GGT TCC CAG CAC CGC AAA CAA       447
Gln Asp Ile Ile Leu Glu Ala Arg Tyr Gly Ser Gln His Arg Lys Gln
        110                 115                 120

CGT CGC AGC CGC ACA GCG TTC ACG GCT CAG CAG CTC GAG GCC CTG GAA       495
Arg Arg Ser Arg Thr Ala Phe Thr Ala Gln Gln Leu Glu Ala Leu Glu
    125                 130                 135

AAG ACC TTC CAG AAG ACT CAC TAC CCA GAT GTG GTG ATG CGT GAG AGG       543
Lys Thr Phe Gln Lys Thr His Tyr Pro Asp Val Val Met Arg Glu Arg
140                 145                 150                 155

CTG GCC ATG TGC ACC AAC CTG CCT GAG GCC CGG GTG CAG GTG TGG TTC       591
```

```
                                                                  -continued
Leu Ala Met Cys Thr Asn Leu Pro Glu Ala Arg Val Gln Val Trp Phe
            160                 165                 170

AAG AAC CGC CGG GCC AAG TTC CGG AAG AAG CAG CGT AGC CTG CAG AAG          639
Lys Asn Arg Arg Ala Lys Phe Arg Lys Lys Gln Arg Ser Leu Gln Lys
            175                 180                 185

GAA CAG CTC CAG AAG CAG AAG GAG GCT GAG GGC TCC CAT GGG GAA GGC          687
Glu Gln Leu Gln Lys Gln Lys Glu Ala Glu Gly Ser His Gly Glu Gly
            190                 195                 200

AAG GCC GAG GCC CCC ACT CCA GAT ACC CAG CTG GAC ACT GAG CAG CCC          735
Lys Ala Glu Ala Pro Thr Pro Asp Thr Gln Leu Asp Thr Glu Gln Pro
    205                 210                 215

CCA CGT CTG CCT GGC AGC GAC CCC CCT GCT GAG CTT CAC CTG AGT CTG          783
Pro Arg Leu Pro Gly Ser Asp Pro Pro Ala Glu Leu His Leu Ser Leu
220                 225                 230                 235

TCT GAG CAG TCA GCC AGT GAG TCA GCC CCT GAG GAT CAG CCG GAC CGT          831
Ser Glu Gln Ser Ala Ser Glu Ser Ala Pro Glu Asp Gln Pro Asp Arg
                240                 245                 250

GAG GAG GAC CCC AGG GCA GGG GCT GAG GAC CCC AAA GCT GAG AAG AGC          879
Glu Glu Asp Pro Arg Ala Gly Ala Glu Asp Pro Lys Ala Glu Lys Ser
                255                 260                 265

CCT GGG GCT GAC AGC AAG GGG CTG GGC TGC AAG AGG GGC AGC CCC AAG          927
Pro Gly Ala Asp Ser Lys Gly Leu Gly Cys Lys Arg Gly Ser Pro Lys
            270                 275                 280

GCA GAT TCC CCA GGC AGC CTG ACC ATC ACT CCT GTG GCC CCA GGG GGT          975
Ala Asp Ser Pro Gly Ser Leu Thr Ile Thr Pro Val Ala Pro Gly Gly
            285                 290                 295

GGC CTC CTG GGC CCC TCC CAC TCC TAT TCC TCG TCC CCG CTG AGC CTC         1023
Gly Leu Leu Gly Pro Ser His Ser Tyr Ser Ser Ser Pro Leu Ser Leu
300                 305                 310                 315

TTC CGT CTG CAG GAG CAA TTC CGC CAG CAT ATG GCG GCC ACC AAC AAC         1071
Phe Arg Leu Gln Glu Gln Phe Arg Gln His Met Ala Ala Thr Asn Asn
                320                 325                 330

CTG GTG CAC TAC TCG TCC TTC GAA GTA GGG GGT CCG GCC CCT GCT GCT         1119
Leu Val His Tyr Ser Ser Phe Glu Val Gly Gly Pro Ala Pro Ala Ala
                335                 340                 345

GCA GCG GCG GCT GCT GCT GTG CCC TAC CTG GGC GTC AAC ATG GCC CCG         1167
Ala Ala Ala Ala Ala Ala Val Pro Tyr Leu Gly Val Asn Met Ala Pro
            350                 355                 360

CTG GGC TCA CTG CAC TGC AGG TCC TAC TAC CAG TCC CTG TCA GCA GCC         1215
Leu Gly Ser Leu His Cys Gln Ser Tyr Tyr Gln Ser Leu Ser Ala Ala
    365                 370                 375

GCT GCT GCC CAC CAG GGT GTG TGG GGG TCT CCT CTG CTG CCT GCA CCC         1263
Ala Ala Ala His Gln Gly Val Trp Gly Ser Pro Leu Leu Pro Ala Pro
380                 385                 390                 395

CCA GCA GGC CTG GCT CCT GCA TCA GCT ACC CTG AAC AGT AAA ACC ACA         1311
Pro Ala Gly Leu Ala Pro Ala Ser Ala Thr Leu Asn Ser Lys Thr Thr
                400                 405                 410

AGC ATC GAG AAC CTG CGG CTC CGG GCC AAG CAG CAC GCG GCC TCC CTG         1359
Ser Ile Glu Asn Leu Arg Leu Arg Ala Lys Gln His Ala Ala Ser Leu
                415                 420                 425

GGA CTC GAT ACG CTG CCC AAC TGACTGTCTG GCTTCCAACC CAGCCAGGGG            1410
Gly Leu Asp Thr Leu Pro Asn
            430

TCTTAGGTGT CCCCTCCTAG CCCTGTGGTT ATCCCTAGGT GGCTCTCGAG GAGTTAACTC       1470

CATGAGCCCA GGGATCCTAG GGCCTGGGGT CCTGTTCCCT GCTCCGCTTC CCCATACCCC       1530

AGCCCGAGGT GAAGCCCACA CCTACACACC CTCTGCATGG CCCTGCCTGG ACCCCATGGA       1590

GGCCGAATAG GGAGGAGGTG AGAGGCTGGG GTGCCCCAAG CTTCCCTCGG AGAAGTGAGA       1650
```

```
GGCTCTCCCT GGCTAGATCC TCATCTCAAT AGCACCTCCT CCCTTTTCTC CCTATCCTTC    1710

TGCCCCCTAG TAAGTCTACG TGTGGAATGT GAGATATAAA TATAAATATA TAAAGCTATA    1770

TTTTCAGGCT CCTGCCTGCC CCAGGCCCCC TGCCCCACTC CCATCTCTTC TTCCCTGCCA    1830

CCCCTCCCTG CAGCCTCCGC GGCTCACTCC AGCCATCCCT TCTGTTTCTC CTTCTCTCTC    1890

CTTCCTTCTT CCCTTGATCT CCCTCTTCCT GTCTCTGTCC TGGTCCCTGC CCCCGTCTCG    1950

GCCCAGCCTC TGTATTCTCC ACCCTTGATC TTTCTCCTTG TCTCTCCCGC TGCCCCTGGT    2010

TTCTTCCTTT GGTGTTGGCT GTGTTGGTAT CATCAGTTCT TGAGCTATAT TTTGTTTGGG    2070

GTTGTGGCTG GTTTTGGTTT TAGTAATTTT GCGACTTCCC GTTGCTCTCC TTCTATTCCC    2130

TTCCTTCTGC CCTGCCTGCC TCCCTGCACC TGCGGCCTCT CTAGGAAGCT GTTCCTTTCT    2190

ATGCCCAATA GAAGCAACAA GGCCCTAGCT GGAGACTCTG GGGATCTGGA GCTGCAGGCA    2250

GGAGGTGGCA CTGGCTCCCA CTCCCACCCC TGCCCAGGCT GGCATCTAGA AGGCGTCATG    2310

AATTACTTTC TCTTCTCTCT TCTCAATTTT GAGGTCCTCA TTCCCAAGAT TGAGGAGGCA    2370

GTAGTTAATC TGGGAAGGCA GTAGAATGGC CAGCATTCCT GCCTGTAAGT CTTCCCAAGA    2430

CAGAGGCCTG GTGACACAGT TCAGCCAGGA CTGACCACAG GGCTCTAGAG CTCTCTTTGG    2490

TGAGACTTCC CTGGATGGAG AGCAGCAGCA GGGGAAGAGG TGCTCTCAGA GACAGCAGGG    2550

CTGGTGCTCT TCTCCCACAA GCTGAGCTCC ACGTTCAGCA GATACTGTCC AAGGCAGGGG    2610

TACGGCTGAC CAGGAATGAA GGTTGAACTC TGCTCCTGAG CACGGTGCGT GCAAAGCATA    2670

TAGCAGCACA TAGGCTCAGG CTTCTGTAGG CTTCCTGTCC CAGAGCCAAT TATGGAAGTA    2730

AGGGCTTCCC TCCAGCTAGT CACTGGAATG GAAAAGTGTG TGTCCTGTTC ATAGCCAGGA    2790

AACCCAGCTC AGCAAACTCC CTTTCAAAGC TGTGTGACCG GCTGGGCATG GTGGCTCACA    2850

CCTGTAATCC CAGCACTTTG GGAGGCCAAG GCAGGCAATC ACCTGAGGTC AGGAGTTCAA    2910

GACCAGCCTG GCTAACATGT GAAACTAATA ATAATACAAA AATTAGCTGG GCGTGGTGGC    2970

ACATGCCTGT AATCCCAGCT ACTTGGGAGG CTGAGTTGGG AGGATTGCTG CAATCTGGGA    3030

GGTGGAAGTT GCAGTGAGCC GAGATCATGC CACTGCACTC CAGCCTGGGC GACGGAGTGA    3090

GACTCCATCT CAAAAAAAAA AAAATAAAA ATAAAAGCTG TGTGACCTTG GGCAABCCTG    3150

TAGCCTCTCT GGGTCTGTTT CCCTGTCTGG GTTAAATGGC CTGTAAGGTC CTAGCCAGCT    3210

CTACATTCTG CATTTGCTCG CAACCTTGTA ACACAGAAGT TTTTAGTTAA ATTGACAACA    3270

GAAGGTTCTC AAAAGCACAA TATATGAAGT AGGAAATTAC TATTGCCTTT CTGTGGAGCA    3330

AGGGGTGTTG TACACACAAG CCTCACTGTA GACACTGCCT CAGTTTCCCC ATAGGCATAA    3390

TGGGTCCCTT CTAGTTCAGG CAATCTGGAT TTGATCTTGA GTTCCAGTGC CAGCCTCTGG    3450

AGTCACTCCA TTTTCATACC TTTTCATGAT CTCAGGGCT CTGGGCAGTG GGAGGTGATG    3510

GCTTGGACAG ATTCTTGGTC ATGCTCCCCA ACTCTTGGTG GCTCACCACT GAACACTCCA    3570

AACCCTGCTT AAAGAAGTTG ATTTATTTGA AAGCCAGGGT AAAGATTGCT AAGGCTTGTC    3630

TCCTCTCCCA GTGGGAAGAG AGAGGTTCTG TTGGTGTCCT GGTTGAATTG CTTTGCAGAG    3690

AAGTCAATGC CCATCACCCT TGATGGGGGT CAGCCTAGGC TGGGGCAGAT GGAGAAGGCT    3750

TTGGACAGGA AAAAGTGAG CAGGATGGTA GTCTAGGCCA GGAGAAGTGT TTGAACAAAG    3810

CAGCAGAGAT GAGACTCAGT AGACCATGGG AAGGGGTGG CTGGCTTCAC GAGAGGTGGG    3870

GGCTAAGGGG CCTGGAATCC AGGCTAAAGA CCACACCTAC ATGTGGCAAG CACCAAGACA    3930

GGCATTTGAG GGTTTCCAAA TCCTCAGGTC TCTTGCTGGG GTCTGGAATT TGGAAGGGGA    3990

ATCCACCAGC CATGGGGGCA TCAGAGGAGA GACTTAGGCA GCGCTGTGGG AGGTTGGCAG    4050
```

ATTCCAGGAG TGACAGAGGA GGTTTTTGGT                                    4080

(2) INFORMATION FOR SEQ ID NO:4:

(i) SEQUENCE CHARACTERISTICS:
        (A) LENGTH: 434 amino acids
        (B) TYPE: amino acid
        (D) TOPOLOGY: linear (ii) MOLECULE TYPE: protein (xi) SEQUENCE DESCRIPTION: SEQ ID NO:4:

```
Pro Asp Pro Val Gln Thr Gln Leu Pro Pro Ser Ala Pro Phe Leu Ser
 1               5                  10                  15

Gly Leu Arg Phe Cys Thr Asn Phe Pro Val Glu Gly Gly Ser Ala Leu
             20                  25                  30

Ser Gln Pro Leu Pro Ser Lys Thr Arg Pro Trp Ser Arg Asn Leu Gln
         35                  40                  45

Ala Asp Ala Ala Met Gln His Tyr Gly Val Asn Gly Tyr Ser Leu His
     50                  55                  60

Ala Met Asn Ser Leu Ser Ala Met Tyr Asn Leu His Gln Gln Ala Ala
 65                  70                  75                  80

Gln Gln Ala Gln His Ala Pro Asp Tyr Arg Pro Ser Val His Ala Leu
                 85                  90                  95

Thr Leu Ala Glu Arg Leu Ala Gly Cys Thr Phe Gln Asp Ile Ile Leu
            100                 105                 110

Glu Ala Arg Tyr Gly Ser Gln His Arg Lys Gln Arg Ser Arg Thr
        115                 120                 125

Ala Phe Thr Ala Gln Gln Leu Glu Ala Leu Glu Lys Thr Phe Gln Lys
    130                 135                 140

Thr His Tyr Pro Asp Val Val Met Arg Glu Arg Leu Ala Met Cys Thr
145                 150                 155                 160

Asn Leu Pro Glu Ala Arg Val Gln Val Trp Phe Lys Asn Arg Arg Ala
                165                 170                 175

Lys Phe Arg Lys Lys Gln Arg Ser Leu Gln Lys Glu Gln Leu Gln Lys
            180                 185                 190

Gln Lys Glu Ala Glu Gly Ser His Gly Glu Gly Lys Ala Glu Ala Pro
        195                 200                 205

Thr Pro Asp Thr Gln Leu Asp Thr Glu Gln Pro Pro Arg Leu Pro Gly
    210                 215                 220

Ser Asp Pro Pro Ala Glu Leu His Leu Ser Leu Ser Glu Gln Ser Ala
225                 230                 235                 240

Ser Glu Ser Ala Pro Glu Asp Gln Pro Asp Arg Glu Glu Asp Pro Arg
                245                 250                 255

Ala Gly Ala Glu Asp Pro Lys Ala Glu Lys Ser Pro Gly Ala Asp Ser
            260                 265                 270

Lys Gly Leu Gly Cys Lys Arg Gly Ser Pro Lys Ala Asp Ser Pro Gly
        275                 280                 285

Ser Leu Thr Ile Thr Pro Val Ala Pro Gly Gly Leu Leu Gly Pro
    290                 295                 300

Ser His Ser Tyr Ser Ser Ser Pro Leu Ser Leu Phe Arg Leu Gln Glu
305                 310                 315                 320

Gln Phe Arg Gln His Met Ala Ala Thr Asn Asn Leu Val His Tyr Ser
                325                 330                 335

Ser Phe Glu Val Gly Gly Pro Ala Pro Ala Ala Ala Ala Ala Ala Ala
```

```
                340                 345                 350
Ala Val Pro Tyr Leu Gly Val Asn Met Ala Pro Leu Gly Ser Leu His
            355                 360                 365

Cys Gln Ser Tyr Tyr Gln Ser Leu Ser Ala Ala Ala Ala His Gln
            370                 375                 380

Gly Val Trp Gly Ser Pro Leu Leu Pro Ala Pro Pro Ala Gly Leu Ala
385                 390                 395                 400

Pro Ala Ser Ala Thr Leu Asn Ser Lys Thr Thr Ser Ile Glu Asn Leu
                405                 410                 415

Arg Leu Arg Ala Lys Gln His Ala Ala Ser Leu Gly Leu Asp Thr Leu
                420                 425                 430

Pro Asn (2) INFORMATION FOR SEQ ID NO:5:

(i) SEQUENCE CHARACTERISTICS:
        (A) LENGTH: 981 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_RNA
        (B) LOCATION: 267..715
        (D) OTHER INFORMATION: /product= "hTR"
            /note= "hTR transcript serves as
            template in the telomerase
            ribonucleoprotein"

(xi) SEQUENCE DESCRIPTION: SEQ ID NO:5:
```

| | | | | | |
|---|---|---|---|---|---|
| CTGCAGAGGA | TAGAAAAAAG | NCCCTCTGAT | ACCTCAAGTT | AGTTTCACCT | TTAAAGAAGG | 60 |
| TCGGAAGTAA | AGACGCAAAG | CCTTTCCCGG | ACGTGCGGAA | GGGCAACGTC | CTTCCTCATG | 120 |
| GCCGGAAATG | GAACTTTAAT | TTCCCGTTCC | CCCCAACCAG | CCCGCCCGAG | AGAGTGACTC | 180 |
| TCACGAGAGC | CGCGAGAGTC | AGCTTGGCCA | ATCCGTGCGG | TCGGCGGCCG | CTCCCTTTAT | 240 |
| AAGCCGACTC | GCCCGGCAGC | GCACCGGGTT | GCGGAGGGTG | GGCCTGGGAG | GGGTGGTGGC | 300 |
| CATTTTTTGT | CTAACCCTAA | CTGAGAAGGG | CGTAGGCGCC | GTGCTTTTGC | TCCCCGCGCG | 360 |
| CTGTTTTTCT | CGCTGACTTT | CAGCGGGCGG | AAAAGCCTCG | GCCTGCCGCC | TTCCACCGTT | 420 |
| CATTCTAGAG | CAAACAAAAA | ATGTCAGCTG | CTGGCCCGTT | CGCCCCTCCC | GGGGACCTGC | 480 |
| GGCGGGTCGC | CTGCCCAGCC | CCCGAACCCC | GCCTGGAGGC | CGCGGTCGGC | CCGGGGCTTC | 540 |
| TCCGGAGGCA | CCCACTGCCA | CCGCGAAGAG | TTGGGCTCTG | TCAGCCGCGG | GTCTCTCGGG | 600 |
| GGCGAGGGCG | AGGTTCAGGC | CTTTCAGGCC | GCAGGAAGAG | GAACGGAGCG | AGTCCCCGCG | 660 |
| CGCGGCGCGA | TTCCCTGAGC | TGTGGGACGT | GCACCCAGGA | CTCGGCTCAC | ACATGCAGTT | 720 |
| CGCTTTCCTG | TTGGTGGGGG | AACGCCGAT | CGTGCGCATC | CGTCACCCCT | CGCCGGCAGT | 780 |
| GGGGGCTTGT | GAACCCCCAA | ACCTGACTGA | CTGGGCCAGT | GTGCTGCAAA | TTGGCAGGAG | 840 |
| ACGTGAAGGC | ACCTCCAAAG | TCGGCCAAAA | TGAATGGGCA | GTGAGCCGGG | GTTGCCTGGA | 900 |
| GCCGTTCCTG | CGTGGGTTCT | CCCGTCTTCC | GCTTTTGTT | GCCTTTTATG | GTTGTATTAC | 960 |
| AACTTAGTTC | CTGCTCTGCA | G | | | | 981 |

```
(2) INFORMATION FOR SEQ ID NO:6:

(i) SEQUENCE CHARACTERISTICS:
        (A) LENGTH: 22 base pairs
```

(B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

ATGGGGATTC CAGGGTGGAG CT                                              22

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

ACCTGCTCTC AGGGCCCACA AGT                                             23

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

TAAGACAAAG AACAGGTCAC AACA                                            24

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

ATTTGTGCTT AGAGGTCGTG CCAG                                            24

(2) INFORMATION FOR SEQ ID NO:10:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

Leu Ala Met Cys Thr Asn Leu Pro Glu Ala Arg Val Gln Val Trp Phe
1               5                   10                  15

Lys Asn Arg Arg Ala Lys Phe Arg
            20

(2) INFORMATION FOR SEQ ID NO:11:

(i) SEQUENCE CHARACTERISTICS:
        (A) LENGTH: 25 amino acids

```
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:11:

Ser Ser Ser Lys Val His Ser Phe Gly Lys Arg Asp Gln Ala Ile Arg
1               5                  10                  15

Arg Asn Pro Asn Val Pro Val Val Val
            20                  25

(2) INFORMATION FOR SEQ ID NO:12:

(i) SEQUENCE CHARACTERISTICS:
          (A) LENGTH: 5 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /product= "OTHER"
               /note= "Xaa = Ala or Pro"

(ix) FEATURE:
          (A) NAME/KEY: Modified-site
          (B) LOCATION: 4
          (D) OTHER INFORMATION: /product= "OTHER"
               /note= "Xaa = Ala or Pro"

(xi) SEQUENCE DESCRIPTION: SEQ ID NO:12:

Xaa Pro Pro Xaa Tyr
1               5

(2) INFORMATION FOR SEQ ID NO:13:

(i) SEQUENCE CHARACTERISTICS:
          (A) LENGTH: 26 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:13:

Trp Ser Tyr Gly Val Cys Arg Asp Gly Arg Val Phe Phe Ile Asn Asp
1               5                  10                  15

Gln Leu Arg Cys Thr Thr Trp Leu His Pro
            20                  25

(2) INFORMATION FOR SEQ ID NO:14:

(i) SEQUENCE CHARACTERISTICS:
          (A) LENGTH: 24 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:14:

Trp Phe Val Leu Ala Asp Tyr Cys Leu Phe Tyr Tyr Lys Ala Glu Lys
1               5                  10                  15

Lys Arg Ser Ser Xaa Ser Ile Pro
            20
```

(2) INFORMATION FOR SEQ ID NO:15:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:15:

```
Trp Glu Glu Gly Phe Thr Glu Glu Gly Ala Ser Tyr Phe Ile Asp His
 1               5                  10                  15

Asn Gln Gln Thr Thr Ala Phe Arg His Pro
            20                  25
```

(2) INFORMATION FOR SEQ ID NO:16:

(i) SEQUENCE CHARACTERISTICS:
        (A) LENGTH: 100 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:16:

```
Pro Asn Ile Pro Gln Met Ser Ala Phe Trp Tyr Ala Val Arg Thr Ala
 1               5                  10                  15

Val Ile Asn Ala Ala Ser Gly Arg Gln Thr Val Asp Glu Ala Leu Lys
                20                  25                  30

Asp Ala Gln Thr Asn Ser Ser Ser Asn Asn Asn Asn Asn Asn Asn Asn
                35                  40                  45

Asn Asn Leu Gly Ile Glu Gly Arg Ile Ser Glu Phe Ala Ala Ala Ser
            50                  55                  60

Thr Leu Asp Leu Lys Met Thr Gly Arg Asp Leu Leu Lys Asp Arg Ser
65                  70                  75                  80

Leu Lys Pro Val Lys Ile Ala Glu Ser Asp Thr Asp Val Lys Leu Ser
                85                  90                  95

Ile Phe Cys Glu
            100
```

(2) INFORMATION FOR SEQ ID NO:17:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:17:

```
Arg Gly Leu Lys Arg Gln Ser Asp Glu Arg Lys Arg Asp Arg Glu
 1               5                  10                  15
```

(2) INFORMATION FOR SEQ ID NO:18:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:18:

Lys Val Thr Ser Pro Leu Gln Ser Pro Thr Lys Ala Lys Pro Lys
1               5                  10                  15

(2) INFORMATION FOR SEQ ID NO:19:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (ix) FEATURE:
           (A) NAME/KEY: modified_base
           (B) LOCATION: 1
           (D) OTHER INFORMATION: /mod_base= OTHER
               /note= "N = 5'-phosphorylated adenine
               (p-A)"

(ix) FEATURE:
           (A) NAME/KEY: modified_base
           (B) LOCATION: 20
           (D) OTHER INFORMATION: /mod_base= OTHER
               /note= "N = adenine substituted at the
               3' position of deoxyribose with an amino
               group (A-NH-2)"

(xi) SEQUENCE DESCRIPTION: SEQ ID NO:19:

NTAGCGGCCG CAAGAATTCN                                          20

(2) INFORMATION FOR SEQ ID NO:20:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:20:

TGAATTCTTG CGGCCGCTAT                                          20

(2) INFORMATION FOR SEQ ID NO:21:

(i) SEQUENCE CHARACTERISTICS:
           (A) LENGTH: 25 base pairs
           (B) TYPE: nucleic acid
           (C) STRANDEDNESS: single
           (D) TOPOLOGY: linear (ii) MOLECULE TYPE: DNA (ix) FEATURE:
           (A) NAME/KEY: modified_base
           (B) LOCATION: 1
           (D) OTHER INFORMATION: /mod_base= OTHER
               /note= "N = 5'-phosphorylated cytosine
               (p-C)"

(ix) FEATURE:
           (A) NAME/KEY: modified_base
           (B) LOCATION: 25
           (D) OTHER INFORMATION: /mod_base= OTHER
               /note= "N = guanine substituted at the
               3' position of deoxyribose with an amino
               group (G-NH-2)"

(xi) SEQUENCE DESCRIPTION: SEQ ID NO:21:

NAGAAGCTTG GTTGGATCCA GCAAN                                         25

(2) INFORMATION FOR SEQ ID NO:22:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

CTTGCTGGAT CCAACCAAGC TTCTG                                         25

(2) INFORMATION FOR SEQ ID NO:23:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

CTCACTGTAG ACACTGCCTC AGTTTC                                        26

(2) INFORMATION FOR SEQ ID NO:24:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

CAGAGGCTGG CACTGGAACT CAAGATC                                       27

(2) INFORMATION FOR SEQ ID NO:25:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

TCTAACCCTA ACTGAGAAGG GCGTAG                                        26

(2) INFORMATION FOR SEQ ID NO:26:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

GTTTGCTCTA GAATGAACGG TGGAAG                                        26